United States Patent
Goto et al.

(10) Patent No.: US 8,366,963 B2
(45) Date of Patent: Feb. 5, 2013

(54) COMPOUND HAVING HYDROCOUMARIN SKELETON, LIQUID CRYSTAL COMPOSTITION, AND LIQUID CRYSTAL DISPLAY DEVICE

(75) Inventors: Mayumi Goto, Chiba (JP); Teruyo Sugiura, Chiba (JP); Norikatsu Hattori, Chiba (JP); Kouki Sagou, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

(21) Appl. No.: 13/084,268

(22) Filed: Apr. 11, 2011

(65) Prior Publication Data

US 2011/0193021 A1    Aug. 11, 2011

Related U.S. Application Data

(62) Division of application No. 12/094,264, filed as application No. PCT/JP2006/324546 on Dec. 8, 2006, now Pat. No. 7,951,305.

(30) Foreign Application Priority Data

Dec. 8, 2005  (JP) ................................. 2005-355179

(51) Int. Cl.
    C09K 19/34    (2006.01)
    C09K 19/32    (2006.01)
    C09K 19/52    (2006.01)
    C09K 19/06    (2006.01)
    C07D 311/00   (2006.01)

(52) U.S. Cl. ........... 252/299.61; 252/299.01; 252/299.6; 252/299.62; 252/299.63; 428/1.1; 428/1.3; 549/290; 549/289; 549/398; 349/182

(58) Field of Classification Search ............. 252/299.01, 252/299.6, 299.61, 299.62, 299.63; 428/1.1, 428/1.3; 549/289, 290, 398; 349/182
See application file for complete search history.

(56) References Cited

U.S. PATENT DOCUMENTS

| | | | |
|---|---|---|---|
| 5,639,893 A | 6/1997 | Iwamoto et al. | 549/290 |
| 6,057,906 A | 5/2000 | Iwanaga et al. | 349/182 |
| 2005/0014818 A1 | 1/2005 | Mitsuda et al. | 514/456 |
| 2007/0200092 A1 | 8/2007 | Matsui et al. | 252/299.01 |
| 2008/0071097 A1 | 3/2008 | Taugerbeck et al. | 549/406 |

FOREIGN PATENT DOCUMENTS

| | | |
|---|---|---|
| DE | 4426799 | 2/1995 |
| JP | 03-240783 | 10/1991 |
| JP | 04-210687 | 7/1992 |
| JP | 06-336459 | 12/1994 |
| JP | 2004-292774 | 10/2004 |
| WO | WO 2004/076438 | 9/2004 |

OTHER PUBLICATIONS

Stojan Stavber et al., "Chemistry of Organo Halogenic Molecules. Part 100. Comparative Behaviour of Xenon Difluoride and Caesium Fluoroxysulphate in the Fluorination of Enol Acetates and Ketones" Tetrahedron, vol. 45, No. 18, (1989), pp. 6003-6010.
Paolo Bovicelli et al., "Oxidation of 3-Arylisochromans by Dimethyldioxirane. An Easy Route to Substituted 3-Arylisocoumarins" Tetrahedron, vol. 55, (1999), pp. 14719-14728.
Peter P. Fu et al., "Synthesis of 3-Arl-3, 4-dihydroisocoumarins" The Journal of Organic Chemistry, vol. 50, (1985), pp. 1259-1261.
Z. Shafiq et al., "Synthesis of Some New Dihalophenyl- ,Dihalo-benzylisocoumarins and their (dl)-3,4-Dihydro Analogs" Indian Journal of Heterocyclic Chemistry, vol. 14, (Apr.-Jun. 2005), pp. 277-280.
Abid Hussain et al., "Synthesis of Some New 3-(Iodophenyl) Isocoumarins and their Conversion to (dl)-3,4-Dihydro-Derivatives" Indian Journal of Heterocyclic Chemistry, vol. 8, (Jan.-Mar. 1999), pp. 189-192.
Alok K. Mitra et al., "New Synthesis of 3-Alkyl Coumarins" Synthetic Communications, vol. 10, No. 12, (1980), pp. 915-919.
Carmela Gnerre et al., "Inhibition of Monoamine Oxidases by Functionalized Coumarin Derivatives: Biological Activities, QSARs, and 3D-QSARs" Journal of Medicinal Chemistry, vol. 43, No. 25, (2000), pp. 4747-4758.
N. Choukchou-Braham et al., "A Case of Pictet-Spengler Revisited: Application to the Synthesis of Dihydroisocoumarins" Synthetic Communications, vol. 35, No. 2(2005), pp. 169-178.
Barbara Zajc et al., "Fluorination with Xenon Difluoride. 37. Room-Temperature Rearrangement of Aryl-Substituted Ketones to Difluoro-Substituted Ethers" Journal of Organic Chemistry. vol. 55, No. 3, (1990), pp. 1099-1102.
The Supplemental European Search Report of European Application No. EP 06 83 4301.1, dated May 31, 2011.
"Office Action of European Counterpart Application", issued on Jun. 19, 2012, p. 1-p. 5.
Indian Journal of Chemistry (Section B), 1979, p. 295, vol. 17B(3).
Tarumi et al., "Recent Liquid Crystal Material Development for Active Matrix Displays," Annual Review of Materials Science, vol. 27, 1997, pp. 423-441.

*Primary Examiner* — Geraldina Visconti
(74) *Attorney, Agent, or Firm* — J.C. Patents

(57) ABSTRACT

A liquid crystal compound is to be obtained that has stability to heat, light and so forth, a high clearing point, a suitable optical anisotropy, a large negative dielectric anisotropy, and excellent compatibility with other liquid crystal compounds. A liquid crystal composition containing the compound is also to be obtained that has a low viscosity, a suitable optical anisotropy, a suitable negative dielectric anisotropy, a low threshold voltage, a high maximum temperature of a nematic phase (phase transition temperature from a nematic phase to an isotropic phase), and a low minimum temperature of a nematic phase. A compound having a hydrocoumarin skeleton is synthesized, and a liquid crystal composition containing the compound is produced.

13 Claims, No Drawings

COMPOUND HAVING HYDROCOUMARIN SKELETON, LIQUID CRYSTAL COMPOSTITION, AND LIQUID CRYSTAL DISPLAY DEVICE

CROSS-REFERENCE TO RELATED APPLICATION

This application is a divisional application of a prior U.S. application Ser. No. 12/094,264, filed on May 19, 2008 now U.S. Pat. No. 7,951,305. The prior U.S. application Ser. No. 12/094,264, is a 371 of an International application Ser. No. PCT/JP2006/324546, filed on Dec. 8, 2006, and claims the priority benefit of Japan application Ser. No. JP2005-355179, filed on Dec. 8, 2005. The entirety of the above-mentioned patent applications are hereby incorporated by reference herein and made a part of this specification.

BACKGROUND OF THE INVENTION

1. Field of the Invention

The invention relates to a compound having a hydrocoumarin skeleton, a liquid crystal composition, and a liquid crystal display device.

2. Related Art

A liquid crystal display device is classified, depending on the display mode thereof, into such modes as DS (dynamic scattering), TN (twisted nematic), GH (guest host), STN (super twisted nematic), IPS (in-plane switching), VA (vertical alignment) and OCB (optically compensated bend). A liquid crystal composition contained in the liquid crystal display devices desirably has some or all of the following common characteristics in all the display modes.
(1) The composition is stable to external environmental factors, such as water, air, heat and light.
(2) The composition exhibits a liquid crystal phase in a wide temperature range centering around room temperature.
(3) The composition has a small viscosity.
(4) The composition can decrease a driving voltage upon driving the display device.
(5) The composition has an optimum dielectric anisotropy (Δ∈).
(6) The composition has an optimum optical anisotropy (Δn).

However, such a liquid crystal compound has not yet been found that satisfies all of characteristics (1) to (6) by a sole compound. Therefore, a liquid crystal composition is often obtained by mixing several kinds (e.g., a couple dozen kinds) of liquid crystal compounds. Accordingly, the liquid crystal compounds used as components of the composition necessarily have good compatibility with each other. A liquid crystal display device capable of being used in various environments, such as a very low temperature, has been demanded in recent years, and liquid crystal compounds exhibiting good compatibility at a very low temperature are thus also demanded.

In recent years, among the aforementioned display modes, such modes as IPS, VA and OCB are receiving attention as a display mode capable of overcoming a narrow viewing angle of a liquid crystal display device, which is the biggest problem of a liquid crystal display device. In particular, liquid crystal display devices of the VA mode and the IPS mode among these modes are being developed earnestly since it has excellent response in addition to the wide viewing angle, and is capable of providing high-contrast display. The characteristics of the liquid crystal composition used in the liquid crystal display device of these modes reside in a negative dielectric anisotropy. It has been known that a liquid crystal composition having a large negative dielectric anisotropy can decrease the driving voltage of a liquid crystal display device containing the liquid crystal composition (as described in M. F. Leslie, Mol. Cryst. Liq. Cryst., vol. 12, p. 57 (1970)). Accordingly, liquid crystal compounds as the constitutional components of the liquid crystal composition are also demanded to have a larger negative dielectric anisotropy.

As a component of a liquid crystal composition having a negative dielectric anisotropy, various liquid crystal compounds where hydrogen at a lateral position of a benzene ring is replaced by fluorine have been investigated (as described, for example, in Japanese Patent No. 2,811,342 and JP H2-4725 A/1990). The following compound (c) (wherein R and R' are alkyls) has been reported, for example.

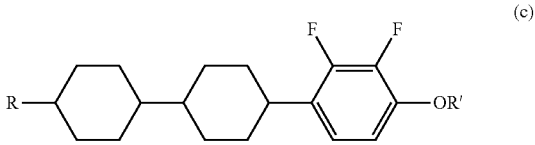

However, the compounds exemplified by the compound (c) have a negative dielectric anisotropy, but the extent thereof is not necessarily large in some cases, and therefore, the compounds are not sufficient in some cases for decreasing the driving voltage of the liquid crystal display devices of the VA mode and the IPS mode.

As a liquid crystal compound having a large negative dielectric anisotropy, the compound (d) has also been reported (as described in JP S59-10557 A/1984). The compound (d) (wherein R and R' are alkyls) has a considerably large negative dielectric anisotropy, but is not necessarily sufficient in chemical and physical stability.

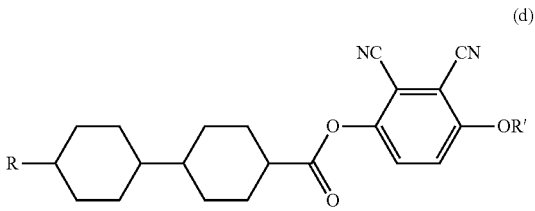

In addition to the aforementioned compounds, compounds having hydrocoumarin have also been reported (JP H3-240783 A/1991, JP 1-14-210687 A/1992 and JP 2004-292774 A/2004).

For example, JP H3-240783 A/1991 and JP 1-14-210687 A/1992 disclose compounds having a hydrocoumarin skeleton, but the purposes of the compounds are restricted to a ferroelectric liquid crystal. The compounds specifically disclosed in JP H3-240783 A/1991 and JP H4-210687 A/1992 have a carboxyl group having branched alkyl or a long-chain alkyl group at an end thereof. However, these compounds are not suitable for use as a nematic liquid crystal due to a high viscosity and a strong smectic nature thereof.

JP 2004-292774 A/2004 discloses a general formula containing a skeleton that is apparently similar to the compound of the invention. However, the compound that has been clarified for the structural formula and properties thereof is limited to one having one benzene ring and one lactone ring, and a liquid crystal composition containing the compound is liable to have a low clearing point. Accordingly, the compound has room for improvement upon using as a nematic liquid crystal.

SUMMARY OF THE INVENTION

The invention concerns a compound represented by general formula (a):

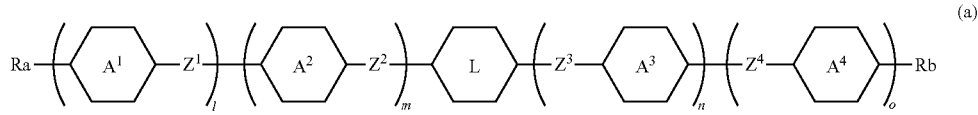

In general formula (a), Ra and Rb are each independently hydrogen, halogen or alkyl having 1 to 9 carbons, provided that in the alkyl, —$CH_2$— may be replaced by —O—, —$CH_2CH_2$— may be replaced by —CH=CH—, and hydrogen may be replaced by halogen; rings $A^1$, $A^2$, $A^3$ and $A^4$ are each independently trans-1,4-cyclohexylene or 1,4-phenylene, provided that in these rings, hydrogen may be replaced by halogen, and in the case where the ring is trans-1,4-cyclohexylene, —$CH_2$— may be replaced by —O— or —CH=CH—, and in the case where the ring is 1,4-phenylene, —CH= may be replaced by —N=; $Z^1$, $Z^2$, $Z^3$ and $Z^4$ are each independently a single bond or alkylene having 1 to 4 carbons, provided that in the alkylene, arbitrary —$CH_2$— may be replaced by —O— or —CO—, arbitrary —$CH_2CH_2$— may be replaced by —CH=CH— or —C≡C—, and arbitrary hydrogen may be replaced by halogen; l, m, n and o are each independently 0 or 1; and ring L is ring L1 or ring L2:

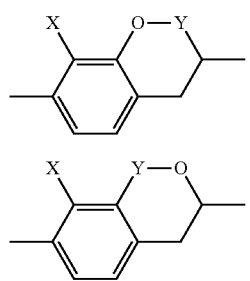

In ring L1 and ring L2, X is hydrogen or halogen; and Y is —C(=O)— or —$CF_2$—.

The invention also concerns a liquid crystal composition that includes the compound, a liquid crystal display device that includes the liquid crystal composition, and so forth.

DETAILED DESCRIPTION OF THE INVENTION

One of the advantages of the invention is to provide a liquid crystal compound that has stability to heat, light and so forth, a high clearing point, a suitable optical anisotropy, a large negative dielectric anisotropy, and excellent compatibility with other liquid crystal compounds. The clearing point referred herein is a temperature, at which a liquid crystal compound transfers from a certain phase to an isotropic phase, and is specifically phase transition temperatures from a nematic phase to an isotropic phase, from a smectic phase to an isotropic phase, and from a crystalline phase to an isotropic phase.

Another one of the advantages of the invention is to provide a liquid crystal composition that contains the compound and has a low viscosity, a suitable optical anisotropy, a suitable negative dielectric anisotropy, a low threshold voltage, a high maximum temperature of a nematic phase (phase transition temperature from a nematic phase to an isotropic phase), and a low minimum temperature of a nematic phase.

Still another one of the advantages of the invention is to provide a liquid crystal display device that contains the composition, has a short response time, a small electric power consumption, a small driving voltage and a large contrast, and is capable of being used in a wide temperature range.

It has been found that a particular compound having a hydrocoumarin skeleton has stability to heat, light and so forth, a suitable optical anisotropy, a large negative dielectric anisotropy and excellent compatibility with other liquid crystal compounds; a liquid crystal composition containing the compound has a small viscosity, a suitable optical anisotropy, a suitable negative dielectric anisotropy, a low threshold voltage, a high maximum temperature of a nematic phase, and a low minimum temperature of a nematic phase; and a liquid crystal display device containing the composition has a short response time, a small electric power consumption, a small driving voltage and a large contrast, and is capable of being used in a wide temperature range, and such an intermediate compound has been found that has stability to heat, light and so forth, is capable of being applied to a wide variety of reactions, and is capable of producing the liquid crystal compound of the invention.

The inventions has the following features:

1. A compound represented by general formula (a):

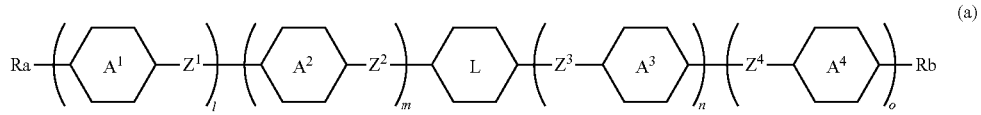

wherein in general formula (a),

Ra and Rb are each independently hydrogen, halogen or alkyl having approximately 1 to approximately 9 carbons, provided that in the alkyl, —$CH_2$— may be replaced by —O—, —$CH_2CH_2$— may be replaced by —CH=CH—, and hydrogen may be replaced by halogen;

rings $A^1$, $A^2$, $A^3$ and $A^4$ are each independently trans-1,4-cyclohexylene or 1,4-phenylene, provided that in these rings, hydrogen may be replaced by halogen, and in the case where the ring is trans-1,4-cyclohexylene, —$CH_2$— may be replaced by —O— or —CH=CH—, and in the case where the ring is 1,4-phenylene, —CH= may be replaced by —N=;

$Z^1$, $Z^2$, $Z^3$ and $Z^4$ are each independently a single bond or alkylene having 1 to 4 carbons, provided that in the alkylene, arbitrary —CH$_2$— may be replaced by —O— or —CO—, arbitrary —CH$_2$CH$_2$— may be replaced by —CH=CH— or —C≡C—, and arbitrary hydrogen may be replaced by halogen;

l, m, n and o are each independently 0 or 1; and ring L is ring L1 or ring L2:

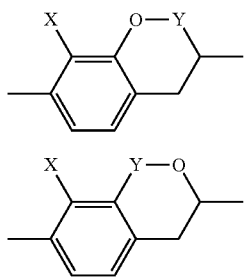

wherein in ring L1 and ring L2,
X is hydrogen or halogen; and
Y is —C(=O)— or —CF$_2$—.

2. A compound represented by any one of general formulas (a-1) to (a-7):

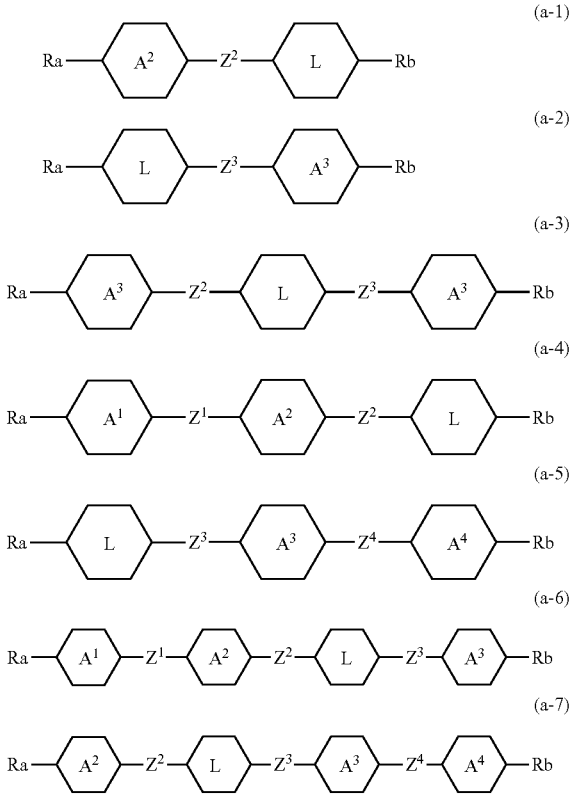

wherein in general formulas (a-1) to (a-7),

Ra and Rb are each independently hydrogen, halogen or alkyl having approximately 1 to approximately 9 carbons, provided that in the alkyl, —CH$_2$— may be replaced by —O—, —CH$_2$CH$_2$— may be replaced by —CH=CH—, and hydrogen may be replaced by halogen;

rings $A^1$, $A^2$, $A^3$ and $A^4$ are each independently trans-1,4-cyclohexylene or 1,4-phenylene, provided that in these rings, hydrogen may be replaced by halogen, and in the case where the ring is trans-1,4-cyclohexylene, —CH$_2$— may be replaced by —O— or —CH=CH—, and in the case where the ring is 1,4-phenylene, —CH= may be replaced by —N=;

$Z^1$, $Z^2$, $Z^3$ and $Z^4$ are each independently a single bond or alkylene having 1 to 4 carbons, provided that in the alkylene, arbitrary —CH$_2$— may be replaced by —O— or —CO—, arbitrary —CH$_2$CH$_2$— may be replaced by —CH=CH— or —C≡C—, and arbitrary hydrogen may be replaced by halogen; and ring L is ring L1 or ring L2:

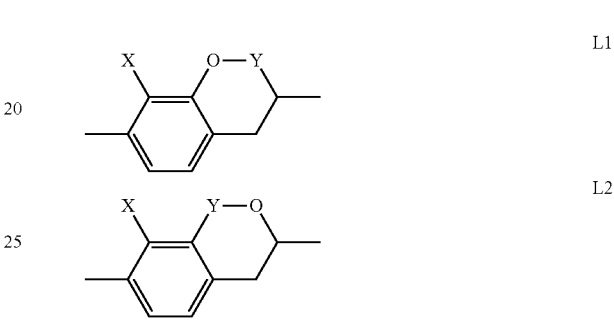

wherein in ring L1 and ring L2,
X is hydrogen or halogen; and
Y is —C(=O)— or —CF$_2$—.

3. The liquid crystal composition represented by any one of general formulas (a-1) to (a-7) according to item 2, wherein in ring L1 or L2, X is fluorine.

4. The liquid crystal composition represented by any one of general formulas (a-1) to (a-7) according to item 2, wherein
in ring L1 or L2, X is hydrogen;
in formula (a-1), $Z^1$ is independently —(CH$_2$)$_2$—, —CH$_2$O—, —OCH$_2$—, —CF$_2$O—, —OCF$_2$—, —COO—, —COO—, —CH$_2$CO—, —COCH$_2$—, —CH=CH—, —CF=CF—, —C≡C—, —(CH$_2$)$_4$—, —(CH$_2$)$_2$COO—, —OCO(CH$_2$)$_2$—, —(CH$_2$)$_3$O—, —O(CH$_2$)$_3$—, —(CH$_2$)$_2$CF$_2$O— or —OCF$_2$(CH$_2$)$_2$— when Ra is alkyl, ring $A^2$ is 1,4-phenylene, hydrogen of which may be replaced by a halogen, and Y in ring L2 is —C(=O)—;

in formula (a-4), $Z^2$ is independently a single bond, —(CH$_2$)$_2$—, —CF$_2$O—, —OCF$_2$—, —CH$_2$CO—, —COCH$_2$—, —CH=CH—, —CF=CF—, —C≡C—, —(CH$_2$)$_4$—, —(CH$_2$)$_2$COO—, —OCO(CH$_2$)$_2$—, —(CH$_2$)$_3$O—, —O(CH$_2$)$_3$—, —(CH$_2$)$_2$CF$_2$O— or —OCF$_2$(CH$_2$)$_2$— when rings $A^1$ and $A^2$ are each 1,4-phenylene, hydrogen of which may be replaced by a halogen, and Y in ring L2 is —C(=O)—; and in formula (a-4), $Z^1$ is independently a single bond, —(CH$_2$)$_2$—, —CH$_2$O—, —CF$_2$O—, —OCF$_2$—, —COO—, —CH$_2$CO—, —COCH$_2$—, —CH=CH—, —CF=CF—, —C≡C—, —(CH$_2$)$_4$—, —(CH$_2$)$_2$COO—, —OCO (CH$_2$)$_2$—, —(CH$_2$)$_3$O—, —O(CH$_2$)$_3$—, —(CH$_2$)$_2$CF$_2$O— or —OCF$_2$(CH$_2$)$_2$— when rings $A^1$ and $A^2$ are each 1,4-phenylene, hydrogen of which may be replaced by a halogen, $Z^2$ is a single bond, and Y in ring L2 is —C(=O)—.

5. The liquid crystal composition represented by any one of general formulas (a-1) to (a-7) according to item 2, wherein in ring L1 or L2, X is fluorine, and Y is —C(=O)—.

6. The liquid crystal composition represented by any one of general formulas (a-1) to (a-7) according to item 2, wherein in ring L1 or L2, X is hydrogen, and Y is —C(=O)—;

in formula (a-1), $Z^1$ is independently —(CH$_2$)$_2$—, —CH$_2$O—, —OCH$_2$—, —CF$_2$O—, —OCF$_2$—, —COO—, —COO—, —CH$_2$CO—, —COCH$_2$—, —CH=CH—, —CF=CF—, —C≡C—, —(CH$_2$)$_4$—, —(CH$_2$)$_2$COO—, —OCO(CH$_2$)$_2$—, —(CH$_2$)$_3$O—, —O(CH$_2$)$_3$—, —(CH$_2$)$_2$CF$_2$O— or —OCF$_2$(CH$_2$)$_2$— when ring L is ring L2, Ra is alkyl, and ring $A^2$ is 1,4-phenylene, hydrogen of which may be replaced by a halogen;

in formula (a-4), $Z^2$ is independently a single bond, —(CH$_2$)$_2$—, —CF$_2$O—, —OCF$_2$—, —CH$_2$CO—, —COCH$_2$—, —CH=CH—, —CF=CF—, —C≡C—, —(CH$_2$)$_4$—, —(CH$_2$)$_2$COO—, —OCO(CH$_2$)$_2$—, —(CH$_2$)$_3$O—, —O(CH$_2$)$_3$—, —(CH$_2$)$_2$CF$_2$O— or —OCF$_2$(CH$_2$)$_2$— when ring L is ring L2, and rings $A^1$ and $A^2$ are each 1,4-phenylene, hydrogen of which may be replaced by a halogen; and in formula (a-4), $Z^1$ is independently a single bond, —(CH$_2$)$_2$—, —CH$_2$O—, —CF$_2$O—, —OCF$_2$—, —COO—, —CH$_2$CO—, —COCH$_2$—, —CH=CH—, —CF=CF—, —C≡C—, —(CH$_2$)$_4$—, —(CH$_2$)$_2$COO—, —OCO(CH$_2$)$_2$—, —(CH$_2$)$_3$O—, —O(CH$_2$)$_3$—, —(CH$_2$)$_2$CF$_2$O— or —OCF$_2$(CH$_2$)$_2$— when ring L is ring L2, $A^1$ and $A^2$ are each 1,4-phenylene, hydrogen of which may be replaced by a halogen, and $Z^2$ is a single bond.

7. The liquid crystal composition represented by any one of general formulas (a-1) to (a-7) according to item 2, wherein Ra and Rb are each alkyl having 1 to 9 carbons or alkoxy having 1 to 8 carbons; and in ring L1 or L2, X is fluorine, and Y is —C(=O)—.

8. The liquid crystal composition represented by any one of general formulas (a-1) to (a-7) according to item 2, wherein in ring L1 or L2, X is fluorine, and Y is —CF$_2$—.

9. The liquid crystal composition represented by any one of general formulas (a-1) to (a-7) according to item 2, wherein in ring L1 or L2, X is hydrogen, and Y is —CF$_2$—.

10. A liquid crystal composition comprising at least one compound selected from the group of the compound according to any one of items 1 to 9.

11. The liquid crystal composition according to item 10, the composition further comprises at least one compound selected from the group of compounds represented by formulas (1), (2), (3), (4), (5), (6), (7), (8) and (9):

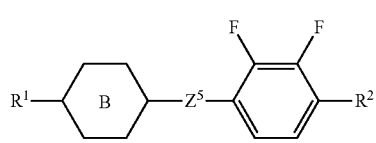

(1)

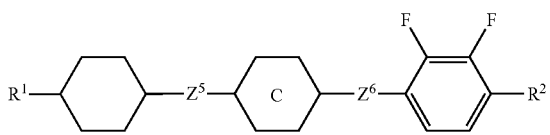

(2)

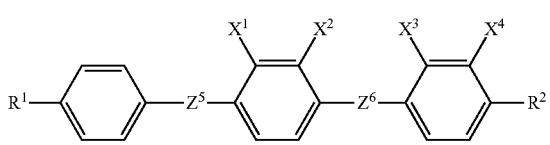

(3)

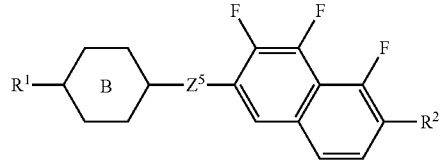

(4)

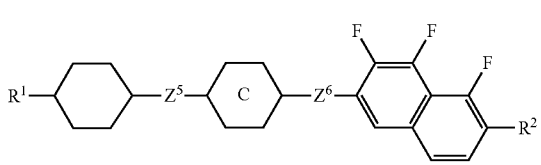

(5)

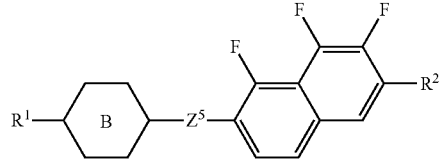

(6)

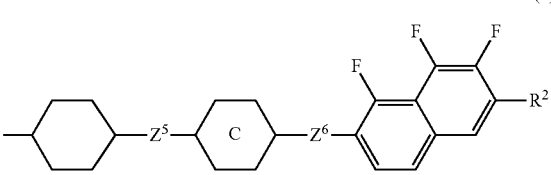

(7)

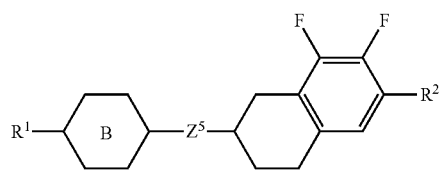

(8)

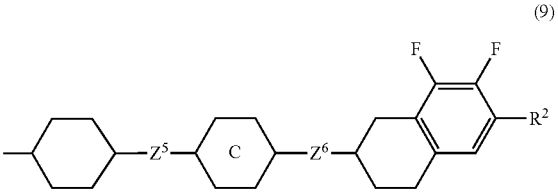

(9)

wherein in formulas (1) to (9), $R^1$ and $R^2$ are each independently alkyl having 1 to 10 carbons, provided that in the alkyl, —CH$_2$— may be replaced by —O—, —(CH$_2$)$_2$— may be replaced by —CH=CH—, and arbitrary hydrogen may be replaced by fluorine, and $R^1$ may be fluorine;

ring B and ring C are each independently 1,4-cyclohexylene, 1,4-phenylene or decahydro-2,6-naphthylene;

$Z^5$ and $Z^6$ are each independently —(CH$_2$)$_2$—, —COO— or a single bond; and $X^1$, $X^2$, $X^3$ and $X^4$ are each independently hydrogen or fluorine, provided that at least one of $X^1$, $X^2$, $X^3$ and $X^4$ is fluorine.

12. The liquid crystal composition according to item 10, the composition further comprises at least one compound selected from the group of compounds represented by formulas (10), (11) and (12):

(10)

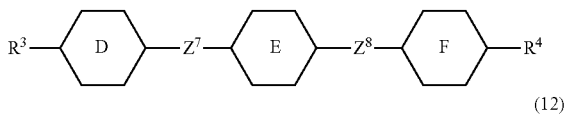

(11)

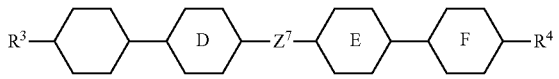

(12)

wherein in formulas (10) to (12), $R^3$ and $R^4$ are each independently alkyl having 1 to 10 carbons, provided that in the alkyl, —$CH_2$— may be replaced by —O—, —$(CH_2)_2$— may be replaced by —CH=CH—, and hydrogen may be replaced by fluorine;

ring D, ring E and ring F are each independently 1,4-cyclohexylene, pyrimidine-2,5-diyl, or 1,4-phenylene, arbitrary hydrogen of which may be replaced by fluorine; and $Z^7$ and $Z^8$ are each independently —COO—, —$(CH_2)_2$—, —CH=CH— or a single bond.

13. The liquid crystal composition according to item 11, the composition further comprises at least one compound selected from the group of compounds represented by formulas (10), (11) and (12) in item 12.

14. The liquid crystal composition according to any one of items 10 to 13, wherein the composition further comprises at least one optically active compound.

15. A liquid crystal display device comprising the liquid crystal composition according to any one of items 10 to 14.

According to the invention, a liquid crystal compound is obtained that has stability to heat, light and so forth, a high clearing point, a suitable optical anisotropy, a large negative dielectric anisotropy, and excellent compatibility with other liquid crystal compounds. According to the invention, furthermore, a liquid crystal composition is obtained that has a low viscosity, a suitable optical anisotropy, a suitable negative dielectric anisotropy, a low threshold voltage, a high maximum temperature of a nematic phase (phase transition temperature from a nematic phase to an isotropic phase), and a low minimum temperature of a nematic phase. According to the invention, moreover, a liquid crystal display device is obtained that has a short response time, a small electric power consumption, a small driving voltage and a large contrast, and is capable of being used in a wide temperature range.

The invention concerns, as one aspect, a compound having a hydrocoumarin skeleton described in detail below.

having 2 to 9 carbons, alkenyloxy having 2 to 8 carbons, alkenyloxyalkyl having 3 to 8 carbons and alkoxyalkenyl having 3 to 8 carbons. The alkyl chain in these groups is preferably linear alkyl. In the case where the alkyl is linear alkyl, the temperature range of the liquid crystal phase can be widened, and the viscosity can be decreased.

One or more hydrogen in these groups may be replaced by halogen, and the halogen for replacing hydrogen is preferably fluorine and chlorine.

Ra and Rb are preferably alkyl, alkoxy, alkoxyalkyl, alkenyl, fluoroalkyl or fluoroalkoxy, more preferably alkyl, alkoxy, alkoxyalkyl or alkenyl, and further preferably alkyl, alkoxy or alkenyl. The configuration of the alkenyl is preferably a trans configuration.

Examples of the alkyl include —$CH_3$, —$C_2H_5$, —$C_3H_7$, —$C_4H_9$, —$C_5H_{10}$, —$C_6H_{13}$, —$C_7H_{15}$, —$C_8H_{17}$ and —$C_9H_{19}$.

Examples of the alkoxy include —$OCH_3$, —$OC_2H_5$, —$OC_3H_7$, —$OC_4H_9$, —$OC_5H_{10}$, —$OC_6H_{13}$, —$OC_7H_{15}$ and —$OC_8H_{17}$.

Examples of the alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$ and —$(CH_2)_3$CH=$CM_2$.

Examples of the alkenyloxy include —$OCH_2$CH=$CH_2$, —$OCH_2$CH=$CHCH_3$ and —$OCH_2$CH=$CHC_2H_5$.

Examples of the alkyl, in which hydrogen is replaced by halogen, include —$CH_2F$, —$CHF_2$, —$CF_3$, —$(CH_2)_2F$, —$CF_2CH_2F$, —$CF_2CHF_2$, —$CH_2CF_3$, —$CF_2CF_3$, —$(CH_2)_3F$, —$(CF_2)_2CF_3$, —$CF_2CHFCF_3$ and —$CHFCF_2CF_3$.

Examples of the alkoxy, in which hydrogen is replaced by halogen, include —$OCF_3$, —$OCHF_2$, —$OCH_2F$, —$OCF_2CF_3$, —$OCF_2CHF_2$, —$OCF_2CH_2F$, —$OCF_2CF_2CF_3$, —$OCF_2CHFCF_3$ and —$OCHFCF_2CF_3$.

Examples of the alkenyl, in which hydrogen is replaced by halogen, include —CH=CHF, —CH=$CF_2$, —CF=CHF, —CH=$CHCH_2F$, —CH=$CHCF_3$ and —$(CH_2)_2$CH=$CF_2$.

Among these groups for Ra and Rb, —$CH_3$, —$C_2H_5$, —$C_3H_7$, —$C_4H_9$, —$C_5H_{10}$, —$C_6H_{13}$, —$C_7H_{15}$, —$C_8H_{17}$, —$C_9H_{19}$, —$OCH_3$, —$OC_2H_5$, —$OC_3H_7$, —$OC_4H_9$, —$OC_5H_{10}$, —$OC_6H_{13}$, —$OC_7H_{15}$, —$OC_8H_{17}$, —CH=$CH_2$, —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$ and —$(CH_2)_3$CH=$CH_2$ are preferred, and —$CH_3$, —$C_2H_5$, —$C_3H_7$, —$C_4H_9$, —$C_5H_{10}$, —$OCH_3$, —$OC_2H_5$, —$OC_3H_7$, —$OC_4H_9$, —$OC_5H_{10}$, —CH=$CH_2$, —CH=$CHCH_3$, —$CH_2$CH=$CH_2$, —C=$CHC_2H_5$, —$CH_2$CH=$CHCH_3$, —$(CH_2)_2$CH=$CH_2$,

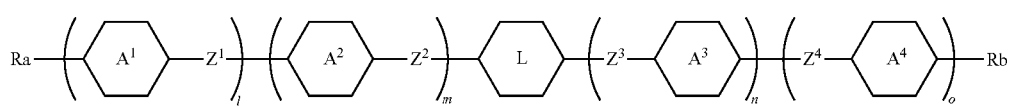

(a)

—CH=$CHC_3H_7$, —$CH_2$CH=$CHC_2H_5$, —$(CH_2)_2$CH=$CHCH_3$ and —$(CH_2)_3$CH=$CH_2$ are more preferred.

In the compound (a), Ra and Rb are each independently hydrogen, halogen or alkyl having 1 to 9 carbons, provided that in the alkyl, —$CH_2$— may be replaced by —O—, and —$CH_2CH_2$— may be replaced by —CH=CH—.

Examples of Ra and Rb include hydrogen, alkyl having 1 to 9 carbons, alkoxy having 1 to 8 carbons, alkoxyalkyl having 2 to 8 carbons, alkoxyalkoxy having 2 to 7 carbons, alkenyl In the compound (a), rings $A^1$, $A^2$, $A^3$ and $A^4$ are each independently trans-1,4-cyclohexylene or 1,4-phenylene, provided that in these rings, hydrogen may be replaced by halogen, and in the case where the ring is trans-1,4-cyclohexylene, —$CH_2$— may be replaced by —O— or —CH═CH—, and in the case where the ring is 1,4-phenylene, —CH═ may be replaced by —N═.

In the case where the rings are trans-1,4-cyclohexylene, the optical anisotropy (Δn) can be decreased, and the viscosity can be decreased. In the case where the liquid crystal compound is added to a liquid crystal composition, the maximum temperature ($T_{NI}$) of a nematic phase of the composition can be increased.

In the case where the rings are 1,4-phenylene, hydrogen of which may be replaced by a halogen, the optical anisotropy (Δn) can be relatively increased, and the orientational order parameter can be increased.

As rings $A^1$, $A^2$, $A^3$ and $A^4$, trans-1,4-cyclohexylene, 1,4-cyclohexenylene, 1-tetrahydropyran-2,5-diyl, 1,3-dioxane-2,5-diyl, 1,4-phenylene, 2-fluoro-1,4-phenylene, 3-fluoro-1,4-phenylene, 2,3-difluoro-1,4-phenylene, 3-fluoropyridine-2,5-diyl, pyrimidine-2,5-diyl and pyridazine-2,5-diyl are preferred, and trans-1,4-cyclohexylene, 1-tetrahydropyran-2,5-diyl, 1,3-dioxane-2,5-diyl, 1,4-phenylene, 2-fluoro-1,4-phenylene, 3-fluoro-1,4-phenylene and 2,3-difluoro-1,4-phenylene are more preferred.

In the compound (a), $Z^1$, $Z^2$, $Z^3$ and $Z^4$ are each independently a single bond or alkylene having 1 to 4 carbons, provided that in the alkylene, arbitrary —CH$_2$— may be replaced by —O— or —CO—, arbitrary —CH$_2$CH$_2$— may be replaced by —CH═CH— or —C≡C—, and arbitrary hydrogen may be replaced by a halogen. Preferred examples of $Z^1$, $Z^2$, $Z^3$ and $Z^4$ include a single bond, —(CH$_2$)$_2$—, —CH$_2$O—, —OCH$_2$—, —CF$_2$O—, —OCF$_2$—, —COO—, —COO—, —CH$_2$CO—, —COCH$_2$—, —CH═CH—, —CF═CF—, —C≡C—, —(CH$_2$)$_4$—, —(CH$_2$)$_2$COO—, —OCO(CH$_2$)$_2$—, —(CH$_2$)$_3$O—, —O(CH$_2$)$_3$—, —(CH$_2$)$_2$CF$_2$O— and —OCF$_2$(CH$_2$)$_2$—. As the configuration of —CH═CH— and —CF═CF—, trans is preferable to cis.

Particularly preferred examples of $Z^1$, $Z^2$, $Z^3$ and $Z^4$ include a single bond, —(CH$_2$)$_2$—, —CH$_2$O—, —OCH$_2$—, —CF$_2$O—, —OCF$_2$—, —COO— and —COO—.

In the compound (a), l, m, n and o are each independently 0 or 1.

In the compound (a), ring L is ring L1 or ring L2:

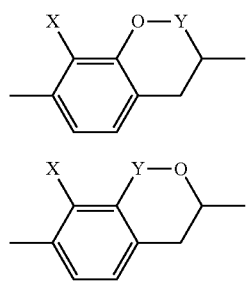

In ring L1 and ring L2, X is hydrogen or halogen; and Y is —C(═O)— or —CF$_2$—. As rings L1 and L2, a ring wherein X is hydrogen or fluorine is preferred, and a ring wherein X is fluorine is more preferred.

The compound (a) can be adjusted in such characteristics as optical anisotropy (Δn), dielectric anisotropy (Δ∈) and so forth by appropriately selecting the end groups Ra and Rb, the rings $A^1$, $A^2$, $A^3$ and $A^4$, and the bonding groups $Z^1$, $Z^2$, $Z^3$ and $Z^4$, within the aforementioned ranges.

Among the compound (a), compounds represented by general formulas (a-1) to (a-7) shown below (hereinafter, referred to as compounds (a-1) to (a-7) in some cases) are preferred.

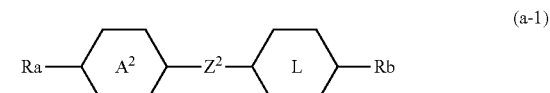

(a-1)

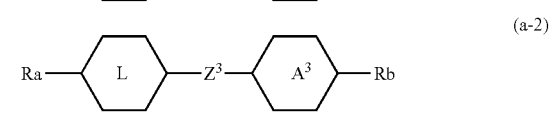

(a-2)

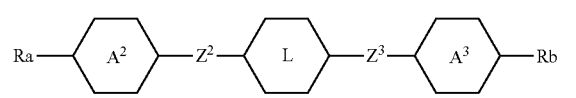

(a-3)

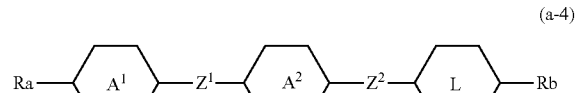

(a-4)

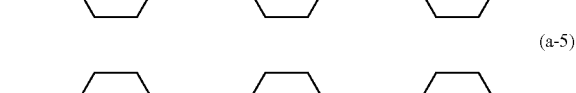

(a-5)

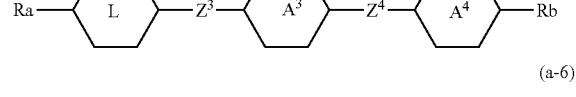

(a-6)

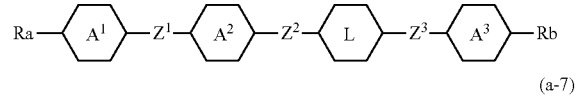

(a-7)

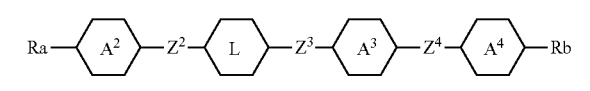

In formulas (a-1) to (a-7), Ra, Rb, ring $A^1$, ring $A^2$, ring $A^3$, ring $A^4$, $Z^1$, $Z^2$, $Z^3$, $Z^4$ and ring L have the same meaning as in general formula (a).

Among the compounds (a-1) to (a-7), compounds represented by general formulas (a-1-1) to (a-1-32), (a-2-1) to (a-2-10), (a-3-1) to (a-3-16), (a-4-1) to (a-4-15), (a-5-1) to (a-5-14), (a-6-1) to (a-6-8) and (a-7-1) to (a-7-8) shown below (hereinafter, referred to as compounds (a-1-1) to (a-1-32), (a-2-1) to (a-2-10), (a-3-1) to (a-3-16), (a-4-1) to (a-4-15), (a-5-1) to (a-5-14), (a-6-1) to (a-6-8) and (a-7-1) to (a-7-8) in some cases) are preferred.

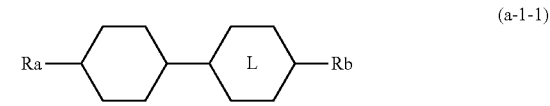

(a-1-1)

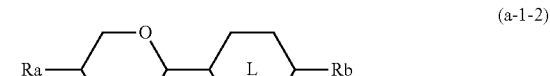

(a-1-2)

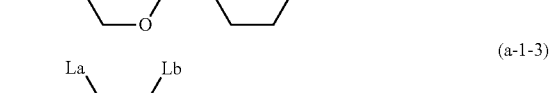

(a-1-3)

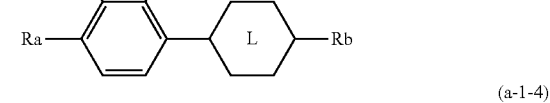

(a-1-4)

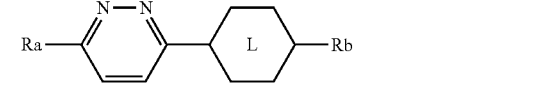

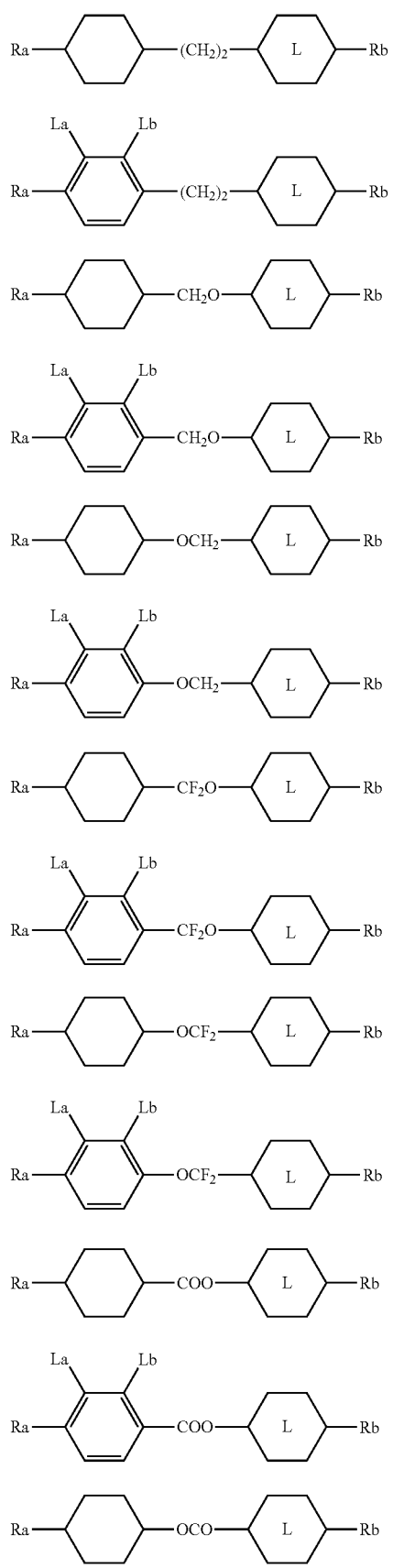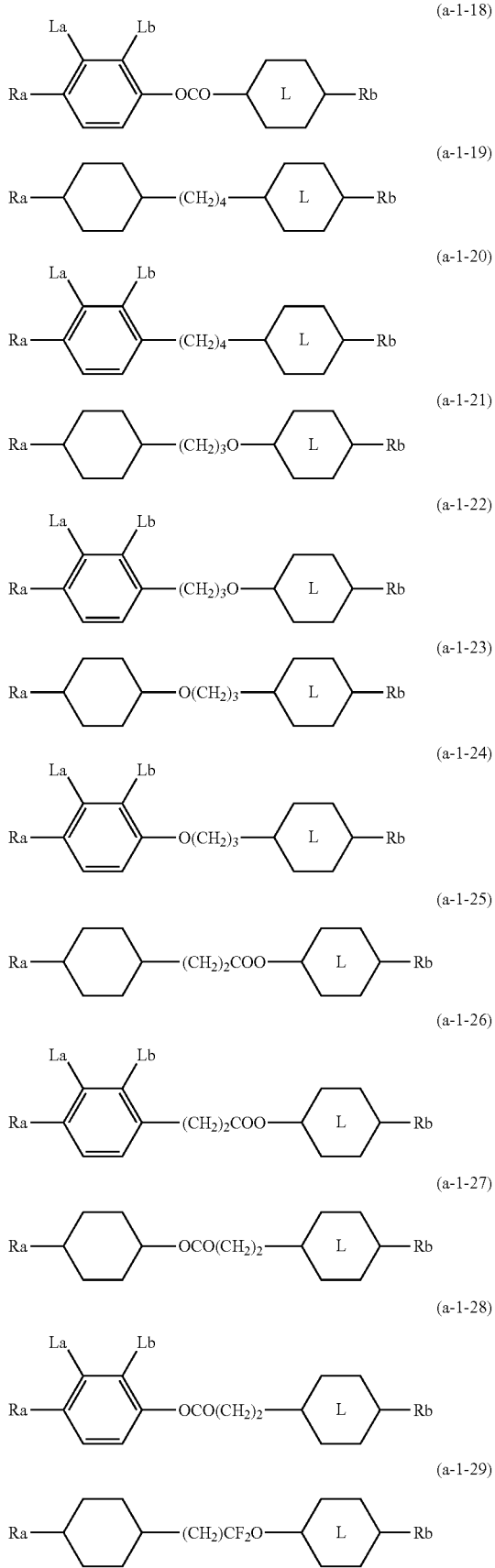

(a-1-30) 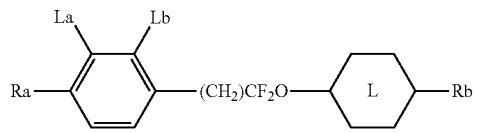
(a-1-31) 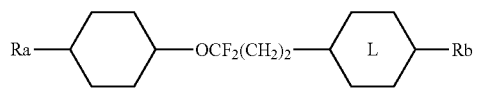
(a-1-32) 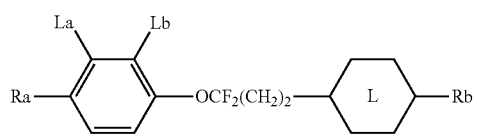
(a-2-1) 
(a-2-2) 
(a-2-3) 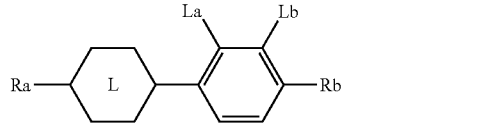
(a-2-4) 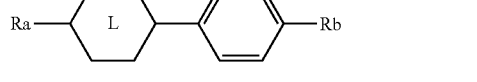
(a-2-5) 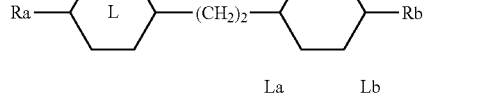
(a-2-6) 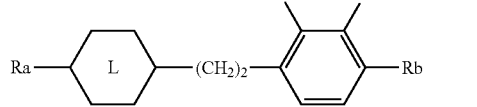
(a-2-7) 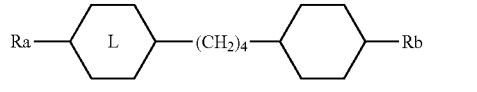
(a-2-8) 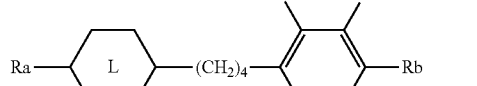
(a-2-9) 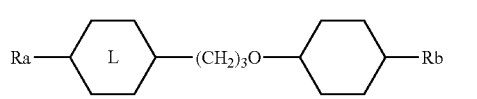
(a-2-10) 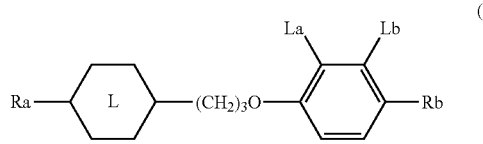
(a-3-1) 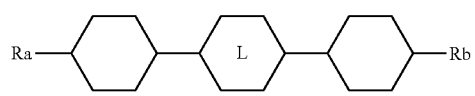
(a-3-2) 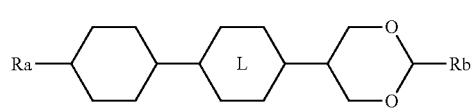
(a-3-3) 
(a-3-4) 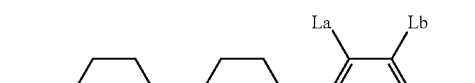
(a-3-5) 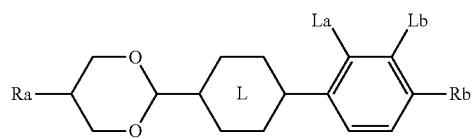
(a-3-6) 
(a-3-7) 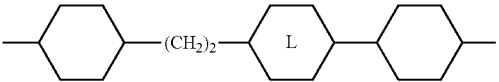
(a-3-8) 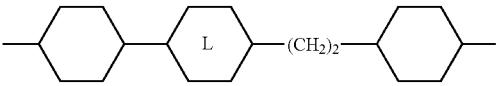
(a-3-9) 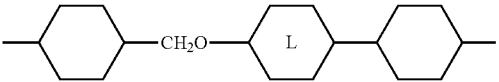
(a-3-10) 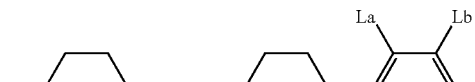
(a-3-11) 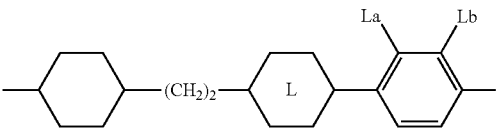

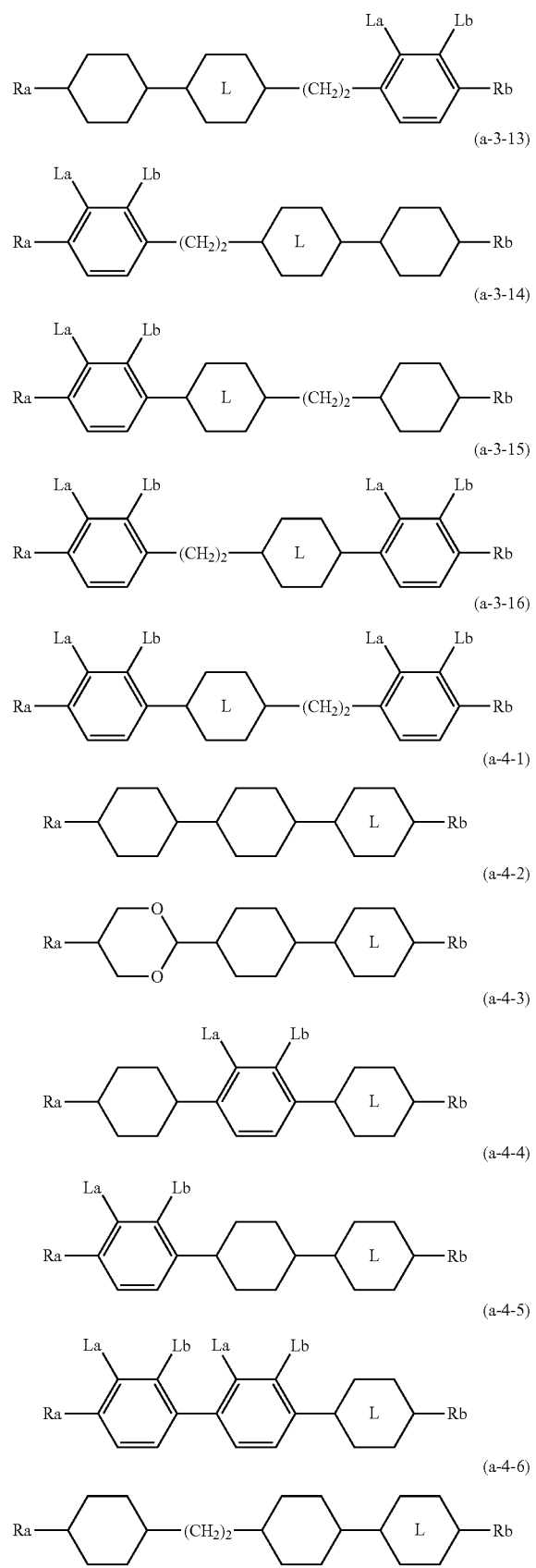
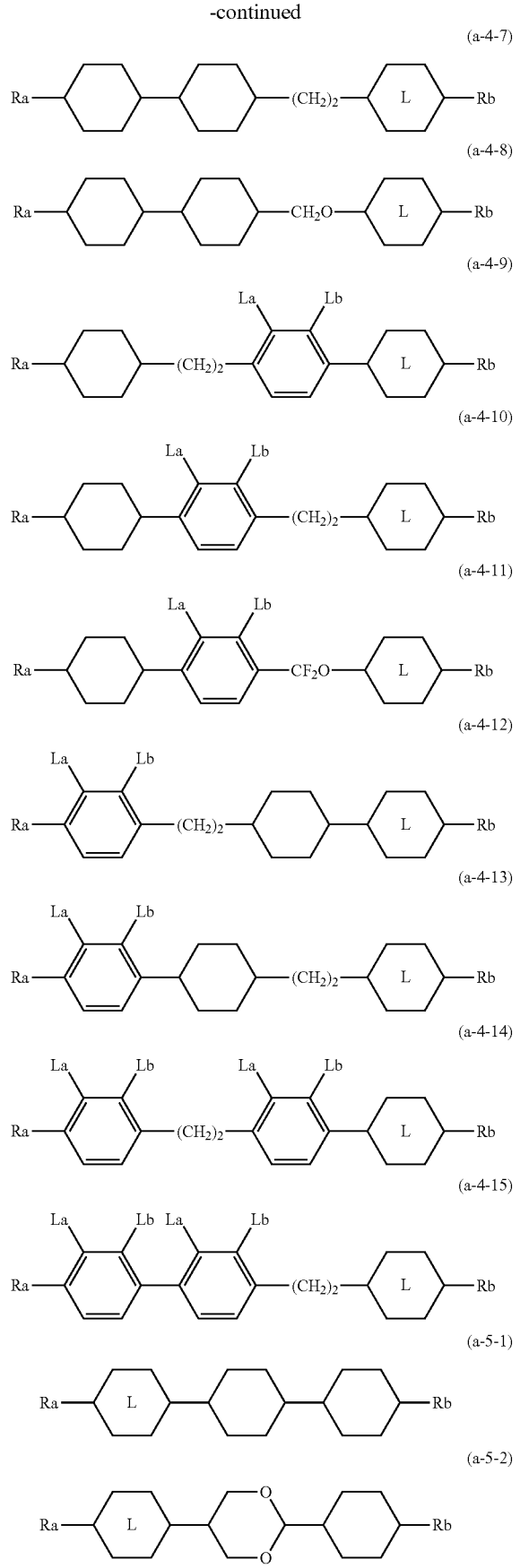

(a-5-3) 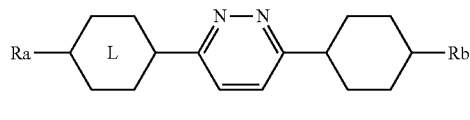
(a-5-4) 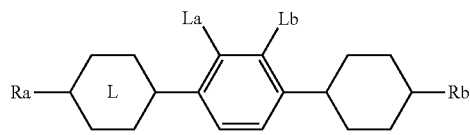
(a-5-5) 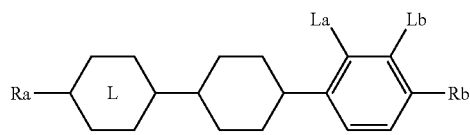
(a-5-6) 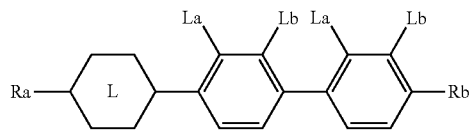
(a-5-7) 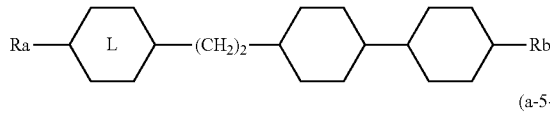
(a-5-8) 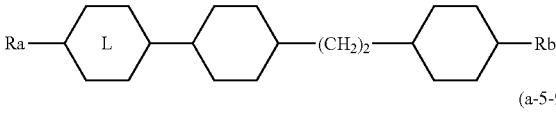
(a-5-9) 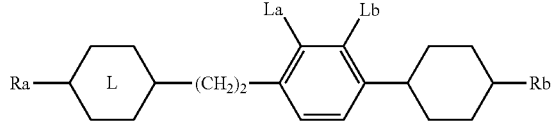
(a-5-10) 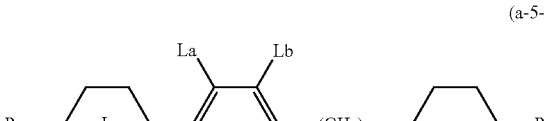
(a-5-11) 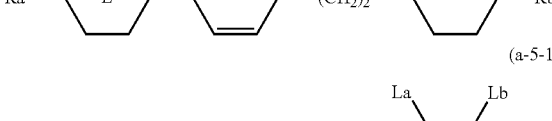
(a-5-12) 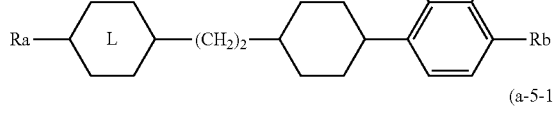
(a-5-13) 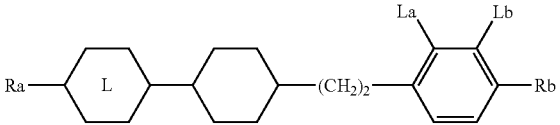
(a-5-14) 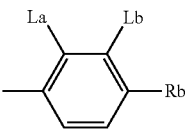
(a-6-1) 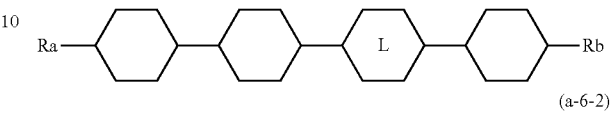
(a-6-2) 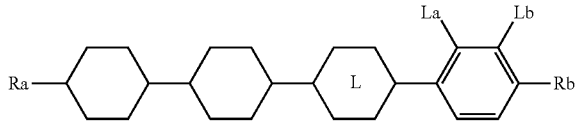
(a-6-3) 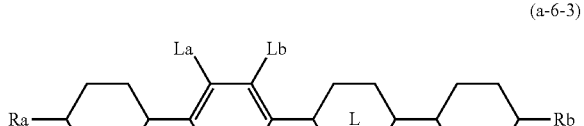
(a-6-4) 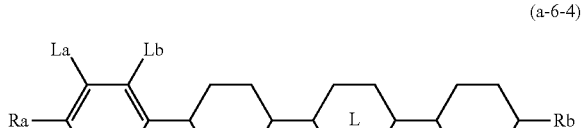
(a-6-5) 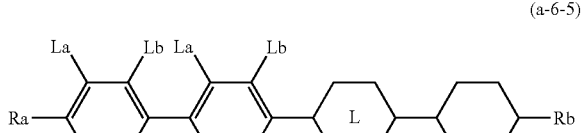
(a-6-6) 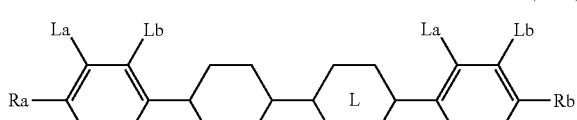
(a-6-7) 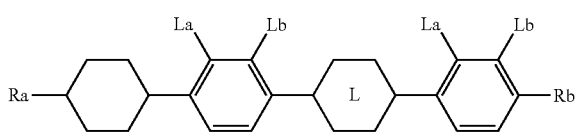
(a-6-8) 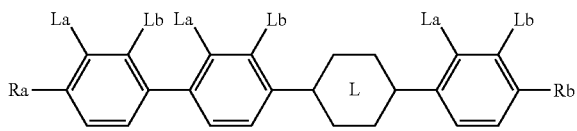
(a-7-1) 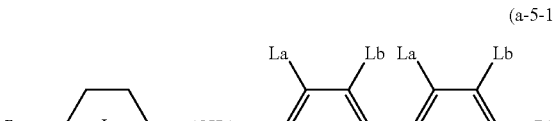
(a-7-2) 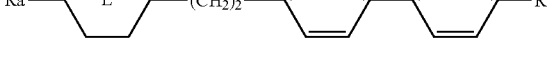
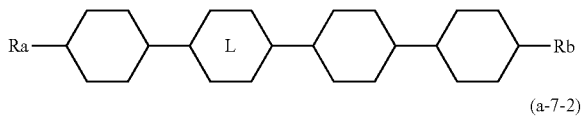

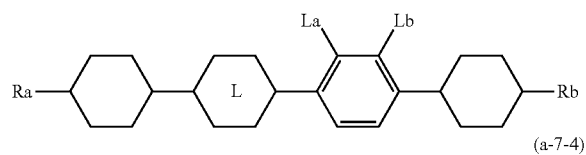
(a-7-3)

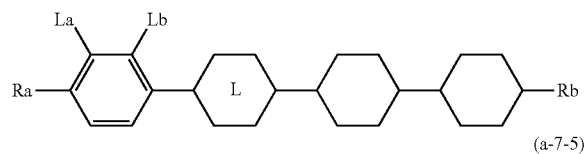
(a-7-4)

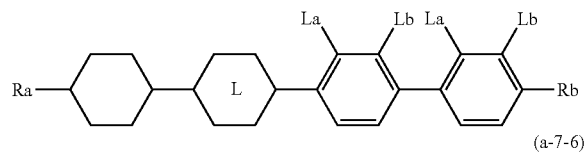
(a-7-5)

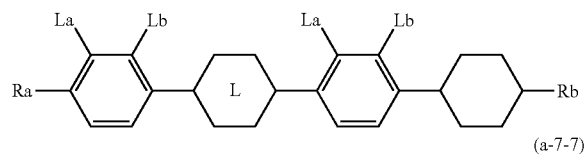
(a-7-6)

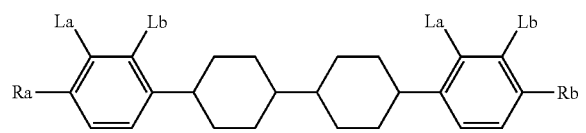
(a-7-7)

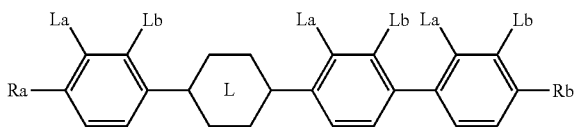
(a-7-8)

In the above formulas, the definitions of Ra and Rb are the same as those in formula (a), and La and Lb are each independently hydrogen or a halogen.

Synthesis of Compound (a)

The liquid crystal compounds (a) can be synthesized by appropriately combining synthesis methods of synthetic organic chemistry. Examples of a method for introducing the target end groups, rings and bonding groups into starting materials are disclosed in such literatures as Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Kouza) (Maruzen, Inc.), and so forth.

Formation of Bonding Groups $Z^1$, $Z^2$, $Z^3$ and $Z^4$

One example of a method for forming the bonding groups $Z^1$, $Z^2$, $Z^3$ and $Z^4$ is described. In the scheme, $MSG^1$ and $MSG^2$ are a monovalent organic group. Plural compounds of $MSG^1$ (or $MSG^2$) used in the scheme may be the same as each other or different from each other. The compounds (a-A) to (a-I) correspond to the compound (a).

$$\text{Hal}-MSG^2 \xrightarrow{Mg} \xrightarrow[\text{(14)}]{MSG^1-\bigcirc=O} \xrightarrow[-H_2O]{H_3O^+} MSG^1-\bigcirc-MSG^2$$
(13)                                                        (15)

(Hal = Br, I)

$$\text{Hal}-MSG^2 \xrightarrow{Mg} \xrightarrow[\text{(16)}]{MSG^1-CHO} \xrightarrow[-H_2O]{H_3O^+} MSG^1-CH=CH-MSG^2$$
(13)                                                       (a-A)

(Hal = Br, I)

$$\text{Hal}-MSG^2 \xrightarrow{Mg} \xrightarrow[\text{(17)}]{MSG^1-CH_2-CHO} \xrightarrow[-H_2O]{H_3O^+} MSG^1-CH_2-CH=CH-MSG^2$$
(13)                                                      (a-B)

(Hal = Br, I)

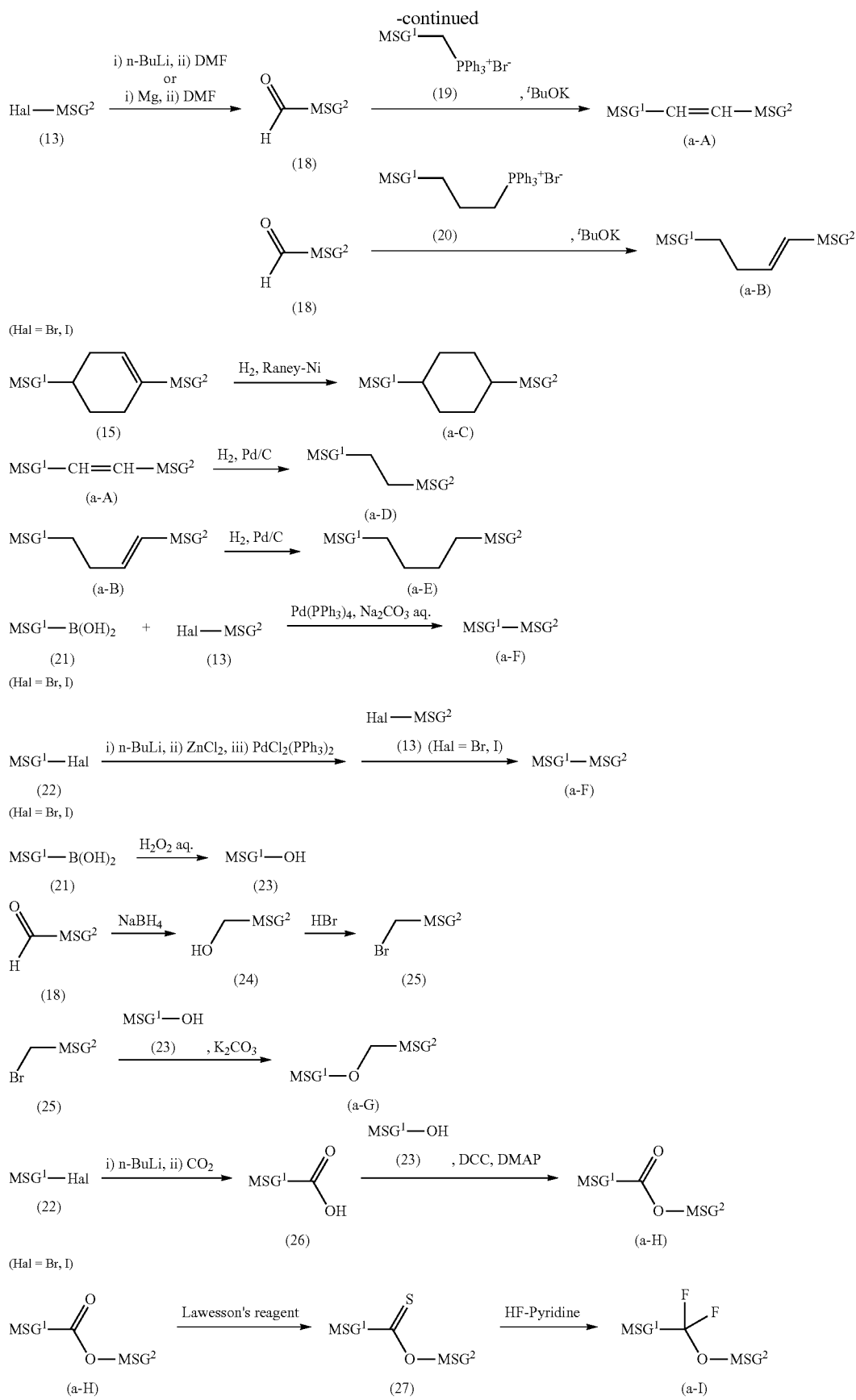

(I) Formation of Double Bond 1

An organic halogen compound (13) having a monovalent organic group $MSG^2$ and magnesium are reacted with each other to prepare a Grignard reagent. The Grignard reagent thus prepared and an aldehyde derivative (16) or (17) are reacted with each other to prepare a corresponding alcohol derivative. Subsequently, the resulting alcohol derivative is subjected to dehydration by using an acid catalyst, such as p-toluenesulfonic acid, to synthesize a corresponding compound (a-A) or (a-B) having a double bond.

(II) Formation of Double Bond 2

A compound obtained by treating an organic halogen compound (13) with n-butyllithium or magnesium is reacted with a formamide, such as N,N-dimethylformamide (DMF), to prepare an aldehyde (18). Subsequently, the resulting aldehyde (18) is reacted with a phosphylide obtained by treating a phosphonium salt (19) or (20) with a base, such as potassium t-butoxide, to synthesize a corresponding compound (a-A) or (a-B) having a double bond. In the aforementioned reactions, a cis compound may be formed depending on reaction conditions, and thus in the case where a trans compound is necessary, the cis compound may be isomerized to the trans compound by a known method.

(III) Formation of Single Bond 1

An organic halogen compound (13) and magnesium are reacted with each other to prepare a Grignard reagent. The Grignard reagent thus prepared and a cyclohexanone derivative (14) are reacted with each other to prepare a corresponding alcohol derivative. Subsequently, the resulting alcohol derivative is subjected to dehydration by using an acid catalyst, such as p-toluenesulfonic acid, to synthesize a corresponding compound (15) having a double bond. The resulting compound (15) is subjected to hydrogenation in the presence of a catalyst, such as Raney nickel, to synthesize a compound (a-C). The cyclohexanone derivative (14) can be synthesized according, for example, to a method disclosed in JP S59-7122 A/1984.

(IV) Formation of Single Bond 2

A dihydroxyborane derivative (21) and an organic halogen compound (13) are reacted with each other in the presence of, for example, a catalyst containing a carbonate salt aqueous solution and tetrakis(triphenylphosphine) palladium (Pd (PPh$_3$)$_4$) to synthesize a compound (a-F).

In the alternative, an organic halogen compound (22) having a monovalent organic group $MSG^2$ is reacted with n-butyllithium and then reacted with zinc chloride, and the resulting compound is then reacted with a compound (13) in the presence of, for example, bistriphenylphosphine dichloropalladium (Pd(PPh$_3$)$_2$Cl$_2$) as a catalyst to synthesize a compound (a-F).

(V) Formation of —(CH$_2$)$_2$—

The compound (a-A) is hydrogenated in the presence of a catalyst, such as carbon-supported palladium (Pd/C), to synthesize a compound (a-D).

(VI) Formation of —(CH$_2$)$_4$—

The compound (a-B) is hydrogenated in the presence of a catalyst, such as carbon-supported palladium (Pd/C), to synthesize a compound (a-E).

(VII) Formation of —CH$_2$O— and —OCH$_2$—

A dihydroxyborane derivative (21) is oxidized with an oxidizing agent, such as hydrogen peroxide, to prepare an alcohol derivative (23). Separately, an aldehyde derivative (18) is reduced with a reducing agent, such as sodium borohydride, to prepare a compound (24). The resulting compound (24) is halogenated with hydrobromic acid or the like to prepare an organic halogen compound (25). The resulting compound (23) and the compound (25) are reacted with each other in the presence of potassium carbonate or the like to synthesize a compound (a-G).

(VIII) Formation of —COO— and —OCO—

A compound (22) is reacted with n-butyllithium to derive a lithiated compound, which is then reacted with carbon dioxide to prepare a carboxylic acid (26). The carboxylic acid (26) and an alcohol (23) or a phenol, which is synthesized by a known method, are subjected to dehydration condensation to synthesize a compound (a-H) having —COO—. A compound having —COO— can also be synthesized in the same manner.

(IX) Formation of —CF$_2$O— and —OCF$_2$—

A compound (a-H) is treated with sulfurizing agent, such as Lawesson's reagent, to obtain a compound (27). The compound (27) is fluorinated with a hydrogen fluoride pyridine complex (M. Kuroboshi, et al., Chem. Lett., 827 (1992)) or (diethylamino) sulfate trifluoride (William. H. Bunnelle, et al., J. Org. Chem., 55, 768 (1990)) to synthesize a compound (a-I) having —CF$_2$O—. A compound having —OCF$_2$— can also be synthesized in the same manner.

A compound (a-J), which is the compound (a) of the invention, wherein X in ring L1 is hydrogen or fluorine, and Y is —C(=O)—, can be synthesized, for example, by the following manner.

A hydroxyl group of a compound (28) is protected with a methoxymethyl group or the like to prepare a compound (29) (wherein $P^1$ is a protective group, see Protective Groups in Organic Synthesis, Jhon Wiley & Sons, Inc. and so forth), which is reacted with a Grignard reagent (30) in the presence of a catalyst, such as (1,1'-bis(diphenylphosphino)ferrocene) dichloropalladium (hereinafter referred to as Pd(dppf)) or (1,2-bis(diphenylphosphino)ethane) dichloropalladium (hereinafter referred to as Pd(dppe)), to prepare a compound (31). The compound (31) is then formylated according to the method disclosed in Yakugakuzasshi, 105, 11 (1985) to prepare a compound (32).

The compound (32) and a compound (33) are subjected to esterification according to the method disclosed in Syn. Commun., 13, (6), 471 (1983) and Synthesis, 1061 (1986) to prepare a compound (34). The compound (34) is then heated under refluxing in the presence of triethylamine to prepare a coumarin compound (35) through intramolecular aldol reaction. Finally, the compound (35) is hydrogenated in the presence of a catalytic amount of palladium hydroxide to prepare a target compound (a-J).

A compound (a-K), which is the compound (a) of the invention, wherein X in ring L1 is hydrogen or fluorine, and Y is —CF$_2$—, can be synthesized, for example, by the following manner.

The compound (a-J) is reacted with a Lawesson's reagent or the like to prepare a compound (36), which is then reacted with a fluorinating agent, such as a hydrogen fluoride pyridine complex or (diethylamino)sulfate trifluoride, to prepare a target compound (a-K).

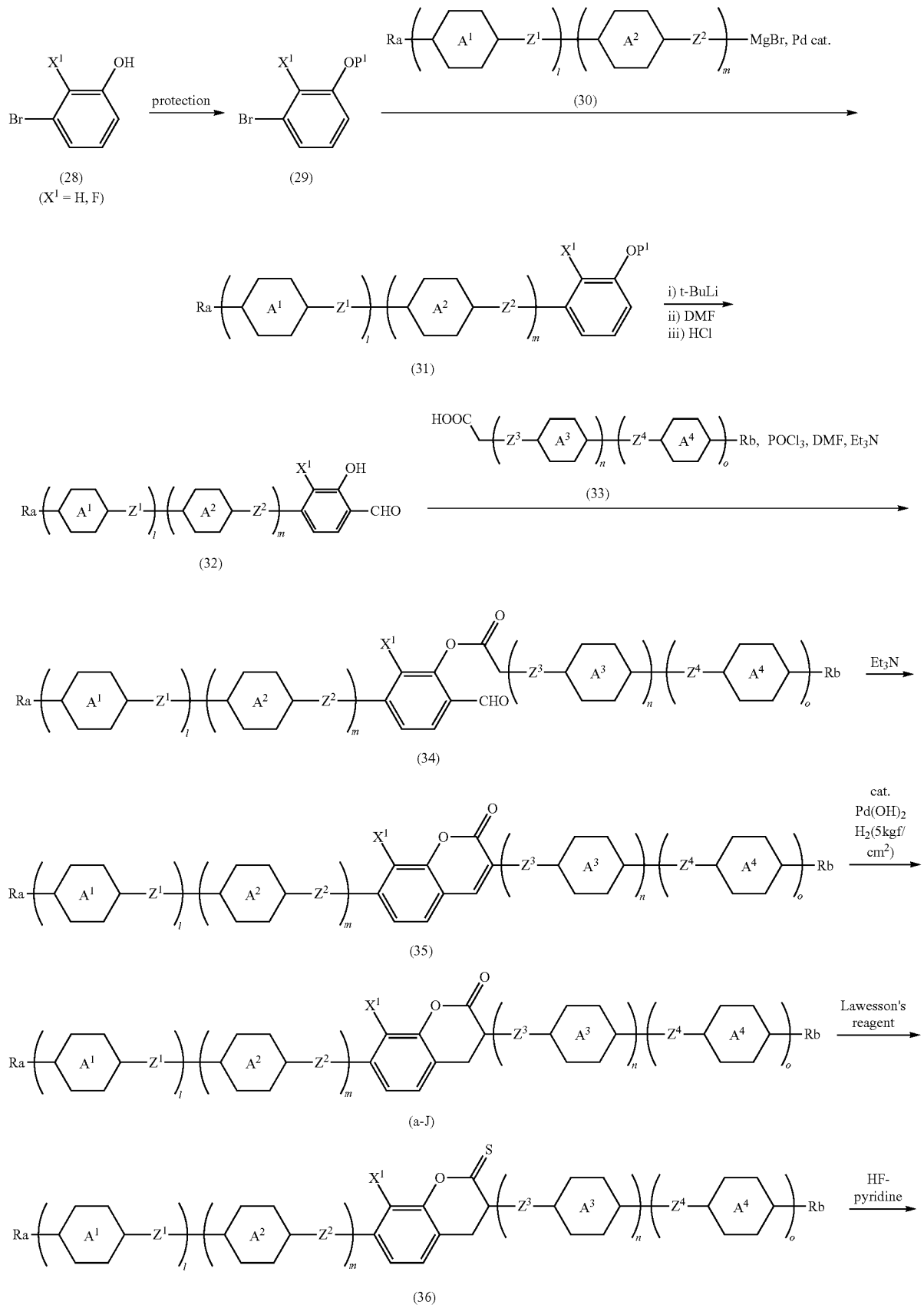

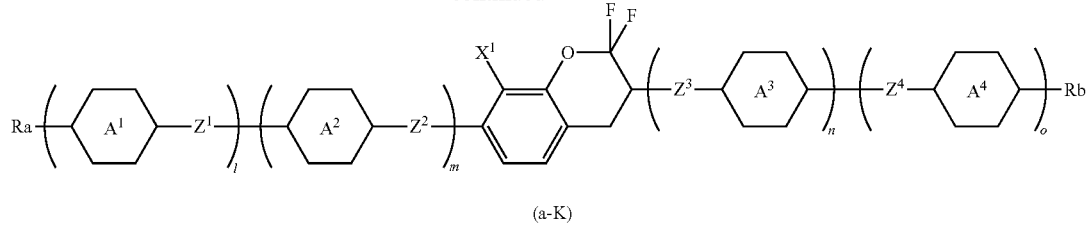

(a-K)

A compound (a-K) can also be synthesized in the following manner.

A compound (31) is formylated to prepare a compound (37), which is derived to a compound (38) through Wittig reaction using methoxymethyltriphenylphosphine chloride and an acid treatment. The compound (38) is then reacted with a Grignard reagent (39) to derive a compound (40), and then a compound (41) is obtained from the compound (40) through Jones oxidation. The compound (41) is converted to a compound (42) through Wittig reaction using dibromodifluoromethane, and the compound (42) is reacted with bromine to prepare a compound (43). Finally, the compound (43) is subjected to hydrogen reduction in the presence of a carbon-palladium catalyst and a base, such as potassium carbonate, to prepare a target compound (a-K).

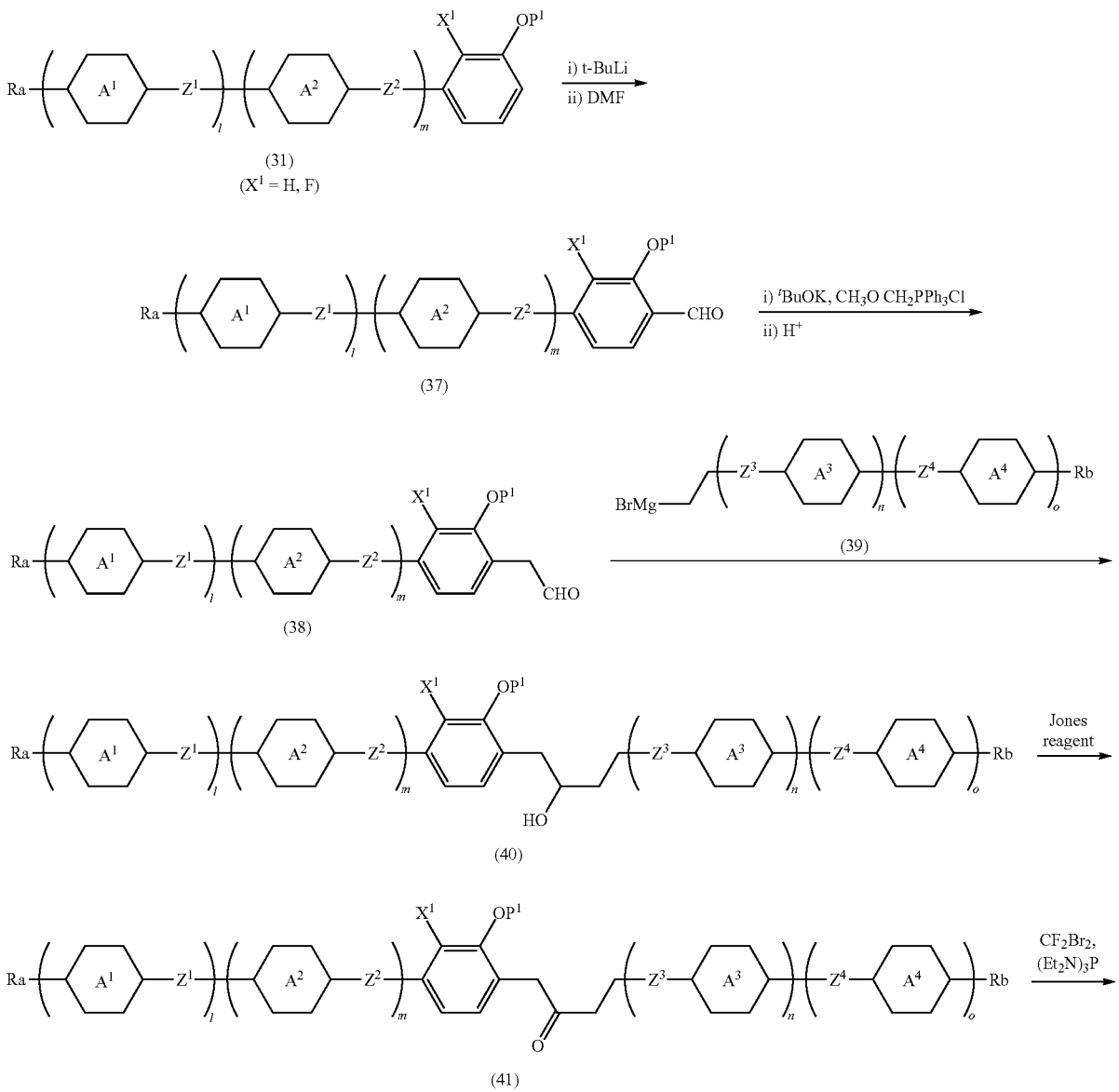

-continued

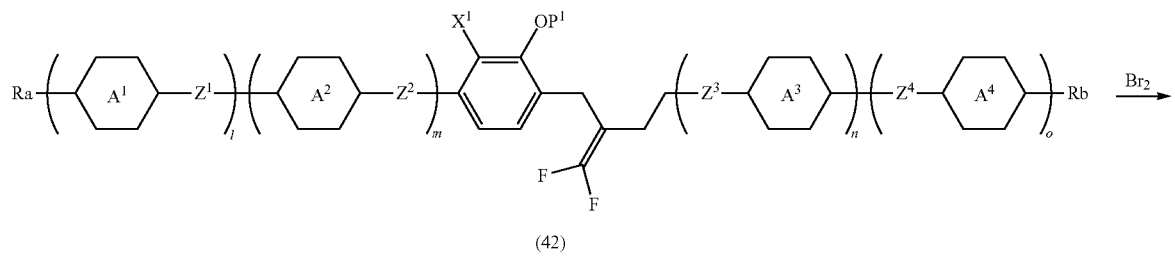

(42)

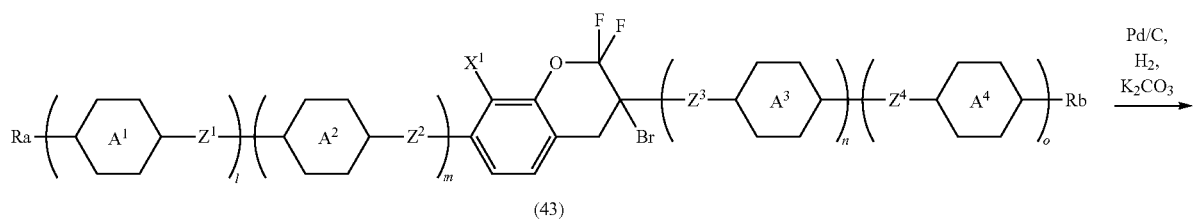

(43)

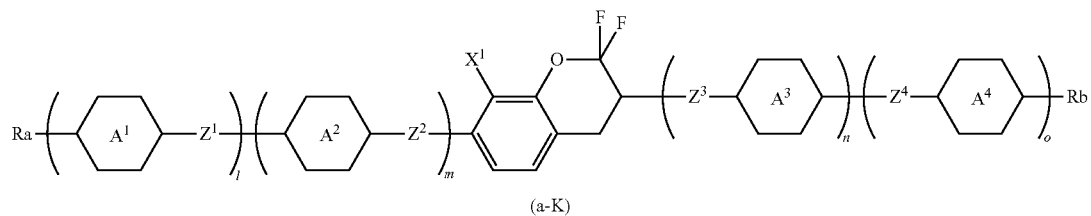

(a-K)

A compound (a-L), which is the compound (a) of the invention, wherein X in ring L2 is hydrogen or fluorine, and Y is —C(=O)—, can be synthesized, for example, by the following manner.

An amino group of a compound (44) is protected with a t-butoxycarbonyl group, a benzyloxycarbonyl group or the like (wherein $P^2$ is a protective group) to prepare a compound (45), which is then reacted with a Grignard reagent (30) in the presence of a catalyst, such as Pd(dppf) or Pd(dppe), to prepare a compound (46). The compound (46) is deprotected and converted to a diazonium salt through reaction with hydrochloric acid and sodium nitrite, followed by iodination, to prepare a compound (48). The compound (48) is then treated with n-BuLi and reacted with carbon dioxide to convert to a carboxylic acid (49). Separately, a compound is reacted with a Grignard reagent (30) in the presence of a catalyst, such as Pd(dppf) or Pd(dppe), to prepare a compound (51). The compound (51) is then treated with s-BuLi and reacted with carbon dioxide to derive a carboxylic acid (52).

The compound (49) and the compound (52) are then converted to a compound (a-L) by the method disclosed in J. Org. Chem., 57, 6716 (1992). Specifically, the compounds (49) and (52) are treated with lithium diisopropylamide and then reacted with trimethylsilyl chloride to prepare a compound (53), which is then converted to a compound (54) through reaction with thionyl chloride. Subsequently, the compound (54) is reacted with a compound (55) in the presence of cesium fluoride to prepare a target compound (a-L).

A compound (a-M), which is the compound (a) of the invention, wherein X in ring L2 is hydrogen or fluorine, and Y is —$CF_2$—, can be synthesized, for example, by the following manner.

The compound (a-L) is reacted with a Lawesson's reagent or the like to prepare a compound (56), which is then reacted with a fluorinating agent, such as a hydrogen fluoride pyridine complex or (diethylamino)sulfate trifluoride, to prepare a target compound (a-M).

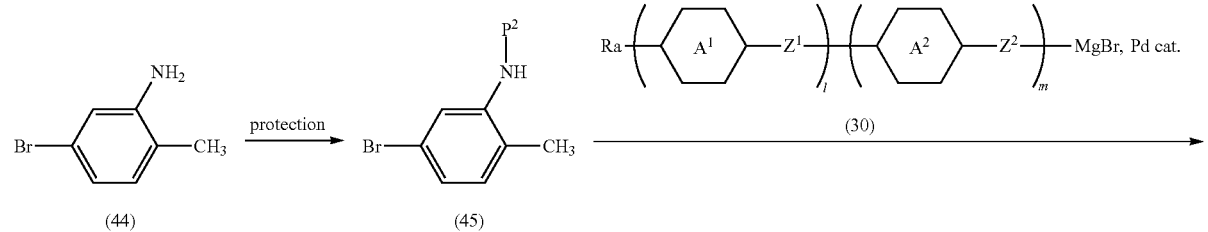

-continued
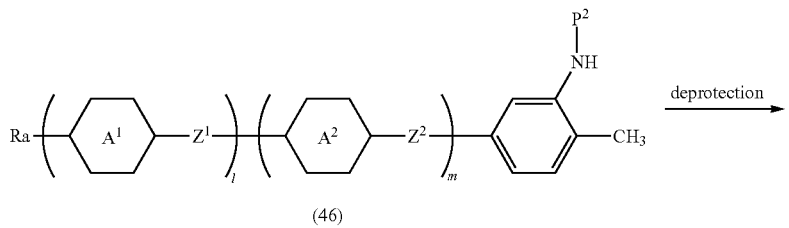
(46)
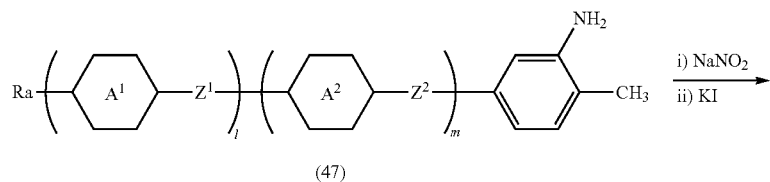
(47)
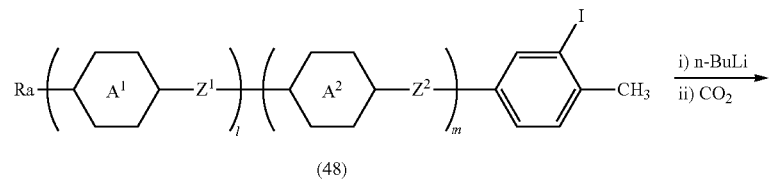
(48)
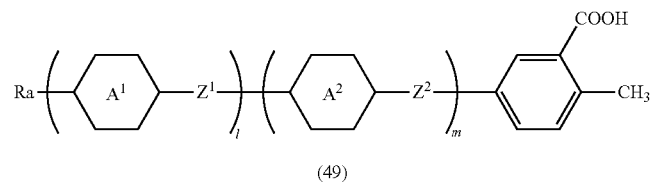
(49)
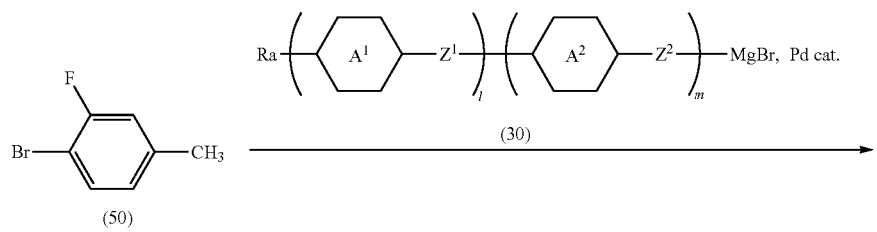
(50)
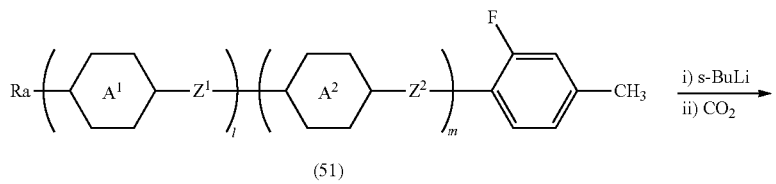
(51)
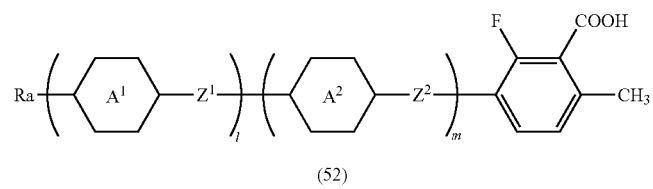
(52)
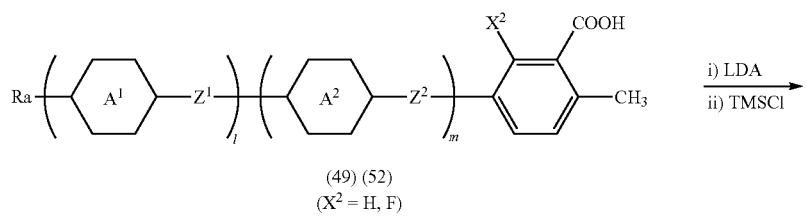
(49) (52)
($X^2$ = H, F)

-continued

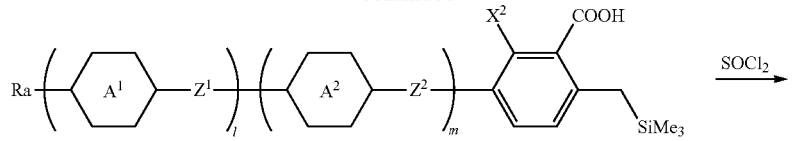
(53)

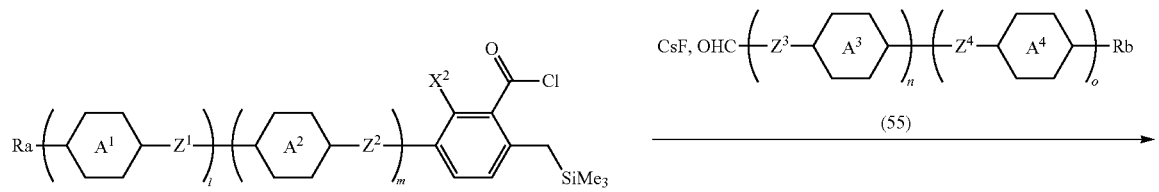
(54)

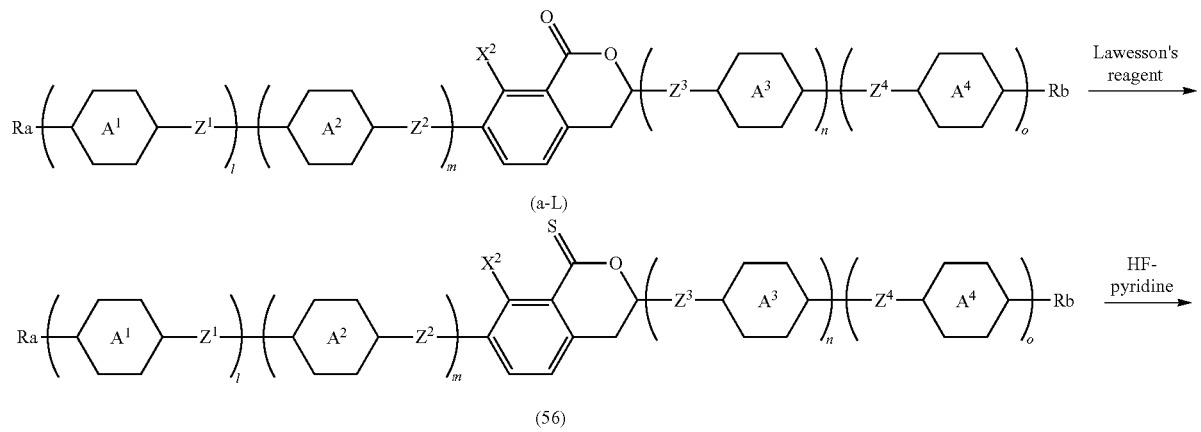
(a-L)

(56)

(a-M)

A compound (a-L) can be synthesized, for example, by the following manner.

A compound (57) is reacted with a Grignard reagent (30) in the presence of a catalyst, such as Pd(dppf) or Pd(dppe), to prepare a compound (58). The compound (58) is subjected to DIBAL reduction to prepare a compound (59), which is then converted to a compound (60) through Wittig reaction using methoxymethyltriphenylphosphine chloride and an acid treatment. The compound (60) is then reacted with a Grignard reagent (61) to derive a compound (62), and then a hydroxyl group of the compound (62) is protected with a methoxymethyl group or the like to prepare a compound (63) (wherein $P^3$ is a protective group). The compound (63) is then treated with s-BuLi and reacted with carbon dioxide to prepare a carboxylic acid (64), which is finally treated with an acid to prepare a target compound (a-L).

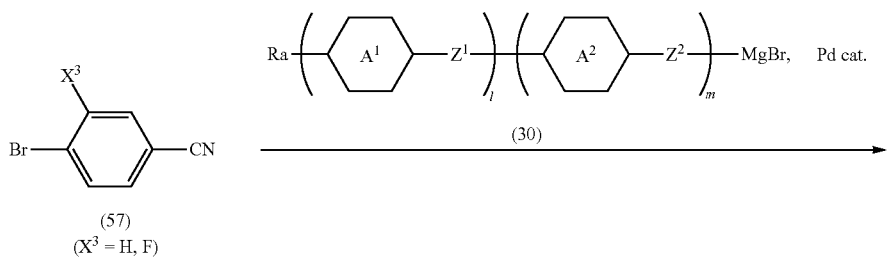
(57)
($X^3$ = H, F)

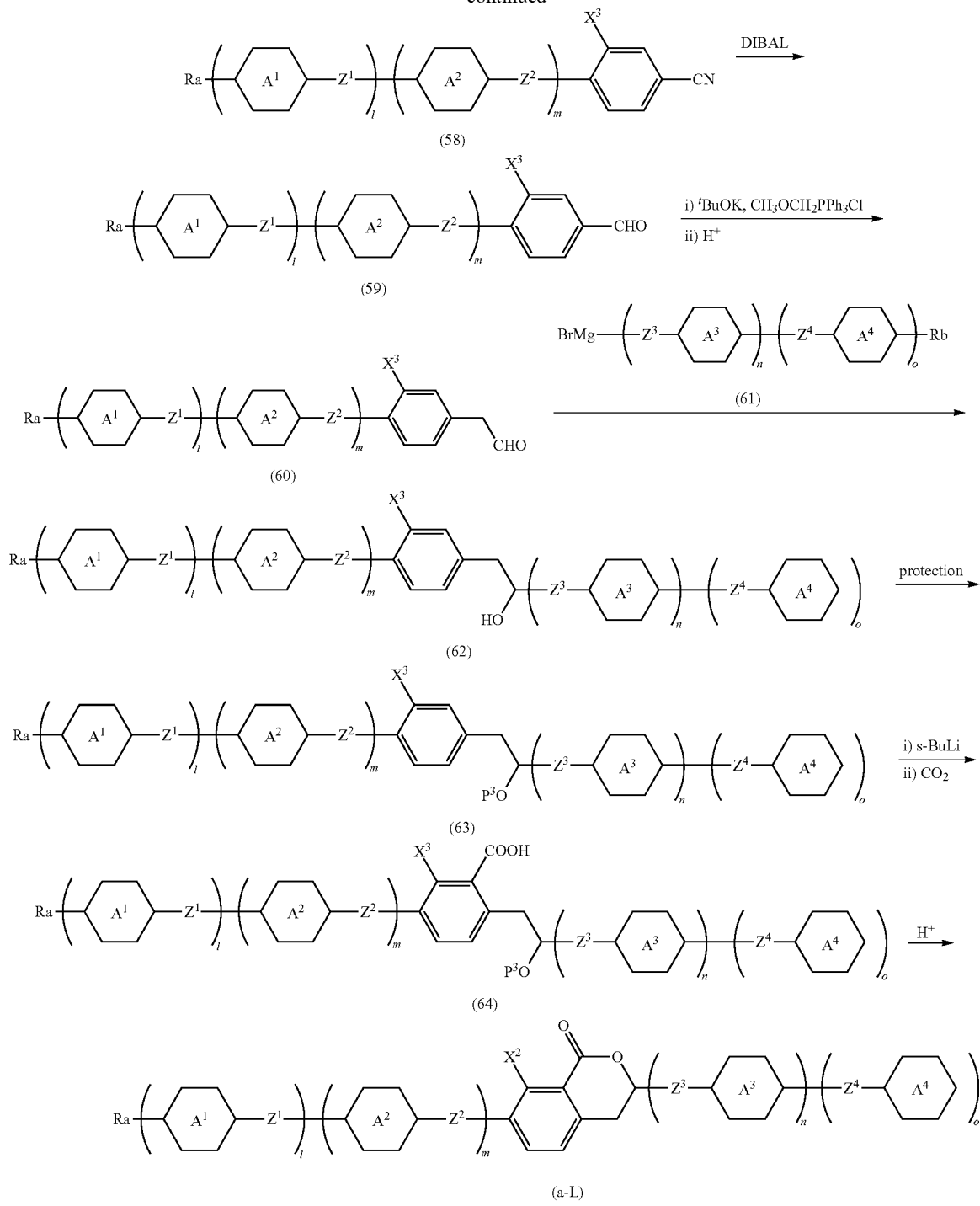

The liquid crystal composition of the invention will be described below. The liquid crystal composition of the invention contains at least one compound selected from the group consisting of the compounds represented by formula (a). The liquid crystal composition may contain two or more of the compounds (a), and may contain only the compounds (a). The content of the compound (a) in the liquid crystal composition of the invention is not particularly limited, and the liquid crystal composition preferably contains the compound (a) in a ratio of from approximately 1% to approximately 99% by weight based on the total weight of the compounds contained in the liquid crystal composition. Upon preparing the liquid crystal composition of the invention, the components may be selected in consideration, for example, of the dielectric anisotropy of the compound (a).

The liquid crystal composition has a low viscosity, a suitable optical anisotropy, a suitable negative dielectric anisotropy, a low threshold voltage, a high maximum temperature of a nematic phase (phase transition temperature from a nematic phase to an isotropic phase), and a low minimum temperature of a nematic phase.

The liquid crystal composition of the invention may contain, in addition to the compound (a), at least one compound selected from the group of compounds represented by formulas (1) to (9) below (hereinafter, referred to as compounds (1) to (9) in some cases).

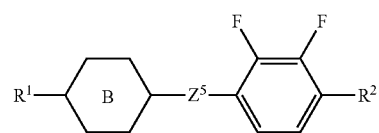
(1)

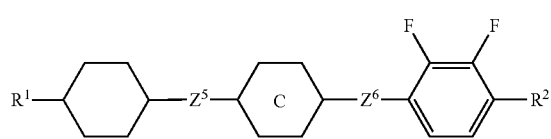
(2)

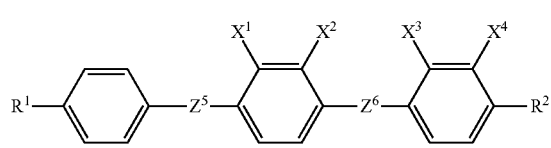
(3)

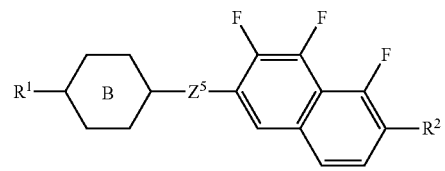
(4)

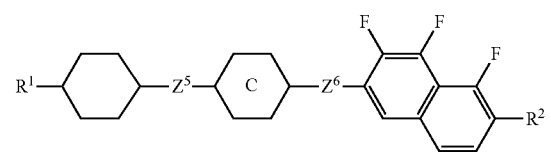
(5)

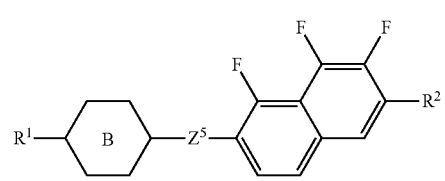
(6)

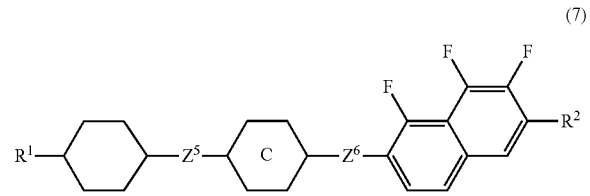
(7)

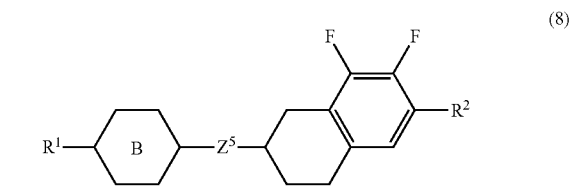
(8)

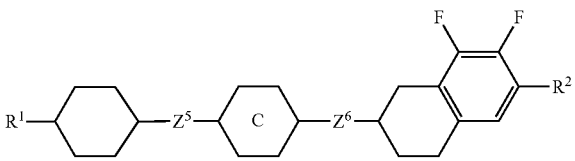
(9)

In formulas (1) to (9), $R^1$ and $R^2$ are each independently alkyl having 1 to 10 carbons, provided that in the alkyl, —$CH_2$— may be replaced by —O—, —$(CH_2)_2$— may be replaced by —CH=CH—, and hydrogen may be replaced by fluorine, and $R^1$ may be fluorine; ring B and ring C are each independently 1,4-cyclohexylene, 1,4-phenylene or decahydro-2,6-naphthylene; $Z^5$ and $Z^6$ are each independently —$(CH_2)_2$—, —COO— or a single bond; and $X^1$, $X^2$, $X^3$ and $X^4$ are each independently hydrogen or fluorine, provided that at least one of $X^1$, $X^2$, $X^3$ and $X^4$ is fluorine.

In the case where the additional compound is a compound represented by formula (1), the liquid crystal composition can have a low viscosity, a small optical anisotropy, and a further low threshold voltage.

In the case where the additional compound is a compound represented by formula (2), the liquid crystal composition can have a high maximum temperature of a nematic phase, a large optical anisotropy, and a further low threshold voltage.

In the case where the additional compound is a compound represented by formula (3), the liquid crystal composition can have a large optical anisotropy and a further low threshold voltage.

In the case where the additional compound is compounds represented by formulas (4) to (7), the liquid crystal composition can have a high maximum temperature of a nematic phase, a large optical anisotropy, and a further low threshold voltage.

In the case where the additional compound is compounds represented by formulas (8) and (9), the liquid crystal composition can have a high maximum temperature of a nematic phase and a further low threshold voltage.

The content of the compounds (1) to (9) in the liquid crystal composition of the invention is not particularly limited, and in order to prevent the absolute value of the negative dielectric anisotropy from being decreased, the liquid crystal composition preferably contains the compounds (1) to (9) in a ratio of approximately 10% by weight or more, and more preferably from approximately 40% to approximately 90% by weight, based on the total weight of the liquid crystal compounds contained in the liquid crystal composition.

The liquid crystal composition of the invention preferably contain, in addition to the compounds (a-1) to (a-6), at least one compound selected from the group of compounds represented by formulas (10) to (12) below.

(10)

$$R^3-\boxed{D}-Z^7-\boxed{E}-Z^8-R^4$$

(11)

$$R^3-\boxed{D}-Z^7-\boxed{E}-Z^8-\boxed{F}-R^4$$

-continued

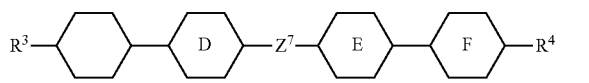
(12)

In formulas (10) to (12), $R^3$ and $R^4$ are each independently alkyl having 1 to 10 carbons, provided that in the alkyl, —CH$_2$— may be replaced by —O—, —(CH$_2$)$_2$— may be replaced by —CH=CH—, and hydrogen may be replaced by fluorine; ring D, ring E and ring F are each independently 1,4-cyclohexylene, pyrimidine-2,5-diyl, or 1,4-phenylene, arbitrary hydrogen of which may be replaced by fluorine; and $Z^7$ and $Z^8$ are each independently —C≡C—, —COO—, —(CH$_2$)$_2$—, —CH=CH— or a single bond.

In the case where the additional compound is a compound represented by formula (10), the liquid crystal composition can have a low viscosity and an optical anisotropy in a suitable range, preferably from approximately 0.010 to approximately 3.000.

In the case where the additional compound is compounds represented by formulas (11) and (12), the liquid crystal composition can have a high maximum temperature of a nematic phase and an optical anisotropy in a suitable range, preferably from approximately 0.010 to approximately 3.000.

The content of the compounds (10) to (12) in the liquid crystal composition of the invention is not particularly limited, and in order to decrease the viscosity, the liquid crystal composition preferably contains a large amount of the compounds. However, there is a tendency that the threshold voltage of the liquid crystal composition is increased when the content of the compounds (10) to (12) is increased, and therefore, in the case where the liquid crystal composition of the invention is used in a liquid crystal device of a VA mode, the content of the compounds (10) to (12) is preferably approximately 70% by weight or less, and more preferably approximately 60% by weight or less, based on the total weight of the liquid crystal compounds contained in the liquid crystal composition.

The liquid crystal composition of the invention may contain, in addition to the compound (a), at least one compound selected from the group of compounds represented by formulas (1), (2), (3), (4), (5), (6), (7), (8) and (9) and at least one compound selected from the group of compounds represented by formulas (10), (11) and (12).

In the case where the liquid crystal composition of the invention has the aforementioned formulation, the composition has a low viscosity, a large negative dielectric anisotropy, a low threshold voltage and a wide temperature range of a liquid crystal phase.

Preferred examples of the compounds (1) to (12) include compounds represented by formulas (1-1) to (1-6), (2-1) to (2-6), (3-1) to (3-5), (4-1), (5-1) and (5-2), (6-1), (7-1) and (7-2), (8-1), (9-1) and (9-2), (10-1) to (10-11), (11-1) to (11-23), and (12-1) to (12-6). In these compounds, $R^1$, $R^2$, $R^3$ and $R^4$ have the same meanings as in the compounds (1) to (9).

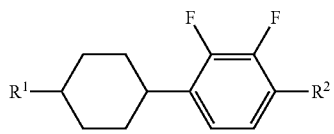
(1-1)

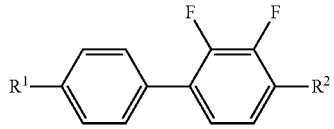
(1-2)

(1-3)
(1-4)
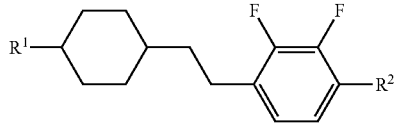

(1-5)
(1-6)
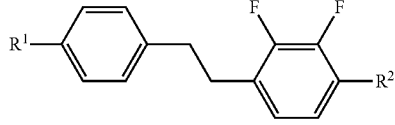

(2-1)
(2-2)
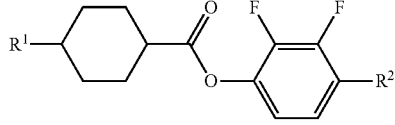

(2-3)
(2-4)
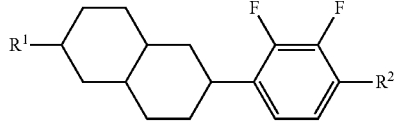

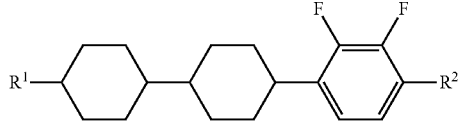

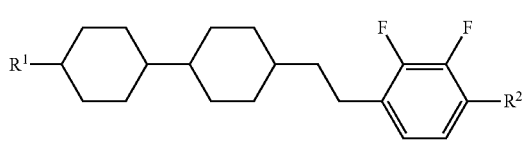

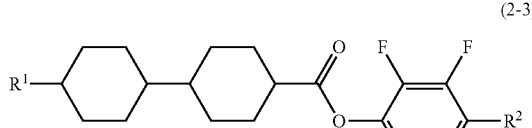

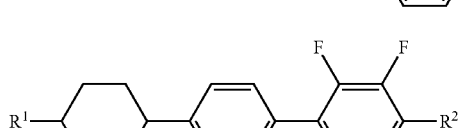

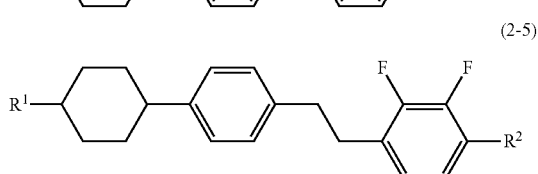

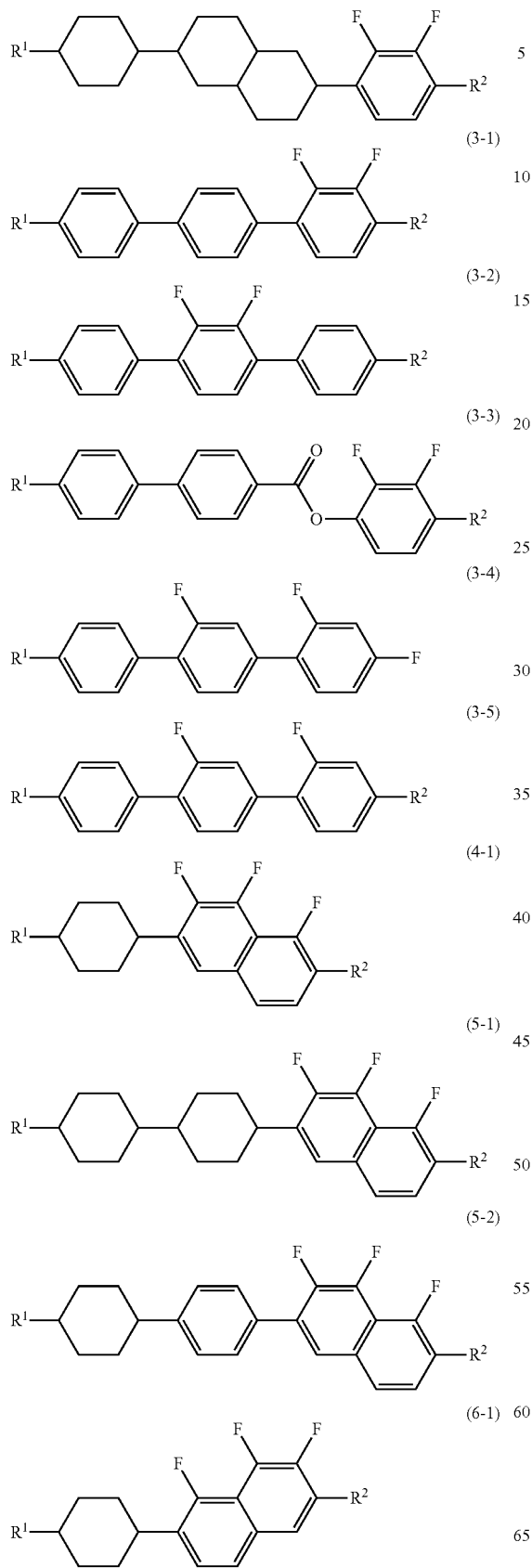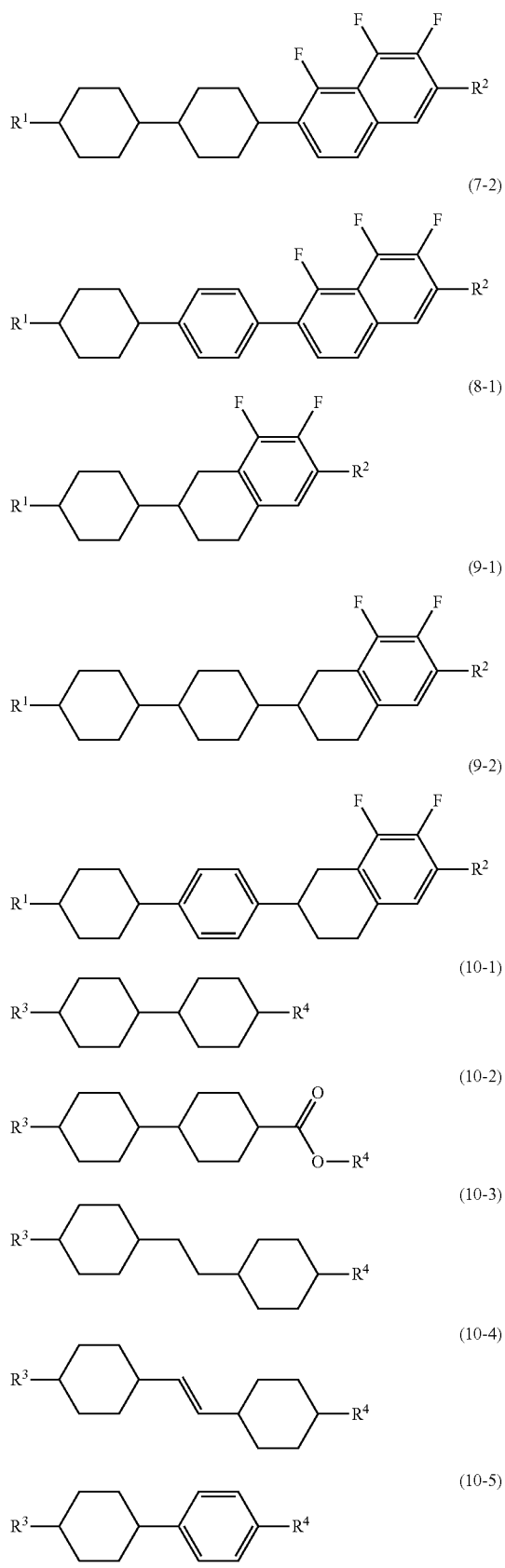

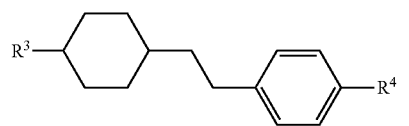 (10-6)
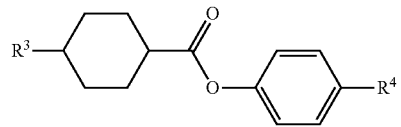 (10-7)
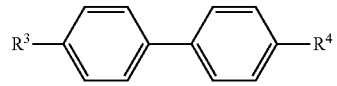 (10-8)
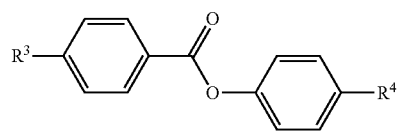 (10-9)
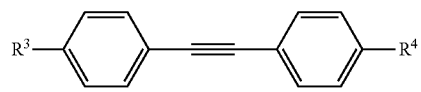 (10-10)
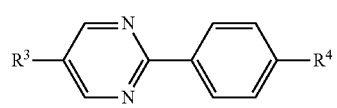 (10-11)
 (11-1)
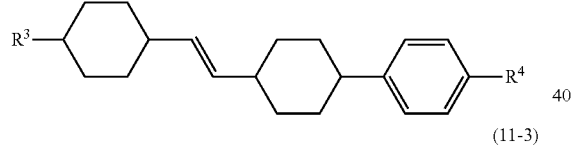 (11-2)
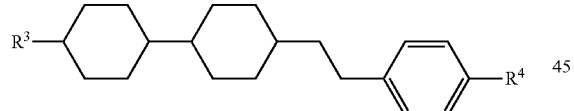 (11-3)
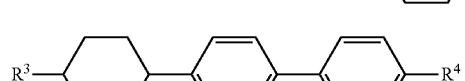 (11-4)
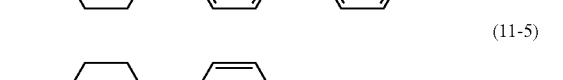 (11-5)
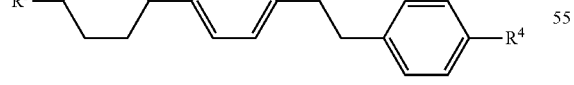 (11-6)
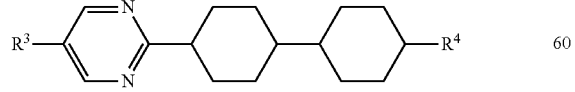 (11-7)

(11-19) 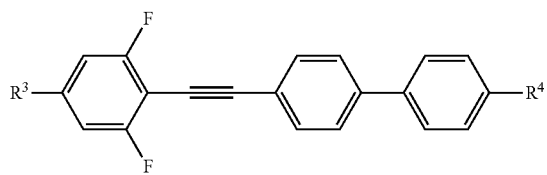

(11-20) 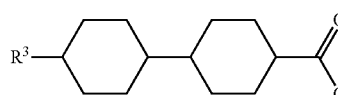

(11-21) 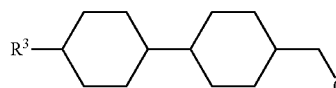

(11-22) 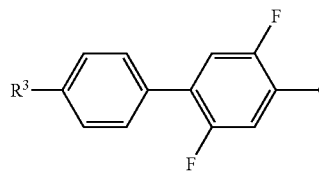

(11-23) 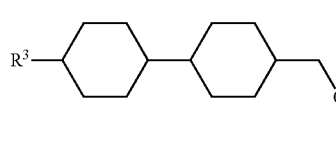

(12-1) 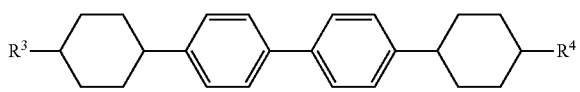

(12-2) 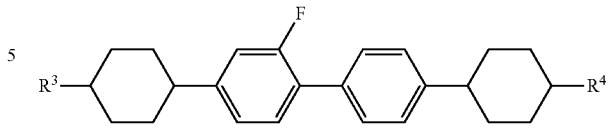

(12-3) 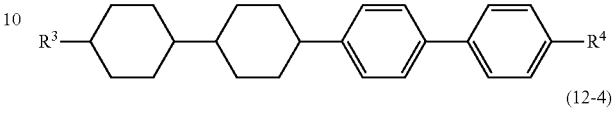

(12-4) 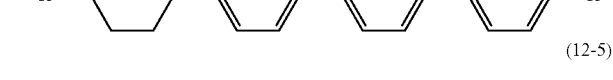

(12-5) 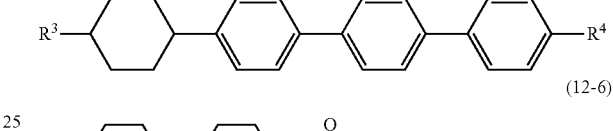

(12-6) 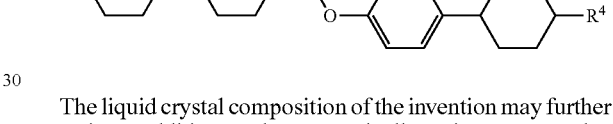

The liquid crystal composition of the invention may further contain an additive, such as an optically active compound, a coloring matter, a antifoaming agent, an ultraviolet light absorbent and an antioxidant.

For example, in the case where an optically active compound is added to the liquid crystal composition, a helical structure of liquid crystal is induced to provide a twist angle.

The optically active compound referred herein means a compound capable of inducing a helical structure of liquid crystal to provide a twist angle (chiral dopant), and examples thereof include compounds represented by formulas (Op-1) to (Op-12) below.

(Op-1) 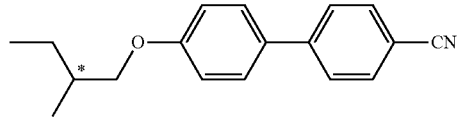

(Op-2) 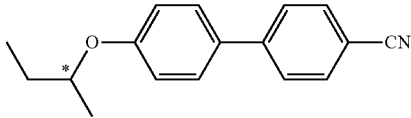

(Op-3) 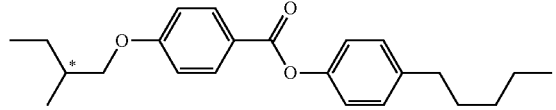

(Op-4) 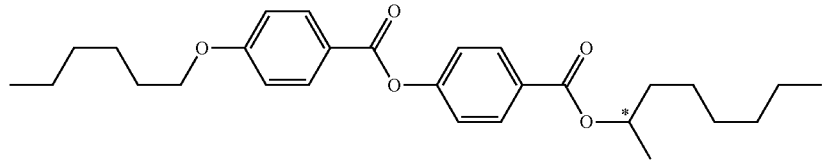

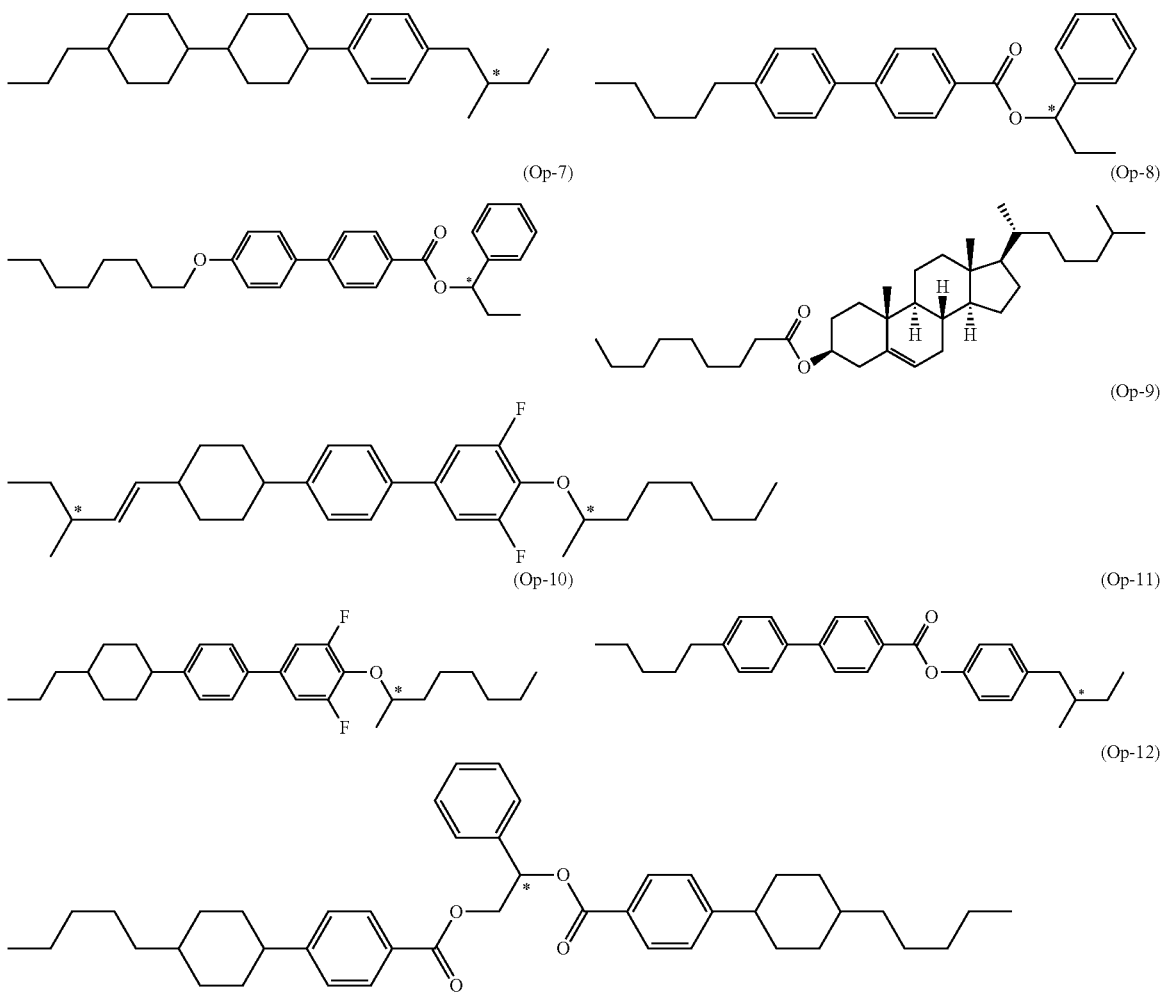

Production Method of Liquid Crystal Composition

The liquid crystal composition of the invention can be produced in the following manner. In the case where compounds as the constitutional components are in a liquid state, the compounds may be mixed and shaken to prepare the composition. In the case where compounds as the constitutional components include solid, the compounds may be mixed and heated to make the solid into a liquid state, followed by shaking, to prepare the composition. The liquid crystal composition of the invention may be produced in any other known methods.

Liquid Crystal Display Device

The liquid crystal composition of the invention may be used in a device having a PC mode, a TN mode, an STN mode, a BTN mode, an ECB mode, an OCB mode, an IPS mode, a VA mode and so forth, and in particular, may be used in a device of an IPS mode and a VA mode by a vertical orientation system. The driving mode of the liquid crystal display devices may be a passive matrix (PM) driving system or an active matrix (AM) driving system.

The liquid crystal display device of the invention can be used as an NCAP (nematic curvilinear aligned phase) device prepared by microcapsulating the liquid crystal composition, and as a PD (polymer dispersed) device having a three-dimensional network polymer formed in the liquid crystal composition, for example, a PN (polymer network) device.

EXAMPLES

The invention will be described in more detail with reference to examples below, but the invention is not construed as being limited to the examples. All occurrences of "%" are by weight unless otherwise indicated.

The resulting compounds are identified by magnetic nuclear resonance spectra obtained by $^1$H-NMR analysis, gas chromatograms obtained by gas chromatography (GC) analysis, and so forth, as described below.

$^1$H-NMR Analysis

DRX-500 (produced by Bruker Biospin Co., Ltd.) was used for measurement. A sample produced in the examples and so forth was dissolved in a deuterated solvent capable of dissolving the sample, such as $CDCl_3$, and the measurement was carried out at room temperature and 500 MHz with an accumulated number of 24. In the description of the resulting nuclear resonance spectra, s means a singlet, d means a doublet, t means a triplet, q means a quartet, and m means a multiplet. Tetramethylsilane (TMS) was used as a standard substance indicating zero point of chemical shift δ.

GC Analysis

Gas Chromatograph Model GC-14B made by Shimadzu was used for measurement. Capillary column CBP1-M25-025 (length: 25 m, bore: 0.22 mm, filmthickness: 0.25 µm, dimethylpolysiloxane as stationary phase, no polarity) produced by Shimadzu Corp. was used as a column. Helium was used as a carrier gas and adjusted to a flow rate of 1 mL/min. The temperature of a sample vaporizing chamber was 280° C., and the temperature of the detector (FID) was 300° C.

The sample was dissolved in toluene to prepare a 1% by weight solution, and 1 µL of the resulting solution was injected into the sample vaporizing chamber.

Chromatopac Model C—R6A, produced by Shimadzu Corp., or an equivalent thereof was used as a recorder. The gas chromatogram obtained showed a retention time of a peak and a peak area corresponding to the component compound.

Solvents for diluting the sample may also be chloroform, hexane, and so forth. The following capillary columns may also be used: a capillary column DB-1, produced by Agilent Technologies Inc. (length: 30 m, bore: 0.32 mm, film thickness: 0.25 µm), a capillary column HP-1, produced by Agilent Technologies Inc. (length: 30 m, bore: 0.32 mm, film thickness: 0.25 mm), a capillary column Rtx-1, produced by Restek Corporation (length: 30 m, bore: 0.32 mm, film thickness: 0.25 µm), and a capillary column BP-1, produced by SGE International Pty. Ltd. (length: 30 m, bore: 0.32 mm, film thickness: 0.25 µm).

An area ratio of each peak in the gas chromatogram corresponds to a ratio of the component compound. In general, the percentages by weight of the component compounds of the analyzed sample are not completely identical to the percentages by area of the peaks of the analyzed sample. According to the invention, however, the percentages by weight of the component compounds of the analyzed sample correspond to the percentages by area of the peaks of the analyzed sample because the correction coefficient is substantially 1 when the aforementioned columns are used in the invention.

Sample of Liquid Crystal Compound for Measuring Characteristics

A sample of the liquid crystal compound for measuring characteristics includes two cases, i.e., the case where the compound itself is used as a sample, and the case where the compound is mixed with based liquid crystals to prepare a sample.

In the later case where a sample is prepared by mixing the compound with based liquid crystals, the measurement is carried out in the following manner. A sample was produced by mixing 15% by weight of the compound and 85% by weight of based liquid crystals. A value of characteristics of the compound was calculated by extrapolating from a value obtained by measurement.

Extrapolated Value=(100×(measured value of sample)−(percentage by weight of based liquid crystals)×(value measured for based liquid crystals))/(percentage by weight of liquid crystal compound)

In the case where a smectic phase or crystals were deposited at 25° C. at this ratio of the liquid crystal compound and the based liquid crystals, the ratio of the compound and the based liquid crystals was changed step by step in the order of (10% by weight/90% by weight), (5% by weight/95% by weight), (1% by weight/99% by weight), respectively. The value of characteristics of the sample was measured at a ratio where a smectic phase or crystals were not deposited at 25° C., and an extrapolated value was obtained by the aforementioned equation, which was designated as a value of characteristics of the liquid crystal compound.

While there are various kinds of based crystals for the aforementioned measurement, the composition of the based crystals A was as follows, for example.

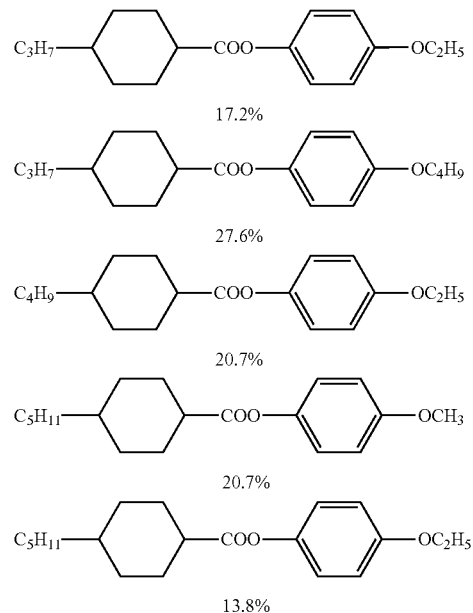

As a sample for measuring a value of characteristics of a liquid crystal composition, the liquid crystal composition itself was used.

Measurement Method of Characteristics of Liquid Crystal Compound

Measurement of the characteristics was carried out according to the following methods. Most methods are described in the Standard of Electric Industries Association of Japan, EIAJ ED-2521A or those with some modifications. A TFT was not attached to a TN device or a VA device used for measurement.

Among the measured values, the values obtained with the liquid crystal compound itself as a sample and the values obtained with the liquid crystal composition itself as a sample were described as experimental data. In the case where the values were obtained with the mixture of the compound with the based liquid crystals, the extrapolated values were described as experimental data.

Phase Structure and Phase Transition Temperature (° C.)

The measurement was carried out in the methods (1) and (2) below.

(1) A compound was placed on a hot plate (Hot Stage Model FP-52, produced by Mettler Co., Ltd.) in a melting point apparatus equipped with a polarizing microscope, and while heating at the rate of 3° C. per minute, the state of the phase and the changes thereof were observed with the polarizing microscope to determine the kind of the phase.

(2) A sample was heated and cooled at a rate of 3° C. per minute by using a scanning calorimeter, DSC-7 System or Diamond DSC System, produced by Perkin-Elmer, Inc., whereby a starting point of an endothermic peak or an exothermic peak associated with phase change of the sample was obtained by extrapolation (on set) to determine phase transition temperature.

In the following description, a crystal is denoted by "C." In the case where a crystal is distinguished into two crystals, they are denoted by "$C_1$" and "$C_2$," respectively. A smectic phase is denoted by "S," and a nematic phase is denoted by "N." A liquid (isotropic phase) is denoted by "Iso." In the case where a smectic phase is distinguished into a smectic B phase and a smectic A phase, they are denoted by "$S_B$" and "$S_A$," respectively. The expression of the phase transition temperature, C 50.0 N 100.0 Iso, for example, means that the transition temperature of from a crystal to a nematic phase (CN) is 50.0° C., and the transition temperature of from a nematic phase to a liquid (NI) is 100.0° C. The other expressions are applied with the same rule.

Maximum Temperature of Nematic Phase ($T_{NI}$; ° C.)

A sample (a liquid crystal composition or a mixture of a liquid crystal compound and the based liquid crystals) was placed on a hot plate (Hot Stage Model FP-52, produced by Mettler Co., Ltd.) in a melting point apparatus equipped with a polarizing microscope, and while heating at the rate of 1° C. per minute, was observed with the polarizing microscope. A temperature where a part of the sample was changed from a nematic phase to an isotropic liquid was designated as a maximum temperature of a nematic phase. The maximum temperature of a nematic phase may be abbreviated to "a maximum temperature" in some cases.

Low Temperature Compatibility

Samples were prepared by mixing the based liquid crystals and a liquid crystal compound to make a ratio of the liquid crystal compound of 20% by weight, 15% by weight, 10% by weight, 5% by weight, 3% by weight and 1% by weight, respectively, and then placed in glass bottles. The glass bottles were stored in a freezer at −10° C. or −20° C. for a prescribed period of time, and then were observed as to whether or not a crystal or a smectic phase was deposited.

Viscosity (η; measured at 20° C.; mPa·s)

The viscosity was measured by means of an E-type rotation viscometer.

Rotation Viscosity (γ1; measured at 25° C.; mPa·s)

The rotation viscosity was measured according to the method disclosed in M. Imai, et al., Molecular Crystals and Liquid Crystals, vol. 259, p. 37 (1995). A sample (a liquid crystal composition or a mixture of a liquid crystal compound and the based liquid crystals) was placed in a VA device having a cell gap between two glass plates of 20 μm. The VA device was impressed with a voltage in a range of from 30 V to 50 V stepwise by 1 V. After a period of 0.2 second with no impress of voltage, voltage impress was repeated with only one rectangular wave (rectangular pulse of 0.2 second) and application of no voltage (2 seconds). A peak current and a peak time of a transient current generated by the voltage impress were measured. The rotation viscosity was obtained from the measured values and the calculating equation (8) in the literature by M. Imai, et al., p. 40. As the dielectric anisotropy necessary for the calculation, the value measured by the measuring method of dielectric anisotropy described below.

Optical Anisotropy (Refractive Index Anisotropy; Δn; Measured at 25° C.)

Measurement was carried out with an Abbe refractometer mounting a polarizing plate on an ocular using light having a wavelength of 589 nm at a temperature of 25° C. The surface of a main prism was rubbed in one direction, and then a sample (a liquid crystal composition or a mixture of a liquid crystal compound and the based liquid crystals) was dropped on the main prism. A refractive index (n∥) was measured when the direction of polarized light was parallel to that of the rubbing. A refractive index (n⊥) was measured when the direction of polarized light was perpendicular to that of the rubbing. A value of optical anisotropy (Δn) was calculated from the equation; (Δn)=(n∥)−(n⊥).

Dielectric Anisotropy (Δ∈; Measured at 25° C.)

A solution of octadecyltriethoxysilane (0.16 mL) and ethanol (20 mL) was coated on a glass substrate having been well cleaned. The glass substrate was spun with a spinner and then heated to 150° C. for 1 hour. A VA device having a distance (cell gap) of 20 μm was fabricated with two sheets of the glass substrates.

A polyimide oriented film was prepared on a glass substrate in the similar manner. The oriented film of the glass substrate was rubbed, and a TN device having a distance between two glass substrates of 9 μm and a twist angle of 80° was fabricated.

A sample (a liquid crystal composition or a mixture of a liquid crystal compound and the based liquid crystals) was put in the VA device, which was then impressed with a voltage of 0.5 V (1 kHz, sine wave) to measure a dielectric constant (∈∥) in the major axis direction of the liquid crystal molecule.

A sample (a liquid crystal composition or a mixture of a liquid crystal compound and the based liquid crystals) was put in the TN device, which was then impressed with a voltage of 0.5 V (1 kHz, sine wave) to measure a dielectric constant (∈⊥) in the minor axis direction of the liquid crystal molecule.

The dielectric anisotropy was calculated from the equation; (Δ∈)=(∈∥)−(∈⊥).

Example 1

Synthesis of 3-(4-pentylphenyl)hydrocoumarin (Compound No. 72)

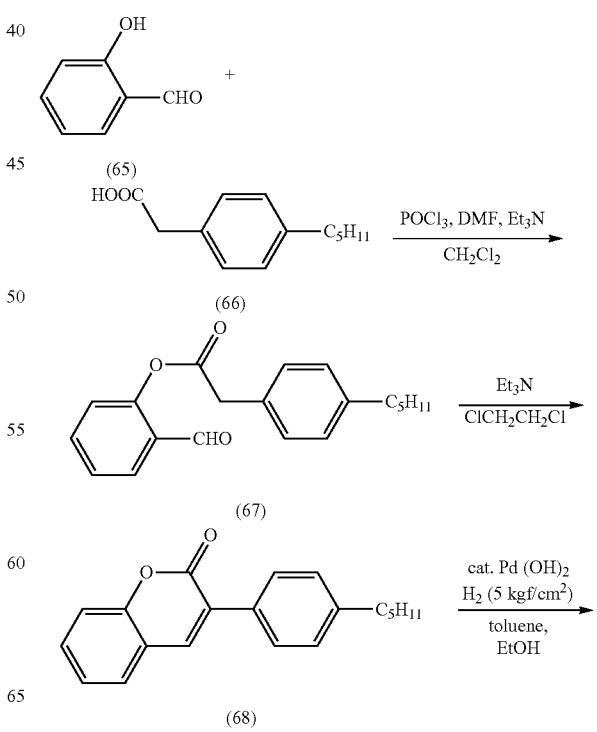

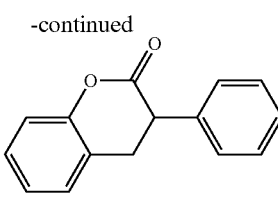

No. 72

First Step

A solution of 15 mL of dichloromethane having dissolved therein phosphoryl chloride (1.26 g, 8.25 mmol) and DMF (0.69 g, 9.45 mmol) was added dropwise to a solution of 60 mL of dichloromethane having dissolved therein salicyl aldehyde (65) (0.91 g, 7.5 mmol), 1-(4-pentylphenyl)acetic acid (66) (1.54 g, 7.5 mmol) and triethylamine (2.27 g, 22.5 mmol) under a nitrogen atmosphere at a temperature maintained at 5° C. or less, followed by reacting at room temperature for 2 hours. The reaction mixture was poured into 50 mL of a saturated $NH_4Cl$ aqueous solution and then extracted with 100 mL of ethyl acetate. The resulting organic layer was washed with water (100 mL twice) and brine (50 mL) and dried over anhydrous sodium sulfate, and the solvent distilled off under reduced pressure. The resulting residue was purified by column chromatography (developing solvent: heptane/ethyl acetate=4/1, column packing: silica gel) to obtain 2-(4-pentylphenyl)acetoxybenzaldehyde (67) (2.22 g, 7.2 mmol). The yield based on the compound (65) was 96%.

Second Step

A solution of 60 mL of 1,2-dichloroethane having dissolved therein 2-(4-pentylphenyl)acetoxybenzaldehyde (67) (2.22 g, 7.2 mmol) obtained in the first step and triethylamine (2.16 g, 21.4 mmol) was heated under refluxing for 5 hours. After cooling the reaction mixture to room temperature, the reaction mixture was poured into 50 mL of a saturated $NH_4Cl$ aqueous solution and then extracted with 100 mL of ethyl acetate. The resulting organic layer was washed with water (100 mL twice) and brine (50 mL) and dried over anhydrous sodium sulfate, and the solvent distilled off under reduced pressure. The resulting residue was purified by column chromatography (developing solvent: heptane/ethyl acetate=4/1, column packing: silica gel) and then recrystallized from a mixed solvent of heptane and ethanol to obtain 3-(4-penthylphenyl)coumarin (68) (1.3 g, 4.4 mmol). The resulting compound was in the form of colorless crystals, and the yield based on the compound (67) was 62%.

Third Step 0.13 g of palladium oxide was added to a solution of 10 mL of toluene and 10 mL of ethanol having dissolved therein 3-(4-penthylphenyl)coumarin (68) (1.3 g, 4.4 mmol) obtained in the second step, and the mixture was reacted under a hydrogen pressure (5 kgf/cm²) at room temperature for 2 days. The reaction mixture was filtered. After concentrating the filtrate, the concentrated filtrate was purified by column chromatography (developing solvent: heptane/ethyl acetate=20/1, column packing: silica gel) and then recrystallized from a mixed solvent of heptane and ethanol to obtain 3-(4-pentylphenyl)hydrocoumarin (Compound No. 72) (0.8 g, 2.7 mmol). The resulting compound was in the form of colorless crystals, and the yield based on the compound (68) was 61%.

The resulting Compound No. 72 had a transition temperature (° C.) of C 68.2 Iso.

The chemical shift δ (ppm) in $^1$H-NMR analysis was as follows, and thus the resulting compound was identified as 3-(4-pentylphenyl)hydrocoumarin (Compound No. 72). The solvent for measurement was $CDCl_3$.

Chemical shift δ (ppm): 7.31-7.08 (m, 8H), 3.94 (dd, 1H), 3.34 (dd, 1H), 3.21 (dd, 1H), 2.85 (t, 2H), 1.60 (m, 2H), 1.31 (m, 3H), 0.90 (t, 3H)

Example 2

Synthesis of 7-ethoxy-8-fluoro-3-(4-pentylphenyl)hydrocoumarin (Compound No. 80)

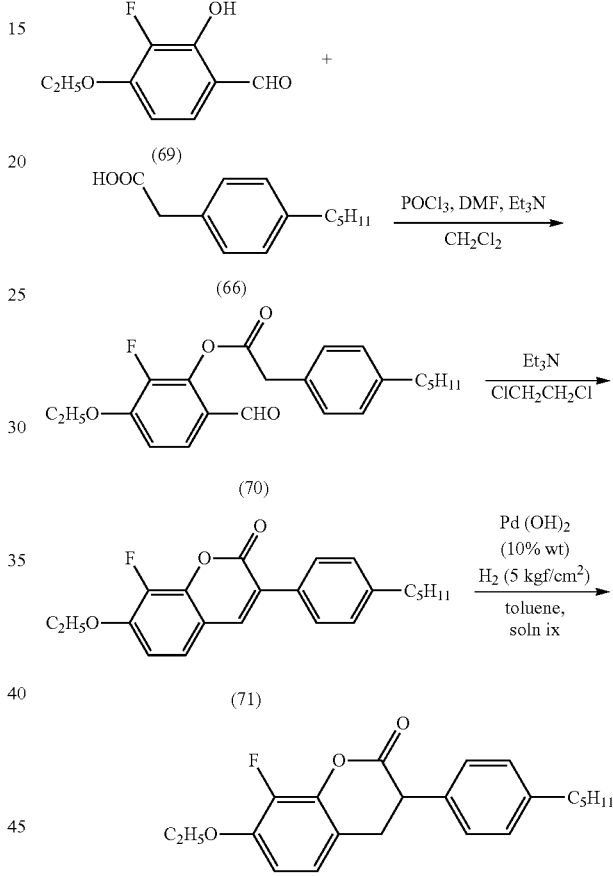

No. 80

First Step

Reaction operations were carried out according to the first step of Example 1 by using 4-ethoxy-3-fluoro-2-hydroxybenzaldehyde (69) (3.82 g, 20.8 mmol) and 1-(4-pentylphenyl)acetate (66) (5.15 g, 24.9 mmol) as starting materials to obtain 4-ethoxy-3-fluoro-2-(4-pentylphenyl)acetoxybenzaldehyde (70) (6.91 g, 18.5 mmol). The resulting compound was in the form of colorless oily matter. The yield based on the compound (69) was 89%.

Second Step

Reaction operations were carried out according to the second step of Example 1 by using 4-ethoxy-3-fluoro-2-(4-pentylphenyl)acetoxybenzaldehyde (70) (6.91 g, 18.5 mmol) obtained in the first step as a starting material to obtain 7-ethoxy-8-fluoro-3-(4-pentylphenyl)coumarin (71) (4.54 g, 12.8 mmol). The resulting compound was in the form of colorless crystals, and the yield based on the compound (70) was 69%.

Third Step

Reaction operations were carried out according to the third step of Example 1 by using 7-ethoxy-8-fluoro-3-(4-pentylphenyl)coumarin (71) (3.70 g, 10.3 mmol) obtained in the second step as a starting material to obtain 7-ethoxy-8-fluoro-3-(4-pentylphenyl)hydrocoumarin (Compound No. 80) (1.47 g, 4.1 mmol). The resulting compound was in the form of colorless crystals, and the yield based on the compound (71) was 40%.

The resulting Compound No. 80 had a transition temperature (° C.) of C 95.7 Iso.

The chemical shift δ (ppm) in $^1$H-NMR analysis was as follows, and thus the resulting compound was identified as 3-(4-pentylphenyl)hydrocoumarin (Compound No. 80). The solvent for measurement was $CDCl_3$.

Chemical shift δ (ppm): 7.18-6.68 (m, 6H), 4.11 (q, 2H), 3.99 (dd, 1H), 3.31 (dd, 1H), 3.19 (dd, 1H), 2.58 (t, 2H), 1.63-1.29 (m, 9H), 0.88 (t, 3H)

Example 3

Synthesis of 6-ethoxy-7-fluoro-2-(4-penthylphenyl)hydroisocoumarin (Compound No. 298)

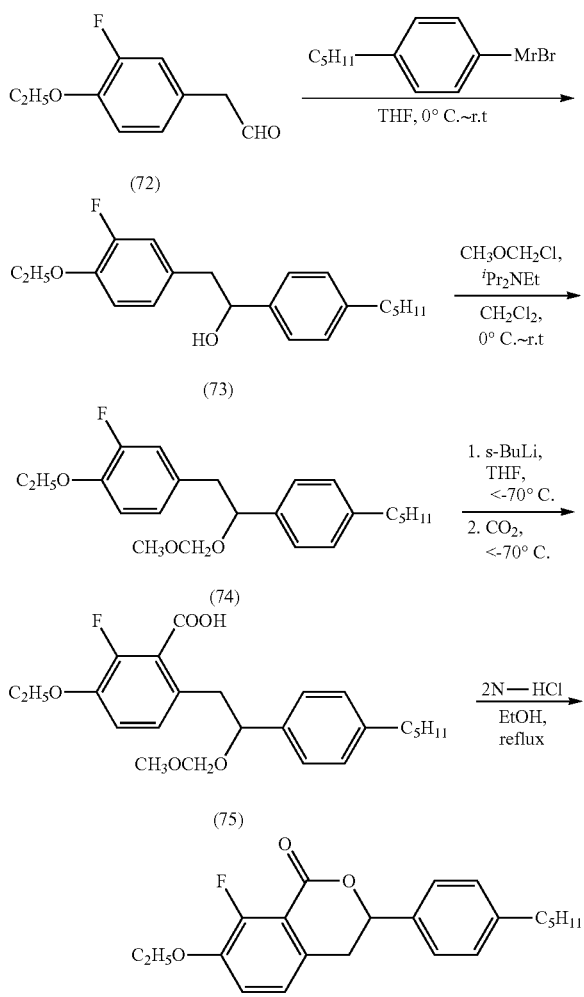

First Step

A Grignard reagent prepared with 4-pentylbromobenzene (7.4 g, 32.9 mmol), magnesium (0.83 g, 34.2 mmol) and 60 mL of tetrahydrofuran was added dropwise to a solution of 40 mL of tetrahydrofuran having dissolved therein 4-ethoxy-3-fluorophenylacetaldehyde (72) (5.0 g, 27.4 mmol) under a nitrogen atmosphere at a temperature maintained at 5° C. or less, followed by reacting at 5° C. or less for 3 hours. The reaction mixture was poured into 100 mL of a saturated $NH_4Cl$ aqueous solution and then extracted with 200 mL of ethyl acetate. The resulting organic layer was washed with water (200 mL twice) and brine (100 mL) and dried over anhydrous sodium sulfate, and the solvent distilled off under reduced pressure. The resulting residue was purified by column chromatography (developing solvent: heptane/ethyl acetate=4/1, column packing: silica gel) to obtain 1-(4-penthyphenyl)-2-(4-ethoxy-3-fluorophenyl)ethanol (73) (3.69 g, 11.2 mmol). The yield based on the compound (72) was 33%.

Second Step

Diisopropylethylamine (5.4 mL, 31.2 mmol) and chloromethyl methyl ether (2.2 mL, 28.5 mmol) were added dropwise to a solution of 30 mL of dichloromethane having dissolved therein 1-(4-penthyphenyl)-2-(4-ethoxy-3-fluorophenyl)ethanol (73) (3.16 g, 9.5 mmol) obtained in the first step under a nitrogen atmosphere at a temperature maintained at room temperature, followed by stirring overnight. The reaction mixture was poured into 20 mL of 1N-hydrochloric acid and then extracted with 100 mL of ethyl acetate. The resulting organic layer was washed with water (100 mL twice) and brine (50 mL) and dried over anhydrous sodium sulfate, and the solvent distilled off under reduced pressure. The resulting residue was purified by column chromatography (developing solvent: heptane/ethyl acetate=9/1, column packing: silica gel) to obtain 1-(4-penthyphenyl)-2-(4-ethoxy-3-fluorophenyl)ethanol methoxymethyl ether (74) (2.82 g, 7.5 mmol). The yield based on the compound (73) was 79%.

Third Step

A 1M-solution of s-BuLi (8.2 mL, 8.2 mmol) was added dropwise to a solution of 50 mL of tetrahydrofuran having dissolved therein 1-(4-penthyphenyl)-2-(4-ethoxy-3-fluorophenyl)ethanol methoxymethyl ether (74) (2.56 g, 6.8 mmol) obtained in the second step at a temperature of from −70 to −75° C., followed by stirring at the same temperature for 1 hour. After adding frozen carbon dioxide (1.2 g, 27.4 mmol) to the reaction mixture, the temperature of which was then gradually increased to room temperature, followed by stirring overnight. The reaction mixture was poured into 40 mL of 1N-hydrochloric acid and then extracted with 100 mL of ethyl acetate. The resulting organic layer was washed with water (100 mL twice) and brine (50 mL) and dried over anhydrous sodium sulfate, and the solvent distilled off under reduced pressure. The resulting residue was purified by column chromatography (developing solvent: heptane/ethyl acetate=1/4, column packing: silica gel) to obtain 1-(4-penthyphenyl)-2-(4-ethoxy-2-carbooxy-3-fluorophenyl)ethanol methoxymethyl ether (75) (1.5 g, 3.6 mmol). The yield based on the compound (74) was 34%.

Fourth Step

2N-Hydrochloric acid (7.5 mL, 15 mmol) was added to a solution of 15 mL of ethanol having dissolved therein 1-(4-penthyphenyl)-2-(4-ethoxy-2-carbooxy-3-fluorophenyl)ethanol methoxymethyl ether (75) (1.5 g, 3.6 mmol) obtained in the third step, followed by heating under refluxing for 2 hours. The reaction mixture was poured into 100 mL of water and then extracted with 100 mL of ethyl acetate. The resulting organic layer was washed with water (100 mL twice) and brine (50 mL) and dried over anhydrous sodium sulfate, and the solvent distilled off under reduced pressure. The resulting residue was purified by column chromatography (developing solvent: toluene, column packing: silica gel) and then recrystallized from a mixed solvent of heptane and ethanol to obtain 6-ethoxy-7-fluoro-2-(4-penthylphenyl)hydroisocoumarin (Compound No. 298) (0.56 g, 1.6 mmol). The resulting compound was in the form of colorless crystals, and the yield based on the compound (75) was 44%.

The resulting Compound No. 298 had a transition temperature (° C.) of C 78.1 Iso.

The chemical shift δ (ppm) in ¹H-NMR analysis was as follows, and thus the resulting compound was identified as 6-ethoxy-7-fluoro-2-(4-penthylphenyl)hydroisocoumarin (Compound No. 298). The solvent for measurement was CDCl₃.

Chemical shift δ (ppm): 7.36-6.96 (m, 6H), 5.44 (dd, 1H), 4.13 (q, 2H), 3.24 (dd, 1H), 3.04 (d, 1H), 2.62 (t, 2H), 1.64-1.30 (m, 9H), 0.89 (t, 3H)

Example 4

Synthesis of 3-ethyl-2,2,8-trifluoro-7-(4-penthylphenyl)hydrocoumarin (Compound No. 456)

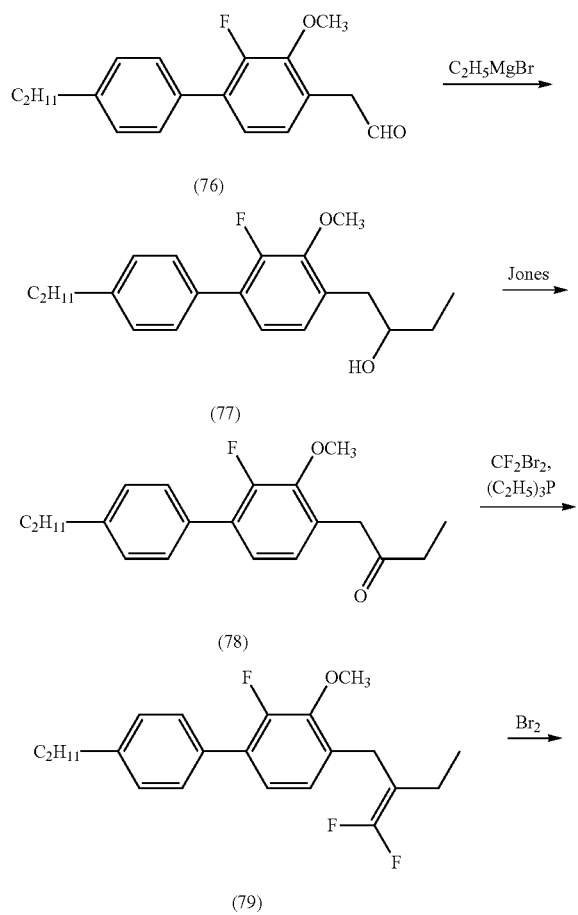

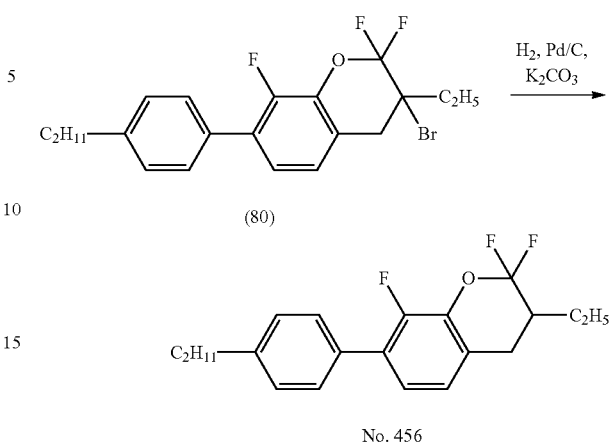

First Step

A solution of 50 mL of tetrahydrofuran having dissolved therein (2-fluoro-3-methoxy-4'-pentyl-4-biphenyl)acetaldehyde (76) (28.3 g, 90.0 mmol) was added dropwise to a solution of 50 mL of tetrahydrofuran having dissolved therein a 3M-solution of ethylmagnesium bromide (36.0 mL, 108.0 mmol) under a nitrogen atmosphere at a temperature maintained at 20° C. or less, followed by reacting at room temperature for 3 hours. The reaction mixture was poured into 100 mL of a saturated NH₄Cl aqueous solution and then extracted with 100 mL of toluene. The resulting organic layer was washed with water (100 mL twice) and brine (50 mL) and dried over anhydrous sodium sulfate, and the solvent distilled off under reduced pressure to obtain crude 2-fluoro-4-(2-hydroxybutyl)-3-methoxy-4'-pentylbiphenyl (77) (30.6 g, 89.0 mmol). The resulting compound was in the form of white solid, and the yield based on the compound (76) was 99%.

Second Step

A Jones reagent of 2.66M (38.0 mL, 101 mmol) was added dropwise to a solution of 200 mL of acetone having dissolved therein 2-fluoro-4-(2-hydroxybutyl)-3-methoxy-4'-pentylbiphenyl (77) (30.6 g, 89.0 mmol) obtained in the first step at a temperature maintained at 35° C. or less, followed by stirring at room temperature for 3 hours. The reaction mixture was poured into 200 mL of water and then extracted with 200 mL of toluene. The resulting organic layer was washed with water (200 mL), saturated sodium bicarbonate water (100 mL thrice), water (200 mL thrice) and brine (100 mL) and dried over anhydrous sodium sulfate, and the solvent distilled off under reduced pressure. The resulting residue was purified by column chromatography (developing solvent: toluene, column packing: silica gel) to obtain 2-fluoro-3-methoxy-4'-pentyl-4-biphenyl-2-butanone (78) (24.4 g, 71.2 mmol). The yield based on the compound (77) was 80%.

Third Step

A solution of 50 mL of tetrahydrofuran having dissolved therein triethylphosphine (54.5 g, 220.7 mmol) was added dropwise to a solution of 50 mL of tetrahydrofuran having dissolved therein 2-fluoro-3-methoxy-4'-pentyl-4-biphenyl-2-butanone (78) (24.4 g, 71.2 mmol) obtained in the second step at 20° C., followed by stirring at the same temperature for 30 minutes. A solution of 20 mL of tetrahydrofuran having dissolved therein dibromodifluoromethane (22.4 g, 106.8 mmol) was added to the reaction mixture, which was then stirred at 40° C. for 3 hours. The reaction mixture was poured into 200 mL of water and then extracted with 200 mL of toluene. The resulting organic layer was washed with water (200 mL), 1N-hydrochloric acid (200 mL), water (200 mL thrice) and brine (100 mL) and dried over anhydrous sodium sulfate, and the solvent distilled off under reduced pressure. The resulting residue was purified by column chromatography (developing solvent: toluene/heptane=1/1, column packing: silica gel) to obtain 2-fluoro-3-methoxy-4'-pentyl-4-(1, 1-difluoro-2-ethyl-1-propenyl)biphenyl (79) (2.68 g, 7.1 mmol).

Fourth Step

Bromine (1.36 g, 8.54 mmol) was added dropwise to a solution of 25 mL of dichloromethane having dissolved therein 2-fluoro-3-methoxy-4'-pentyl-4-(1,1-difluoro-2-ethyl-1-propenyl)biphenyl (79) (2.68 g, 7.1 mmol) obtained in the third step at a temperature of 20° C. or less, followed by stirring for 1 hour. The reaction mixture was poured into 200 mL of water and then extracted with 100 mL of toluene. The resulting organic layer was washed with water (100 mL), saturated sodium bicarbonate water (100 mL twice), water (100 mL twice) and brine (50 mL) and dried over anhydrous sodium sulfate, and the solvent distilled off under reduced pressure. The resulting residue was purified by column chromatography (developing solvent: toluene, column packing: silica gel) to obtain 3-bromo-3-ethyl-2,2,8-trifluoro-7-(4-pentylphenyl)-hydrocoumarin (80) (1.88 g, 4.3 mmol).

Fifth Step 0.19 g of a carbon-palladium catalyst and potassium carbonate (0.85 g, 2.34 mmol) were added to a solution of 10 mL of toluene and 10 mL of ethanol having dissolved therein 3-bromo-3-ethyl-2,2,8-trifluoro-7-(4-pentylphenyl)-hydrocoumarin (80) (1.88 g, 4.3 mmol) obtained in the fourth step, and the mixture was reacted under a hydrogen atmosphere for 1 day. The reaction mixture was filtered and concentrated. The resulting residue was purified by column chromatography (developing solvent: toluene, column packing: silica gel) and then recrystallized from a mixed solvent of heptane and ethanol to obtain 3-ethyl-2,2,8-trifluoro-7-(4-penthylphenyl) hydrocoumarin (Compound No. 456).

The resulting Compound No. 456 had the following mass spectrum.

GC-MS (EI): 362 (M+, 10%), 305 (100%)

Example 5

Characteristics of 3-(4-pentylphenyl)hydrocoumarin (Compound No. 72)

The five compounds described above as the based liquid crystals A were mixed to prepare based liquid crystals A having a nematic phase. The based liquid crystals A had the following characteristics:

Maximum Temperature ($T_{NI}$)=74.0° C.
Optical Anisotropy ($\Delta n$)=0.087
Dielectric Anisotropy ($\Delta \in$)=−1.3

85% by weight of the based liquid crystals A and 15% by weight of 3-(4-pentylphenyl)hydrocoumarin (Compound No. 72) were mixed to prepare a liquid crystal composition B. The liquid crystal composition B had the following characteristics.

Optical Anisotropy ($\Delta n$)=0.075
Dielectric Anisotropy ($\Delta \in$)=−1.64

The liquid crystal compound (No. 72) had the following characteristics as calculated by extrapolation with the characteristics of the based liquid crystals A and the liquid crystal composition B and the mixing ratio of the compounds.

Optical Anisotropy ($\Delta n$)=0.010
Dielectric Anisotropy ($\Delta \in$)=−2.43

The dielectric anisotropy ($\Delta \in$) was negatively increased by adding the liquid crystal compound (No. 72) to the based liquid crystals A, and therefore, it was found that a liquid crystal display device using a liquid crystal composition containing the liquid crystal compound (No. 72) as a constitutional component could be driven at a low voltage.

Example 6

Characteristics of 7-ethoxy-8-fluoro-3-(4-pentylphenyl)hydrocoumarin (Compound No. 80)

90% by weight of the based liquid crystals A and 10% by weight of 7-ethoxy-8-fluoro-3-(4-pentylphenyl)hydrocoumarin (Compound No. 80) were mixed to prepare a liquid crystal composition C. The liquid crystal composition C had the following characteristics.

Optical Anisotropy ($\Delta n$)=0.091
Dielectric Anisotropy ($\Delta \in$)=−2.82

The liquid crystal compound (No. 80) had the following characteristics as calculated by extrapolation with the characteristics of the based liquid crystals A and the liquid crystal composition C and the mixing ratio of the compounds.

Optical Anisotropy ($\Delta n$)=0.124
Dielectric Anisotropy ($\Delta \in$)=−14.97

The dielectric anisotropy ($\Delta \in$) was negatively increased considerably by adding the liquid crystal compound (No. 80) to the based liquid crystals A, and therefore, it was found that a liquid crystal display device using a liquid crystal composition containing the liquid crystal compound (No. 80) as a constitutional component could be driven at a low voltage.

Example 7

Characteristics of 6-ethoxy-7-fluoro-2-(4-penthylphenyl)hydroisocoumarin (Compound No. 298)

85% by weight of the based liquid crystals A and 15% by weight of 6-ethoxy-7-fluoro-2-(4-penthylphenyl)hydroisocoumarin (Compound No. 298) were mixed to prepare a liquid crystal composition D. The liquid crystal composition D had the following characteristics.

Optical Anisotropy ($\Delta n$)=0.090
Dielectric Anisotropy ($\Delta \in$)=−4.35

The liquid crystal compound (No. 298) had the following characteristics as calculated by extrapolation with the characteristics of the based liquid crystals A and the liquid crystal composition D and the mixing ratio of the compounds.

Optical Anisotropy ($\Delta n$)=0.106
Dielectric Anisotropy ($\Delta \in$)=−20.61

The dielectric anisotropy ($\Delta \in$) was negatively increased considerably by adding the liquid crystal compound (No. 298) to the based liquid crystals A, and therefore, it was found that a liquid crystal display device using a liquid crystal composition containing the liquid crystal compound (No. 298) as a constitutional component could be driven at a low voltage.

Example 8

The compounds No. 1 to 456 are synthesized in the similar manners as those having been described.

| No. | |
|---|---|
| 1 | 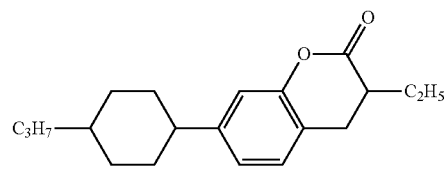 |
| 2 | 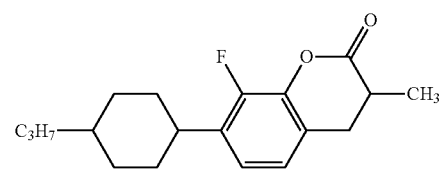 |
| 3 | 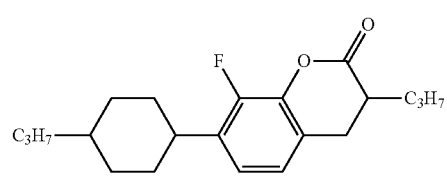 |
| 4 | 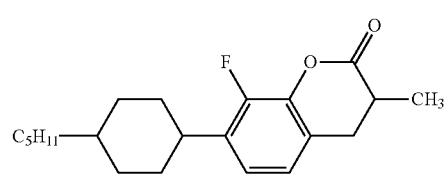 |
| 5 | 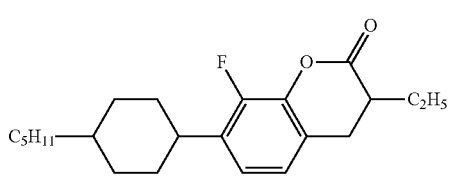 |
| 6 | 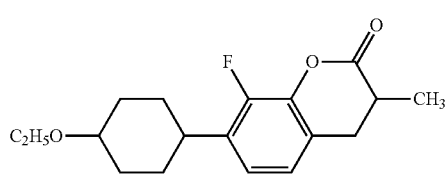 |
| 7 | 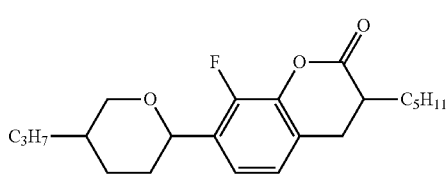 |
| 8 | 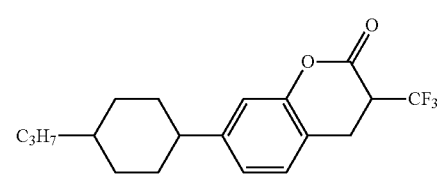 |
| 9 | 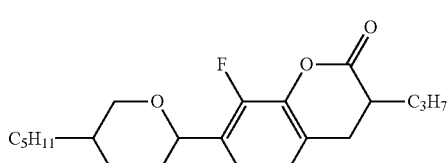 |

-continued
No.
10 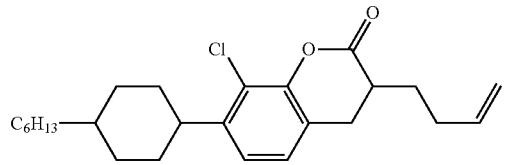
11 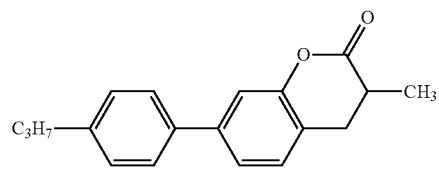
12 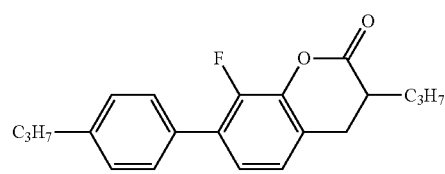
13 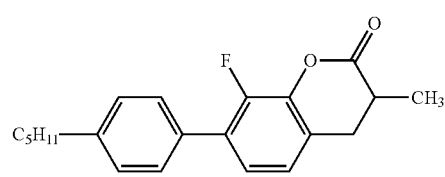
14 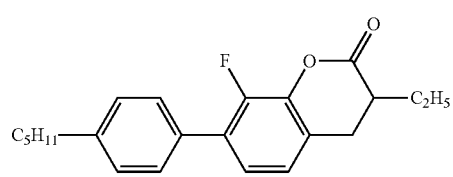
15 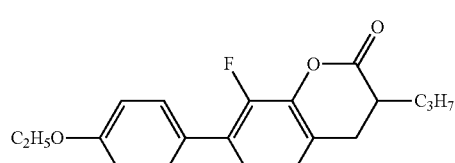
16 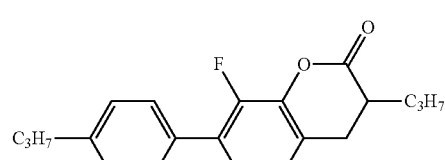
17 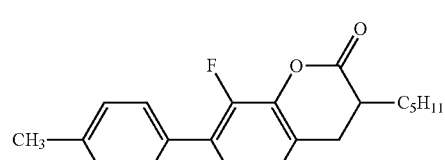
18 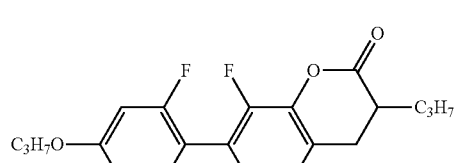

-continued
| No. | |
|---|---|
| 19 | 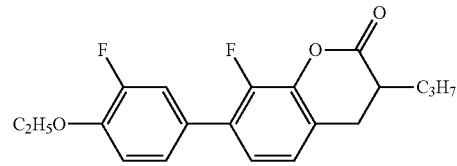 |
| 20 | 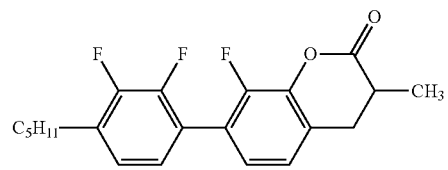 |
| 21 | 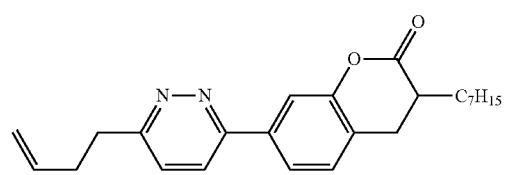 |
| 22 | 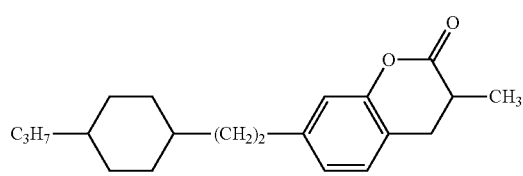 |
| 23 | 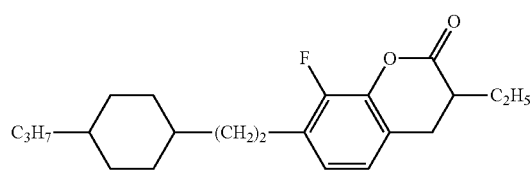 |
| 24 | 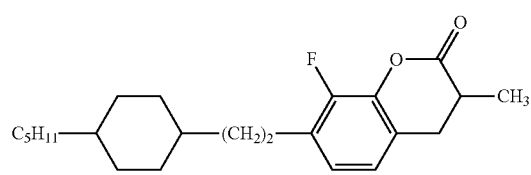 |
| 25 | 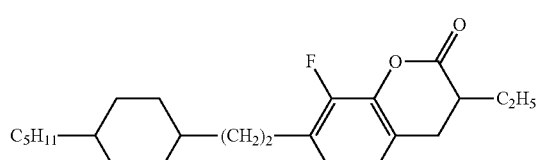 |
| 26 | 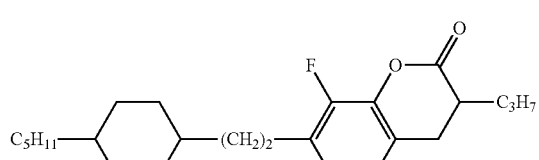 |
| 27 | 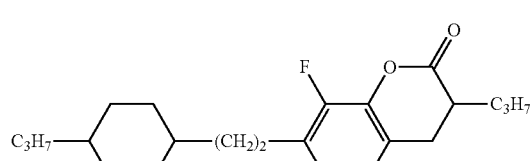 |

| No. | |
|---|---|
| 28 | 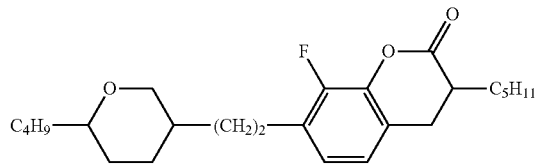 |
| 29 | 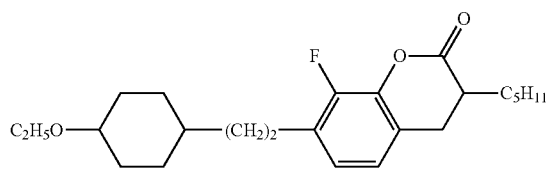 |
| 30 | 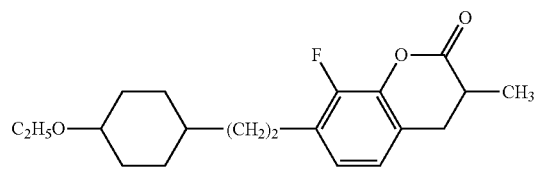 |
| 31 | 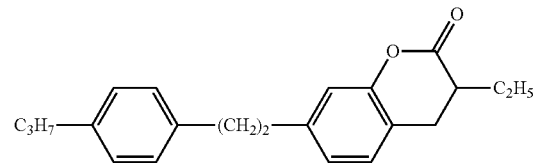 |
| 32 | 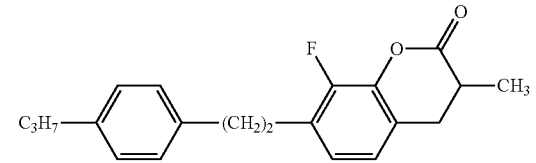 |
| 33 | 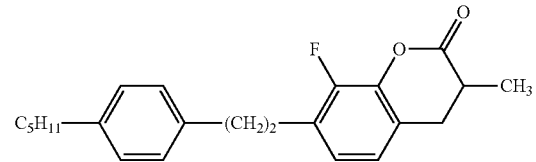 |
| 34 | 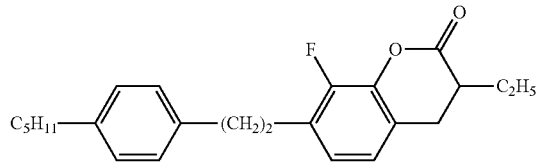 |
| 35 | 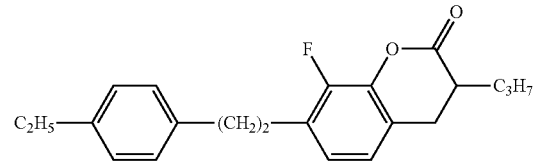 |
| 36 | 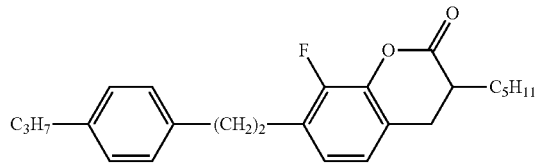 |

-continued
| No. | |
|---|---|
| 37 | 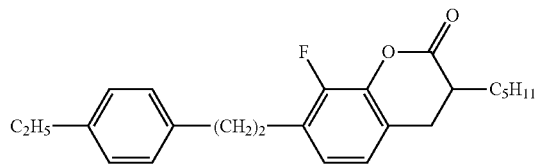 |
| 38 | 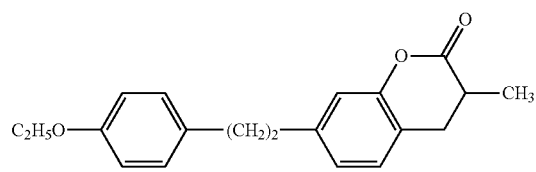 |
| 39 | 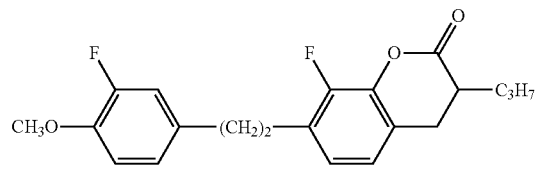 |
| 40 | 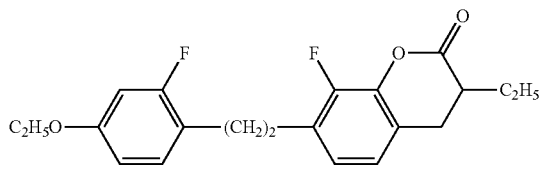 |
| 41 | 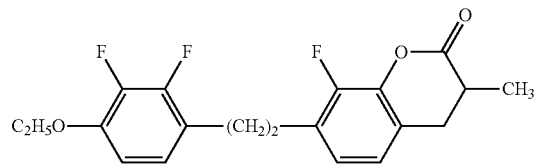 |
| 42 | 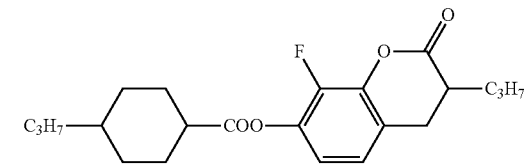 |
| 43 | 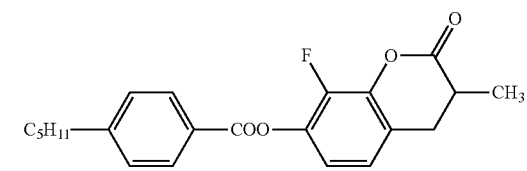 |
| 44 | 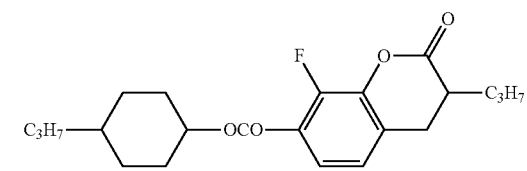 |
| 45 | 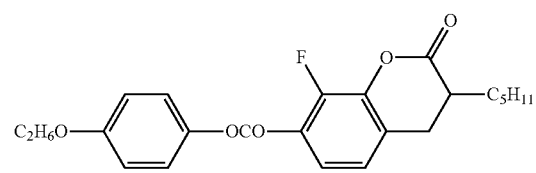 |

-continued
| No. | |
|---|---|
| 46 | 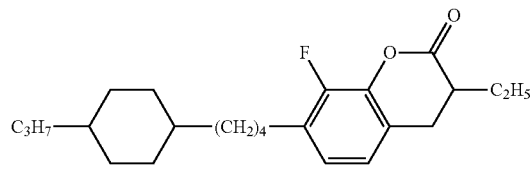 |
| 47 | 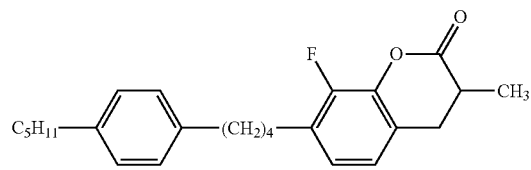 |
| 48 | 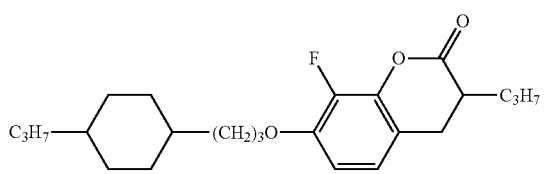 |
| 49 | 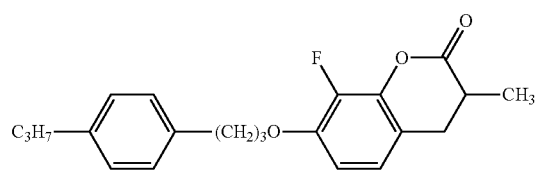 |
| 50 | 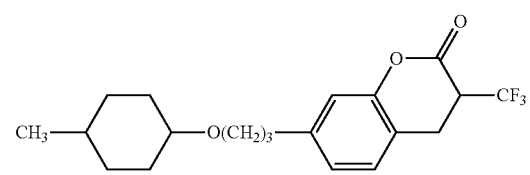 |
| 51 | 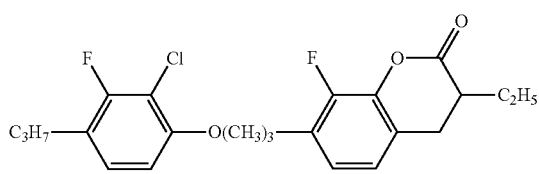 |
| 52 | 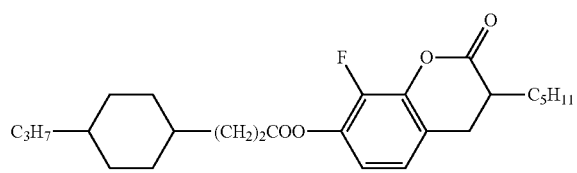 |
| 53 | 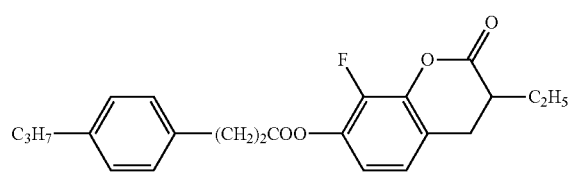 |
| 54 | 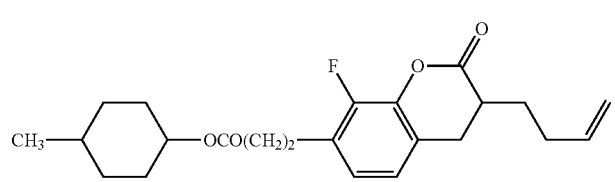 |

-continued
| No. | |
|---|---|
| 55 | 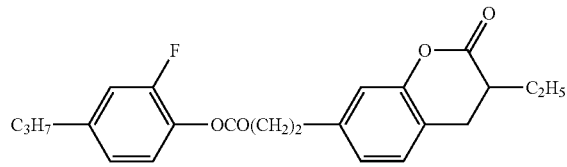 |
| 56 | 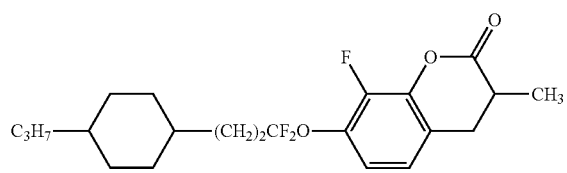 |
| 57 | 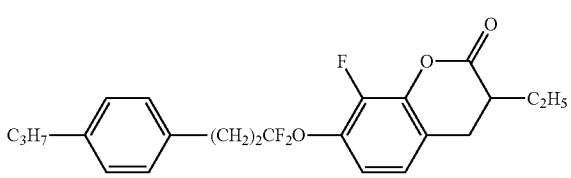 |
| 58 | 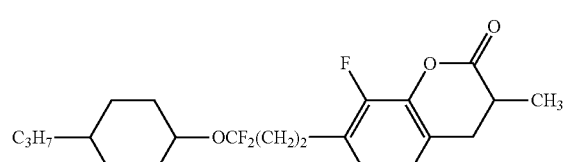 |
| 59 | 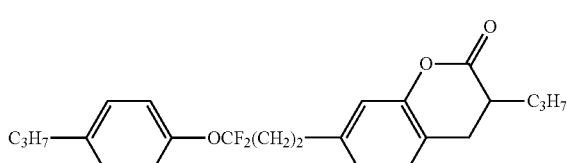 |
| 60 | 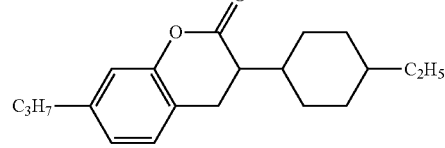 |
| 61 | 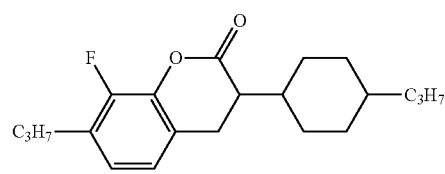 |
| 62 | 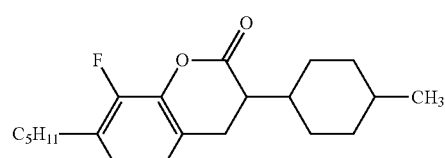 |
| 63 | 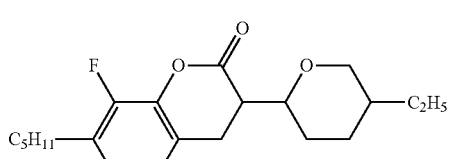 |

-continued
| No. | |
|---|---|
| 64 | 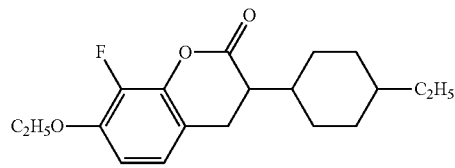 |
| 65 | 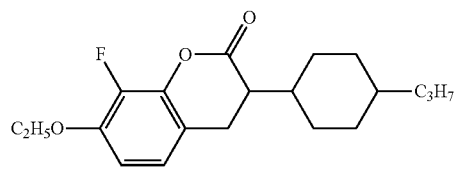 |
| 66 | 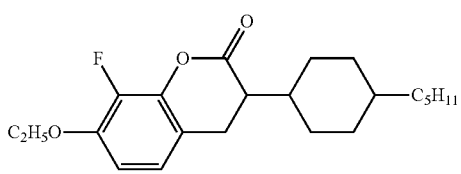 |
| 67 | 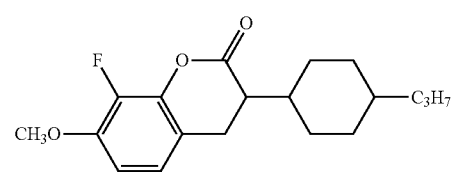 |
| 68 | 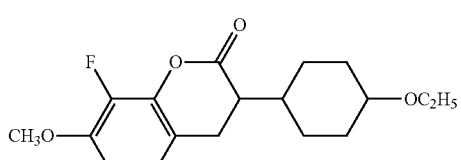 |
| 69 | 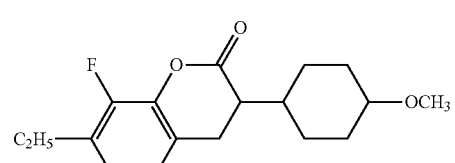 |
| 70 | 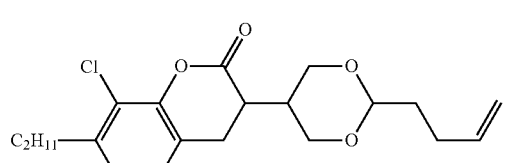 |
| 71 | 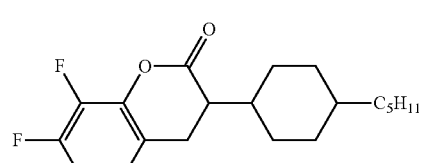 |

-continued
| No. | |
|---|---|
| 72 | 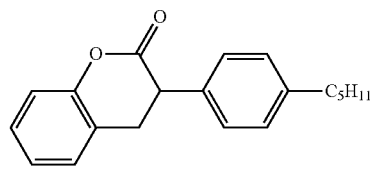
C 68.2 I
Δ ε: -2.43, Δ n: 0.075 |
| 73 | 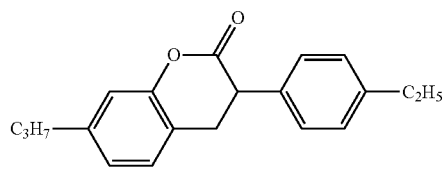 |
| 74 | 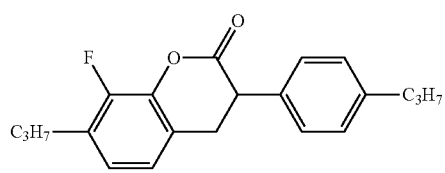 |
| 75 | 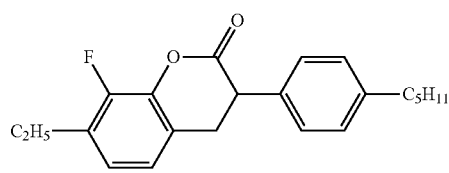 |
| 76 | 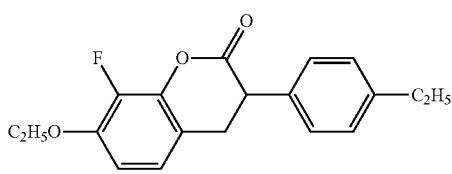 |
| 77 | 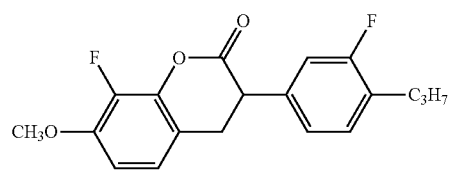 |
| 78 | 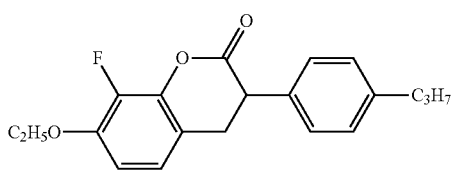 |
| 79 | 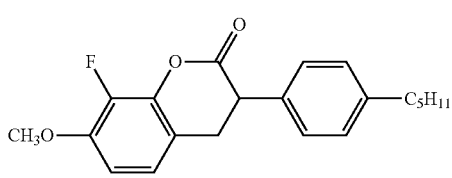 |

| No. | |
|---|---|
| 80 | 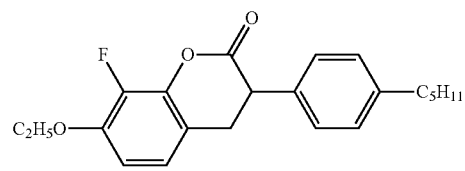 C 95.7 I Δ ε: -14.97, Δ n: 0.124 |
| 81 | 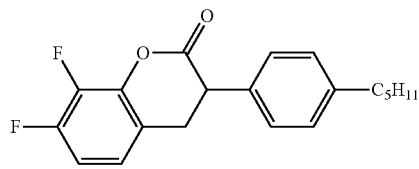 |
| 82 | 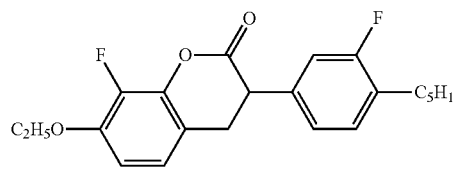 |
| 83 | 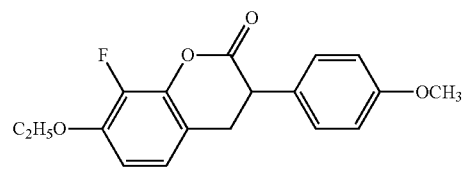 |
| 84 | 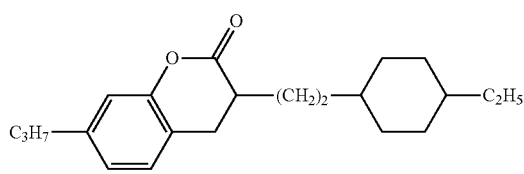 |
| 85 | 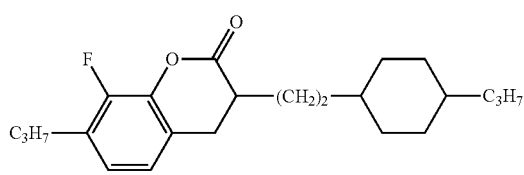 |
| 86 | 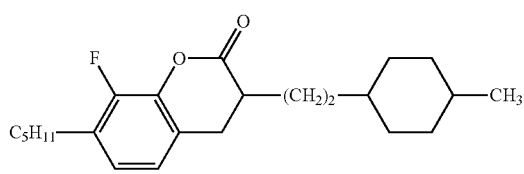 |
| 87 | 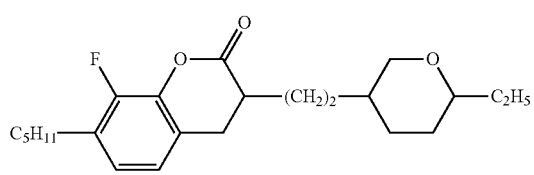 |

-continued
| No. |  |
|---|---|
| 88 | 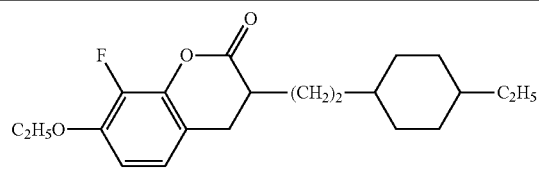 |
| 89 | 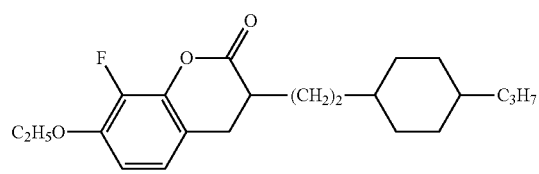 |
| 90 | 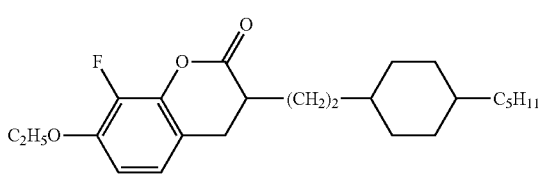 |
| 91 | 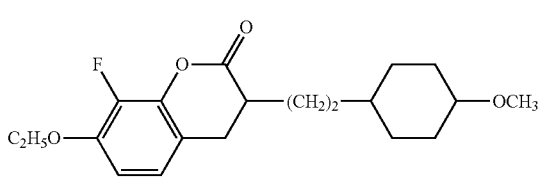 |
| 92 | 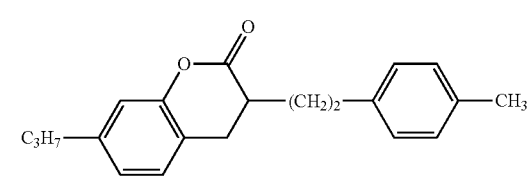 |
| 93 | 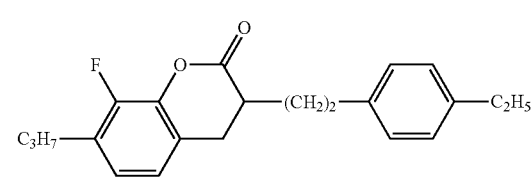 |
| 94 | 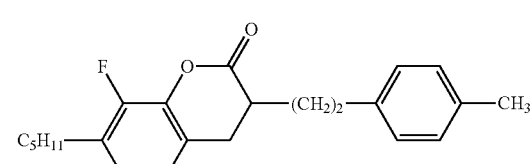 |
| 95 | 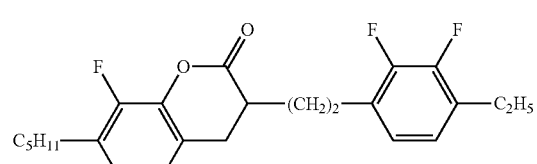 |
| 96 | 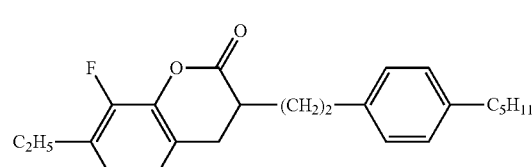 |

-continued
| No. | |
|---|---|
| 97 | 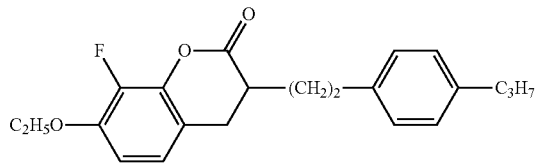 |
| 98 | 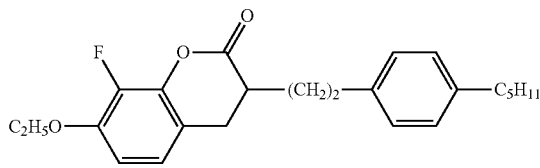 |
| 99 | 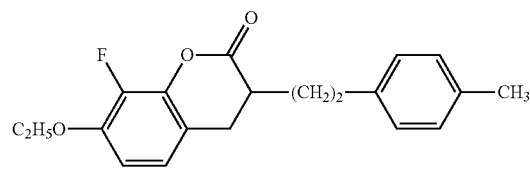 |
| 100 | 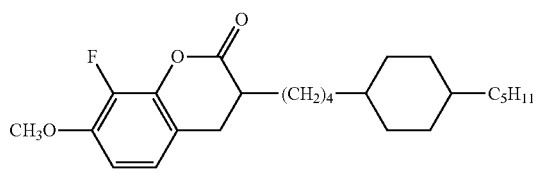 |
| 101 | 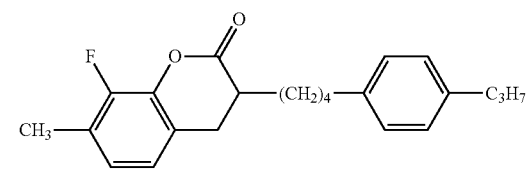 |
| 102 | 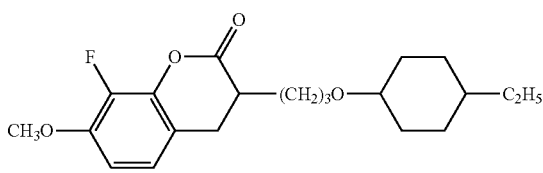 |
| 103 | 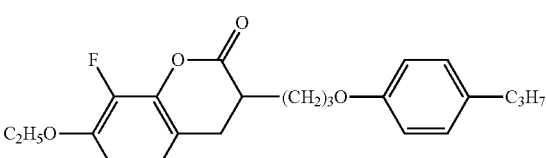 |
| 134 | 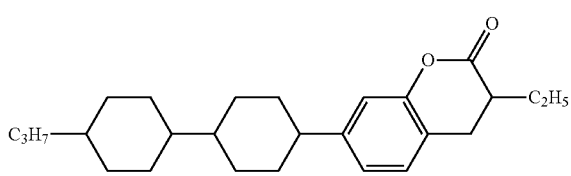 |
| 135 | 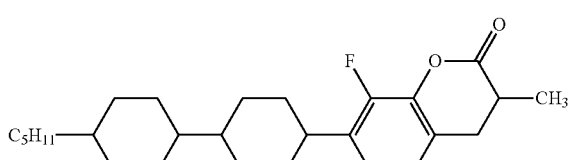 |

-continued
| No. | |
|---|---|
| 136 | 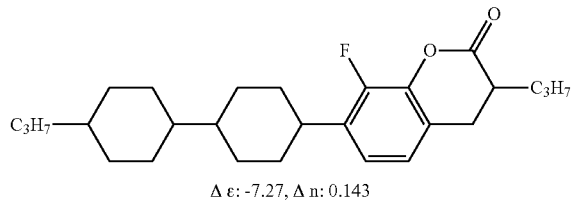<br>Δ ε: -7.27, Δ n: 0.143 |
| 137 | 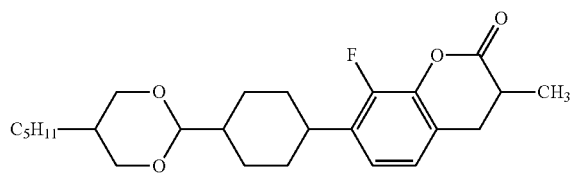 |
| 138 | 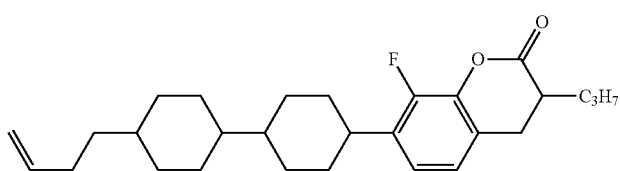 |
| 139 | 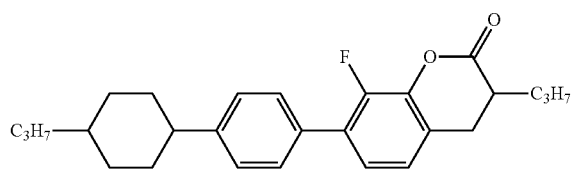 |
| 140 | 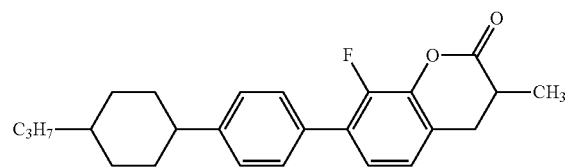 |
| 141 | 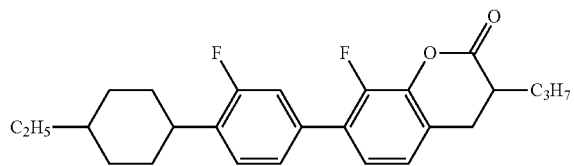 |
| 142 | 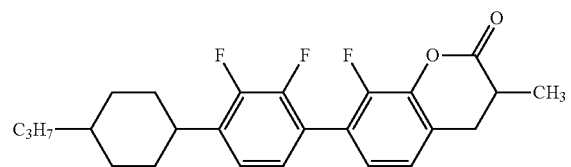 |
| 143 | 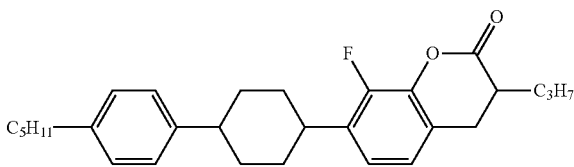 |

-continued
| No. | |
|---|---|
| 144 | 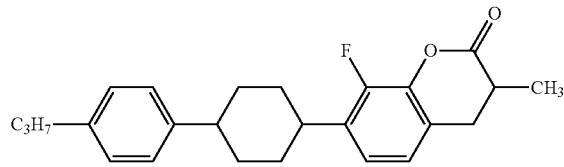 |
| 145 | 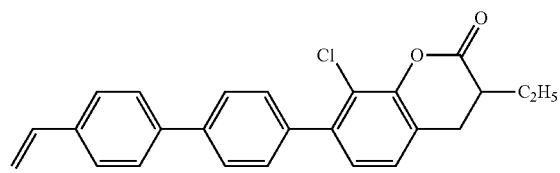 [SMILES: C=Cc1ccc(-c2ccc(-c3ccc4c(c3Cl)OC(=O)C(CC)C4)cc2)cc1] |
| 146 | 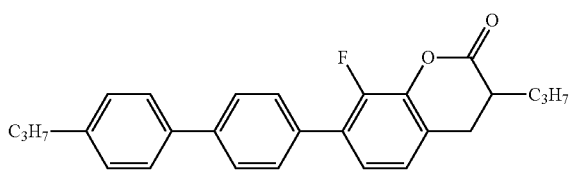 |
| 147 | 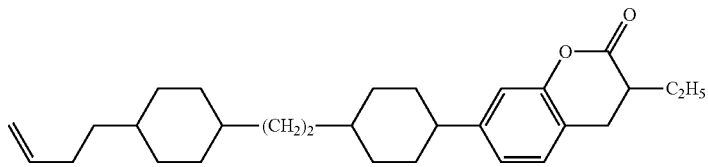 |
| 148 | 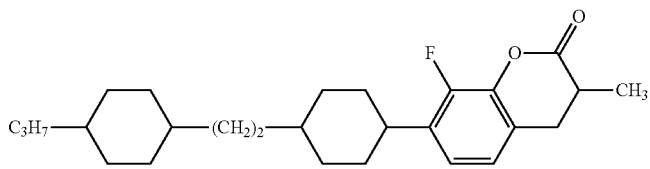 |
| 149 | 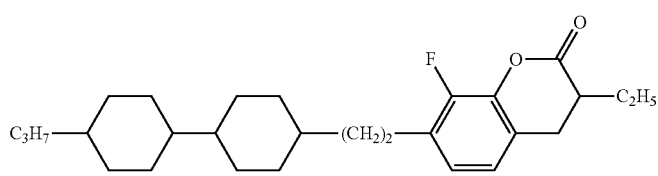 |
| 150 | 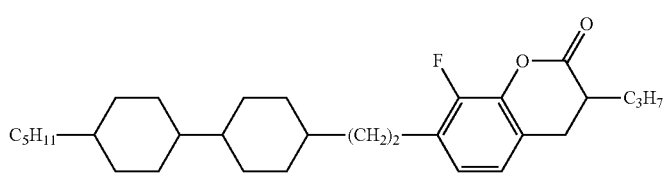 |
| 151 | 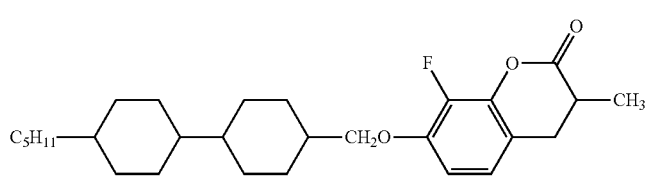 |
| 152 | 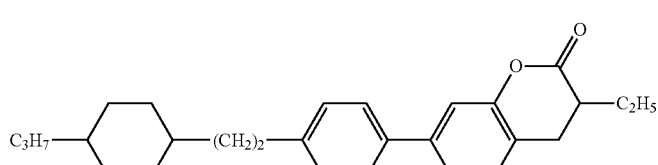 |

-continued
| No. | |
|---|---|
| 153 | 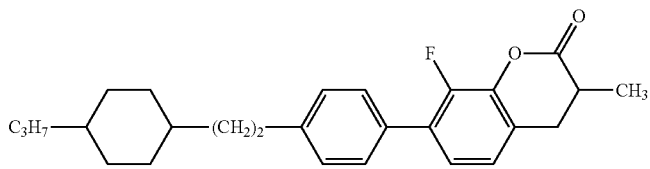 |
| 154 | 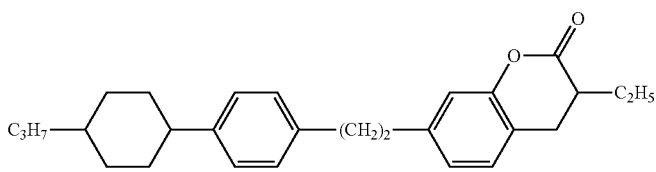 |
| 155 | 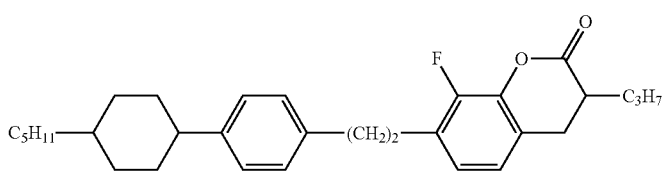 |
| 156 | 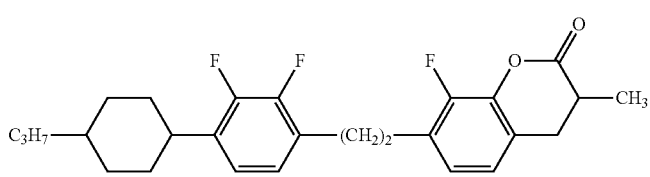 |
| 157 | 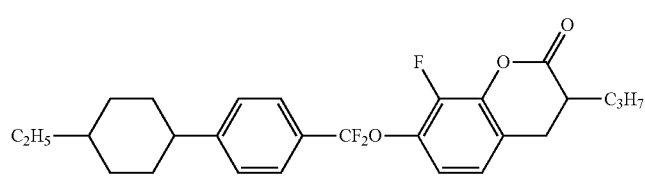 |
| 158 | 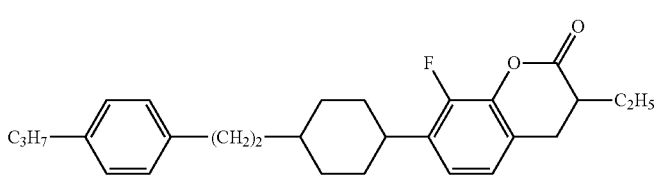 |
| 159 | 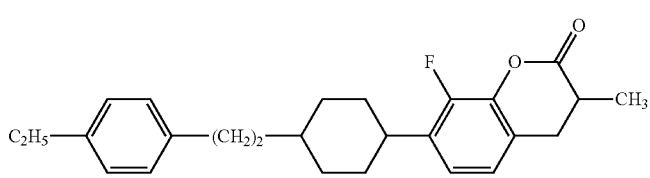 |
| 160 | 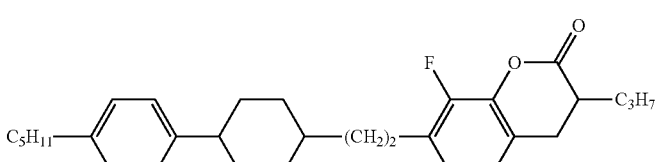 |
| 161 | 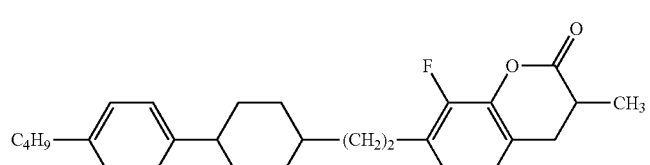 |

-continued
No.
162
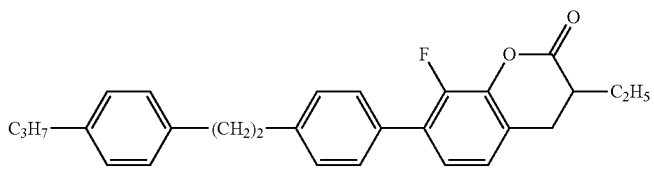
163
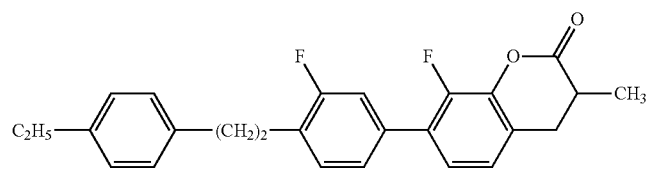
164
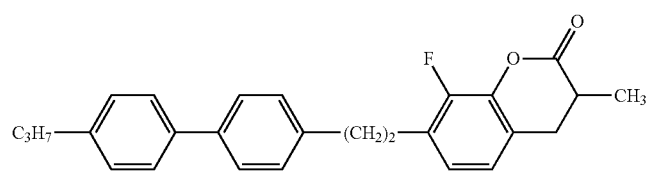
165
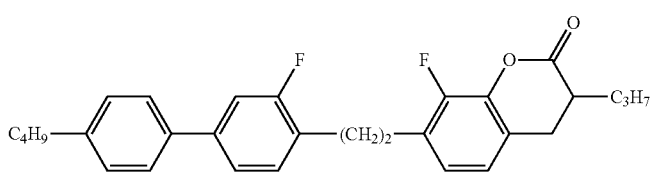
166
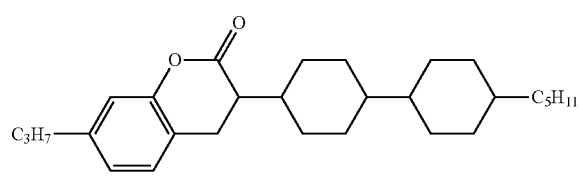
167
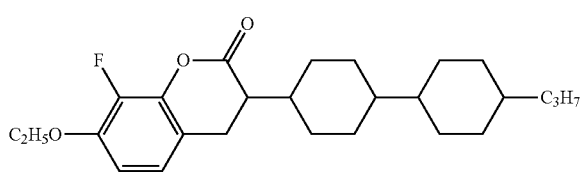
168
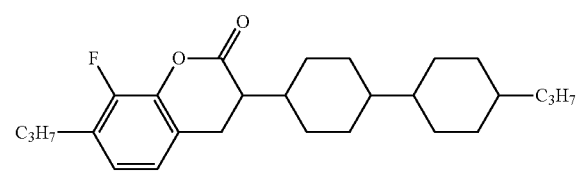
Δ ε: -6.80, Δ n: 0.143
169
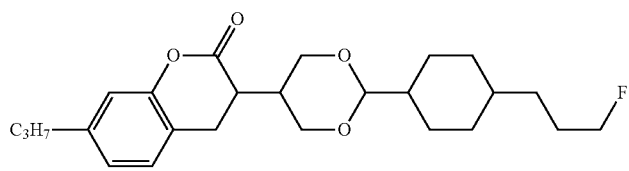

-continued
| No. | |
|---|---|
| 170 | 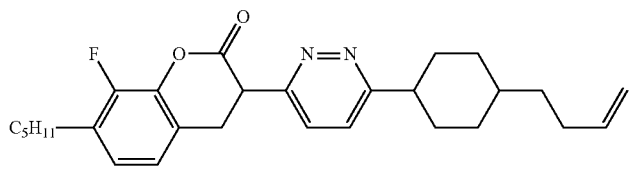 |
| 171 | 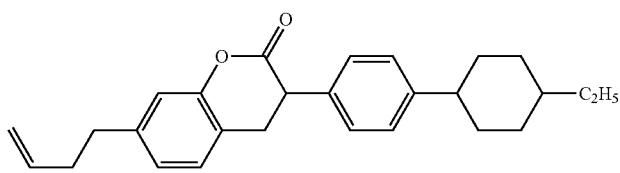 [SMILES: C=CCCc1ccc2c(c1)OC(=O)C(c1ccc(C3CCC(CC)CC3)cc1)C2] |
| 172 | 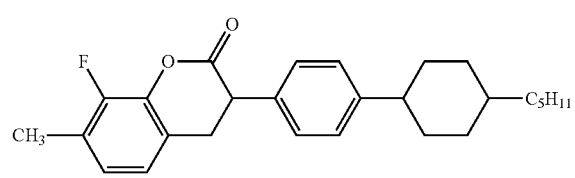 |
| 173 | 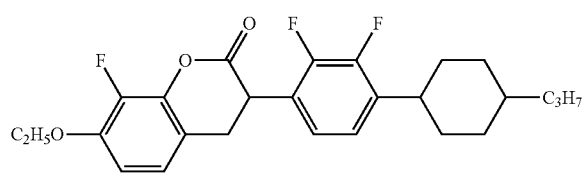 |
| 174 | 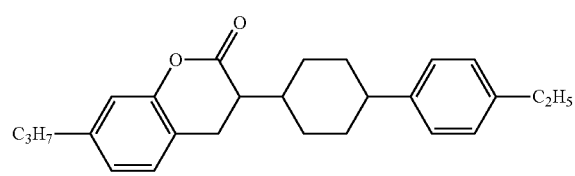 |
| 175 | 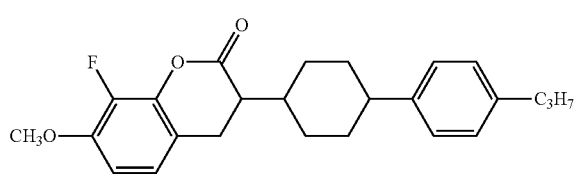 |
| 176 | 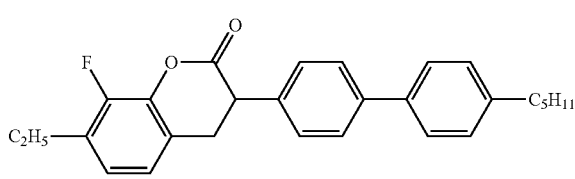 |
| 177 | 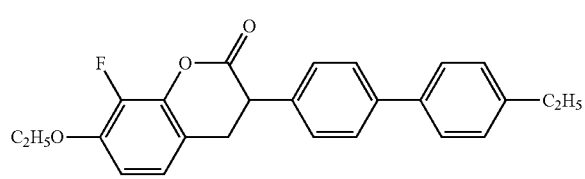 |
| 178 | 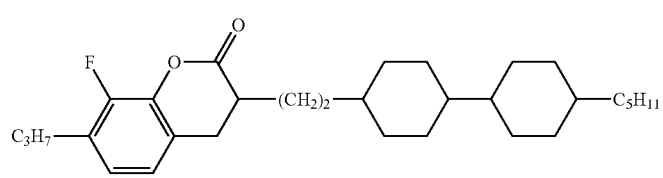 |

-continued
| No. | |
|---|---|
| 179 | 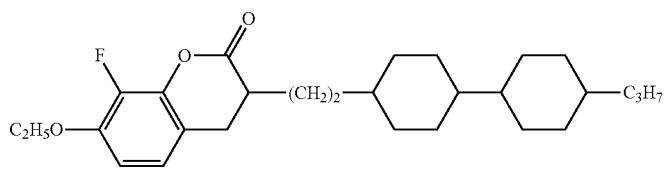 |
| 180 | 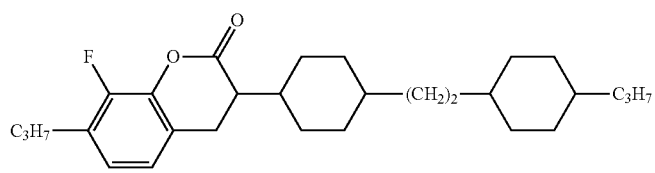 |
| 181 | 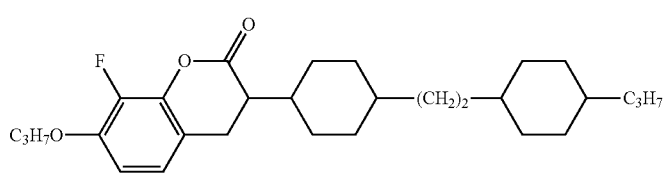 |
| 182 | 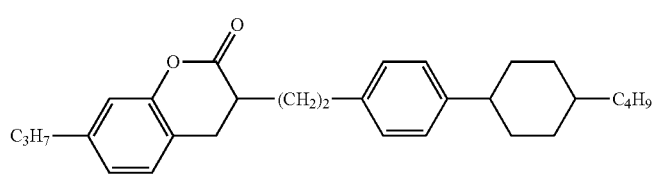 |
| 183 | 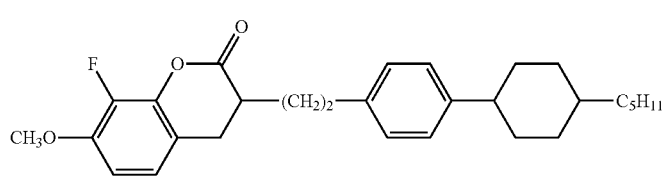 |
| 184 | 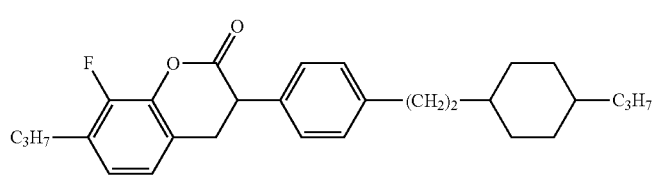 |
| 185 | 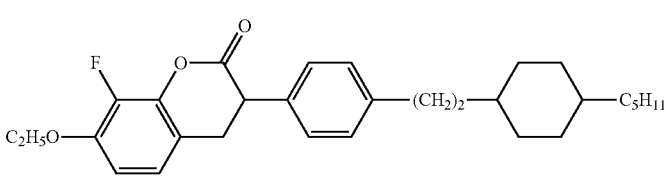 |
| 186 | 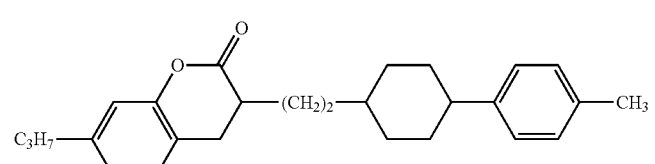 |
| 187 | 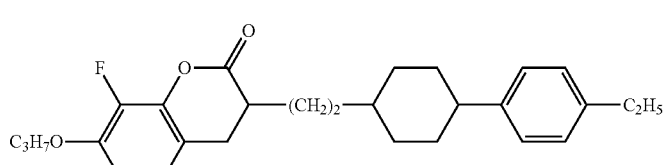 |

-continued
| No. | |
|---|---|
| 188 | 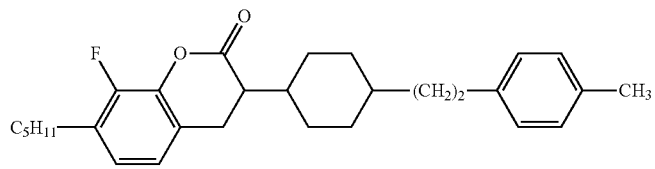 |
| 189 | 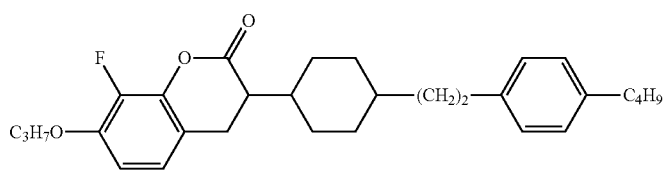 |
| 190 | 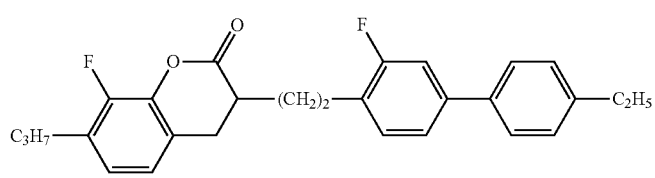 |
| 191 | 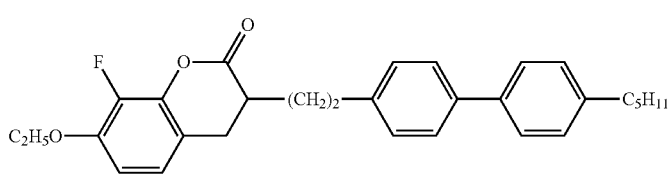 |
| 192 | 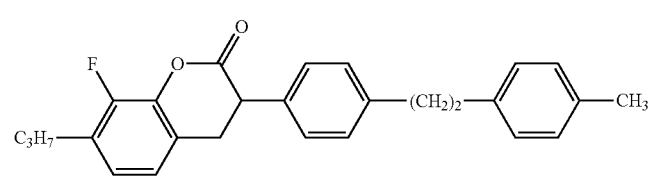 |
| 193 | 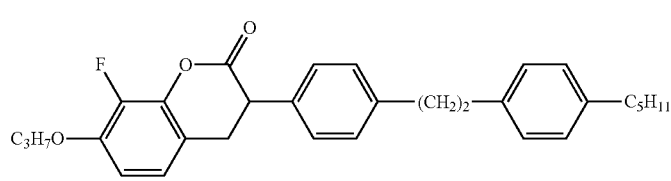 |
| 194 | 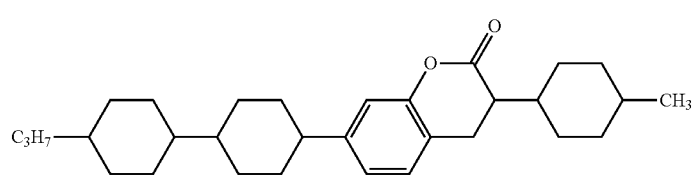 |
| 195 | 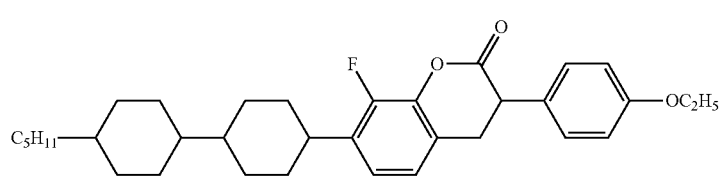 |
| 196 | 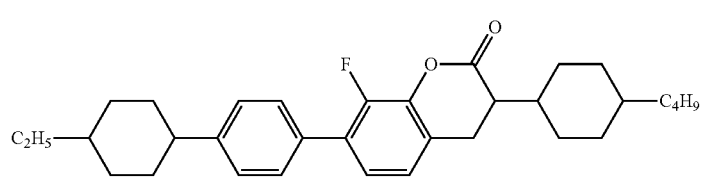 |

-continued
| No. | |
|---|---|
| 197 | 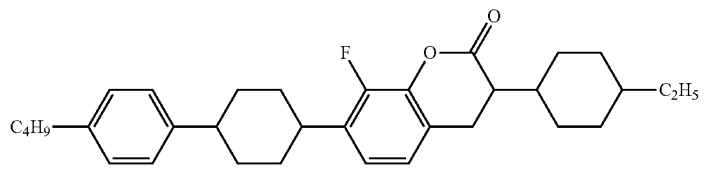 |
| 198 | 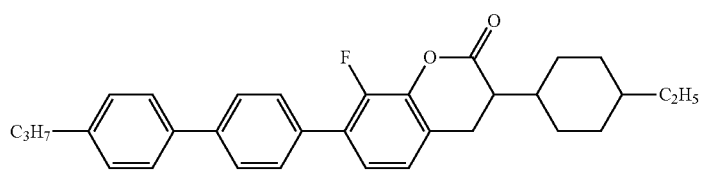 |
| 199 | 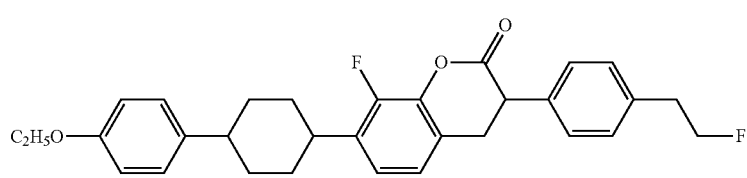 |
| 200 | 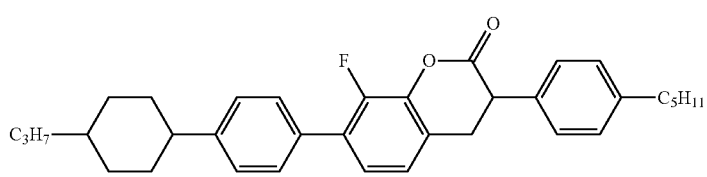 |
| 201 | 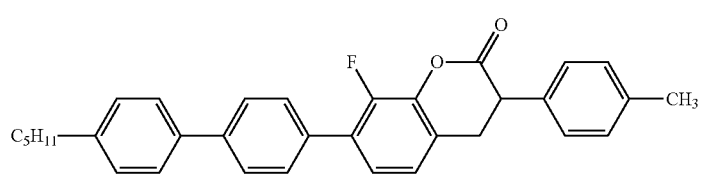 |
| 202 | 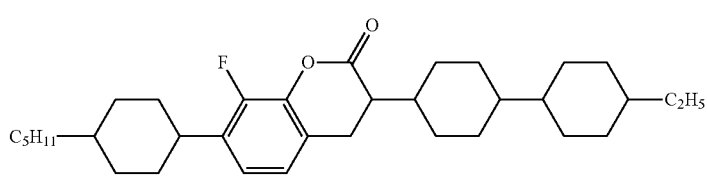 |
| 203 | 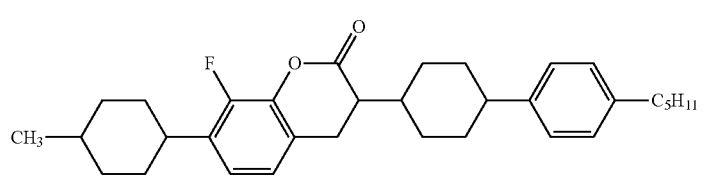 |
| 204 | 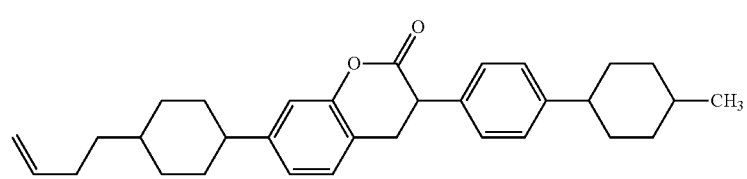 [SMILES: C=CCCC1CCC(c2ccc3c(c2)OC(=O)C(c2ccc(C4CCC(C)CC4)cc2)C3)CC1] |
| 205 | 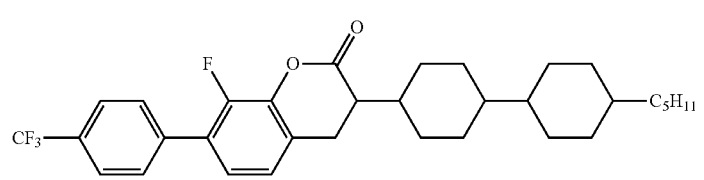 |

-continued
| No. | |
|---|---|
| 206 | 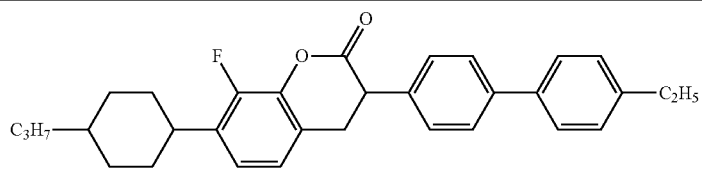 |
| 207 | 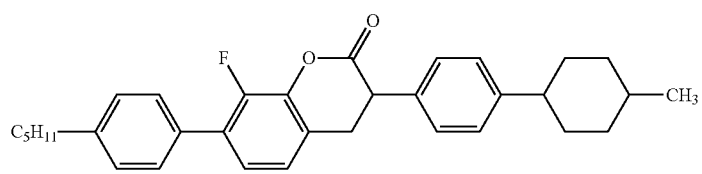 |
| 208 | 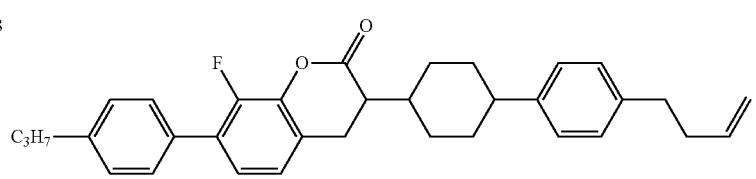 |
| 209 | 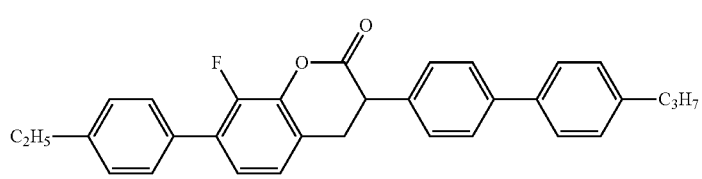 |
| 210 | 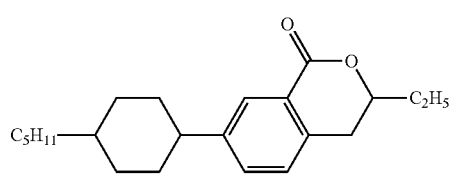 |
| 211 | 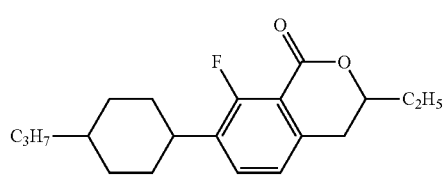 |
| 212 | 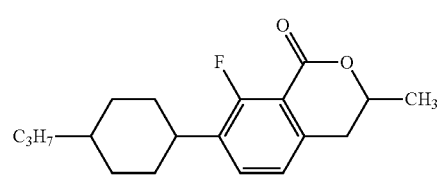 |
| 213 | 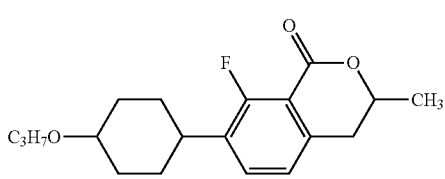 |
| 214 | 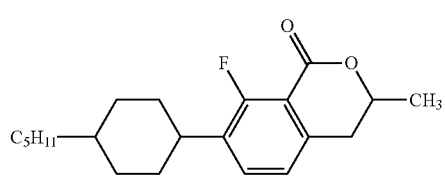 |

-continued
| No. | |
|---|---|
| 215 | 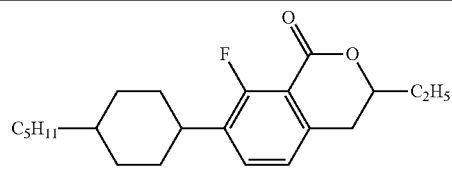 |
| 216 | 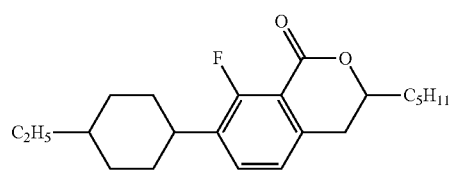 |
| 217 | 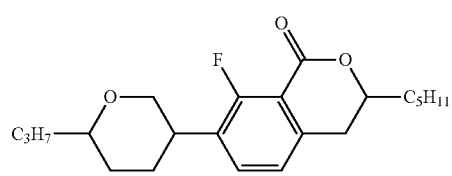 |
| 218 | 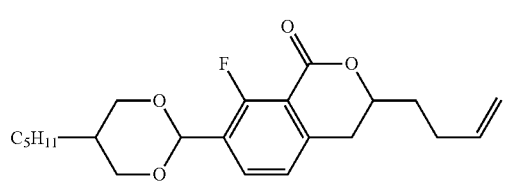 |
| 219 | 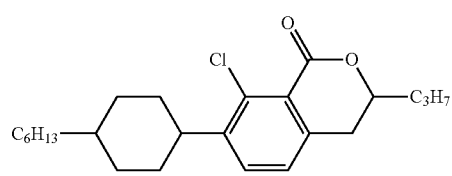 |
| 220 | 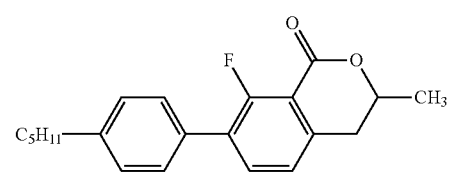 |
| 221 | 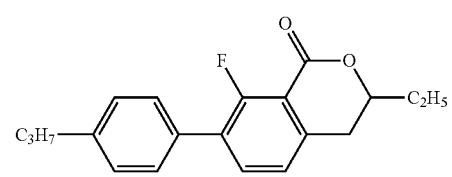 |
| 222 | 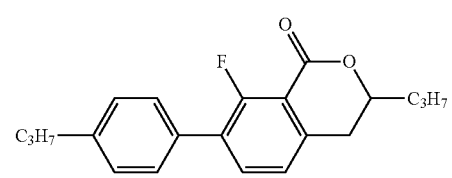 |
| 223 | 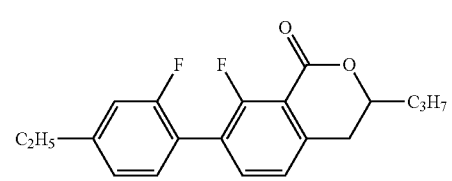 |

-continued
| No. | |
|---|---|
| 224 | 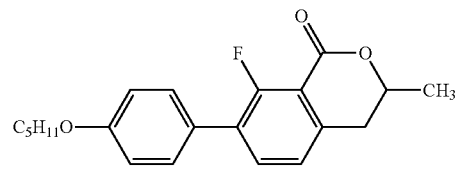 |
| 225 | 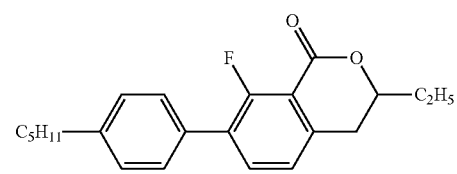 |
| 226 | 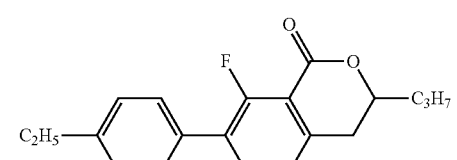 |
| 227 | 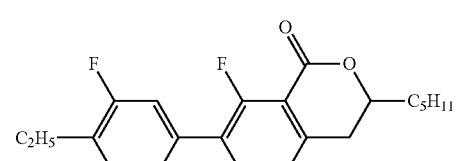 |
| 228 | 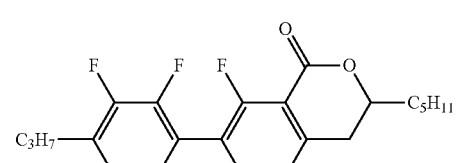 |
| 229 | 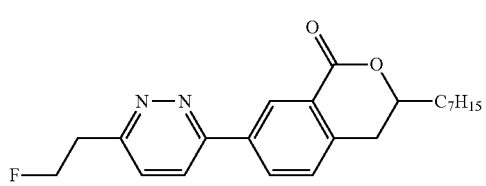 |
| 230 | 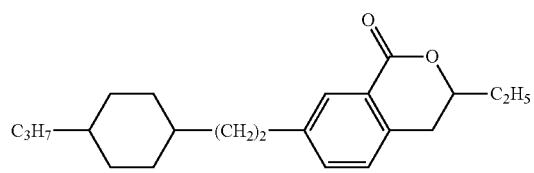 |
| 231 | 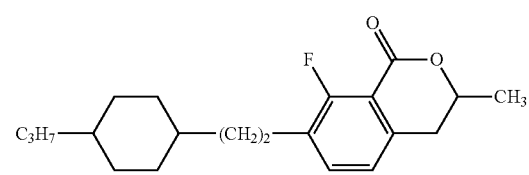 |
| 232 | 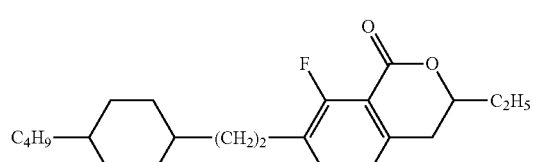 |

-continued
| No. | |
|---|---|
| 233 | 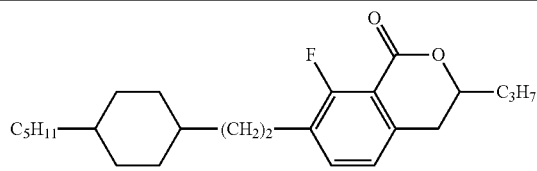 |
| 234 | 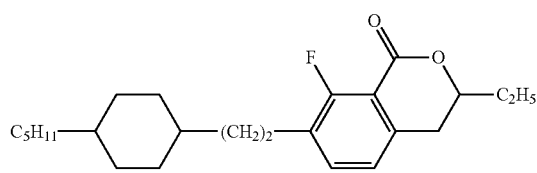 |
| 235 | 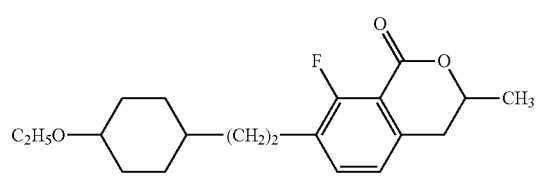 |
| 236 | 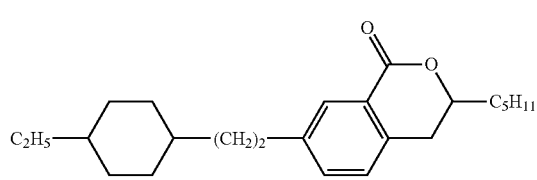 |
| 237 | 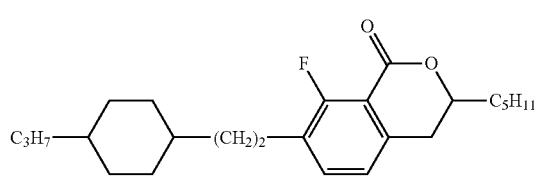 |
| 238 | 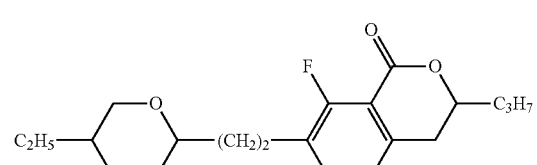 |
| 239 | 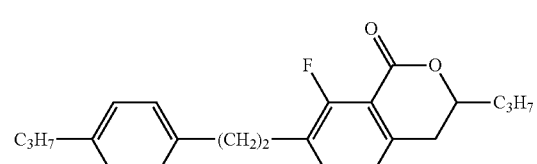 |
| 240 | 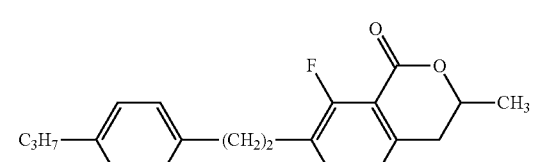 |
| 241 | 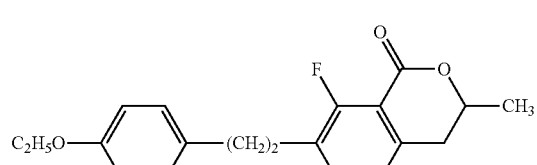 |

-continued
| No. | |
|---|---|
| 242 | 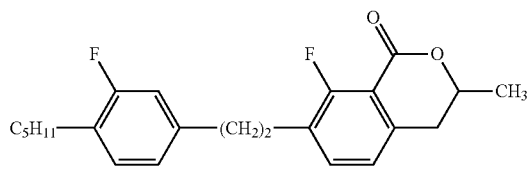 |
| 243 | 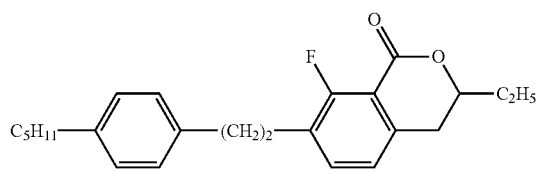 |
| 244 | 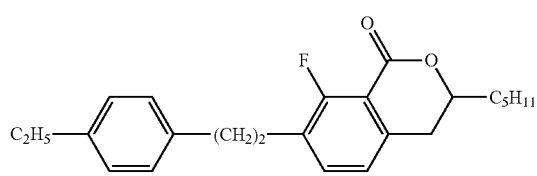 |
| 245 | 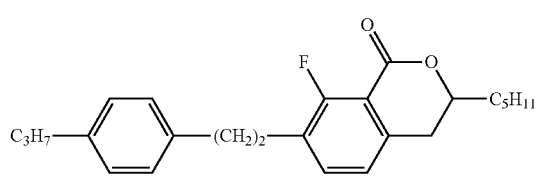 |
| 246 | 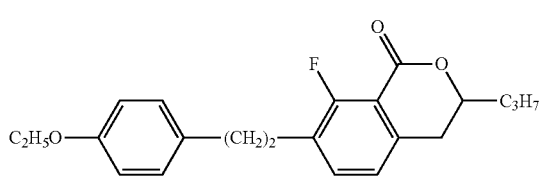 |
| 247 | 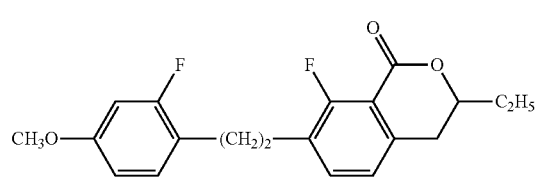 |
| 248 | 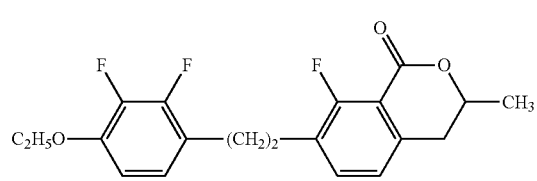 |
| 249 | 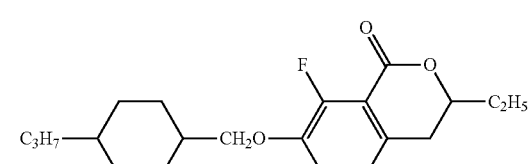 |
| 250 | 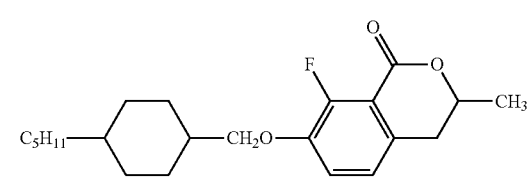 |

-continued
| No. | |
|---|---|
| 251 | 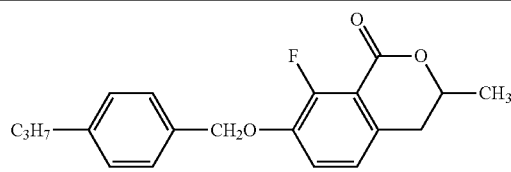 |
| 252 | 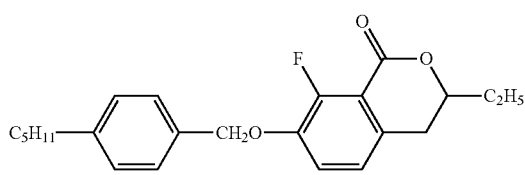 |
| 253 | 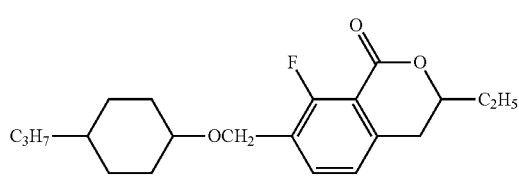 |
| 254 | 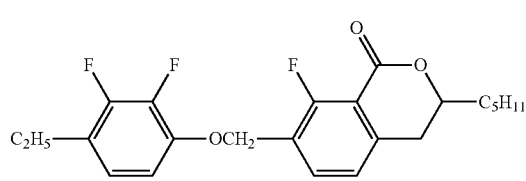 |
| 255 | 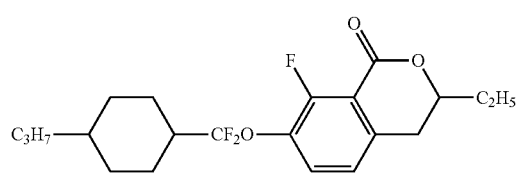 |
| 256 | 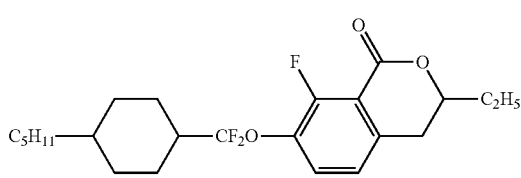 |
| 257 | 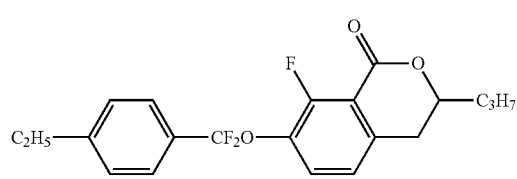 |
| 258 | 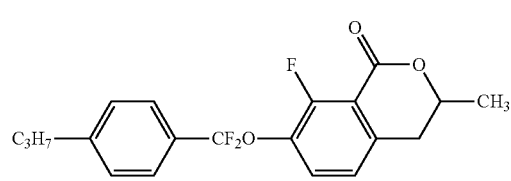 |
| 259 | 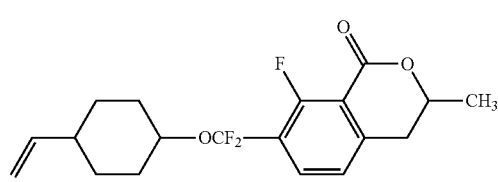 |

-continued
| No. | |
|---|---|
| 260 | 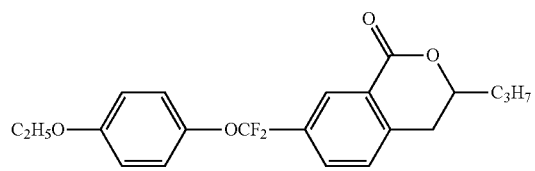 |
| 261 | 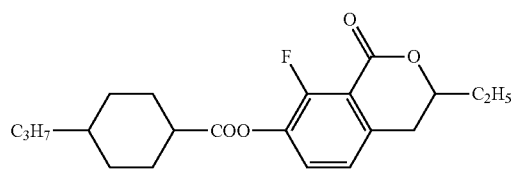 |
| 262 | 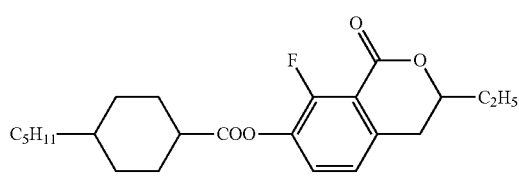 |
| 263 | 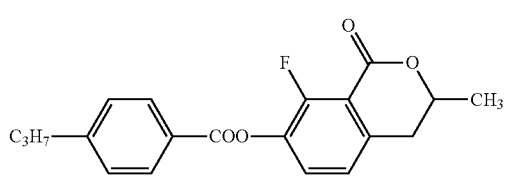 |
| 264 | 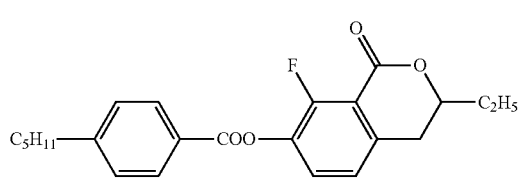 |
| 265 | 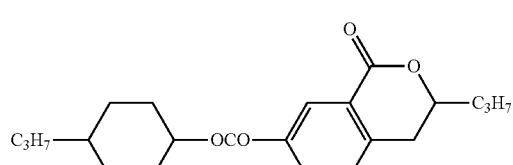 |
| 266 | 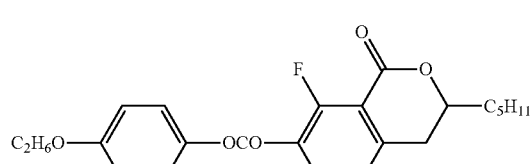 |
| 267 | 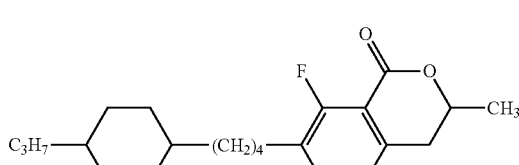 |
| 268 | 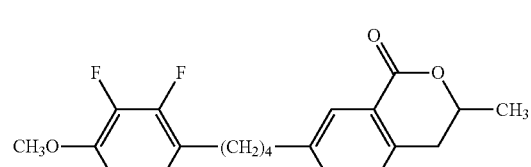 |

| No. | |
|---|---|
| 269 | 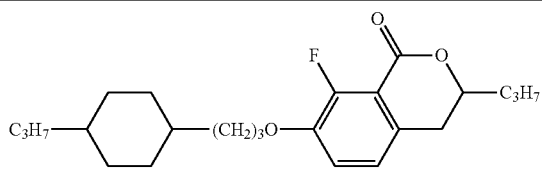 |
| 270 | 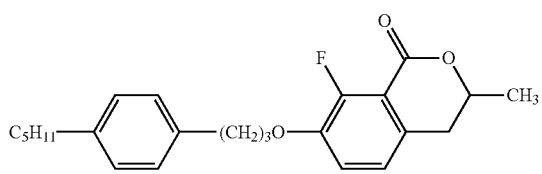 |
| 271 | 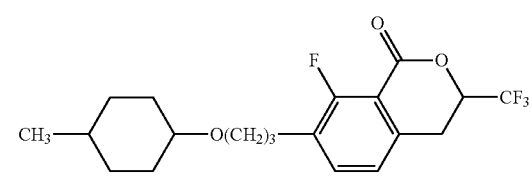 |
| 272 | 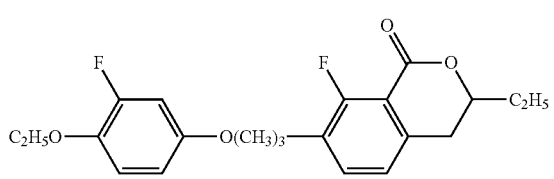 |
| 273 | 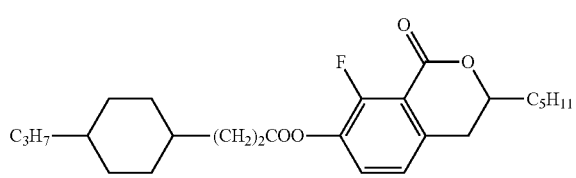 |
| 274 | 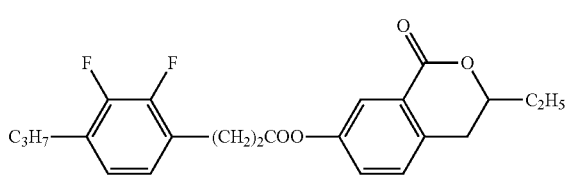 |
| 275 | 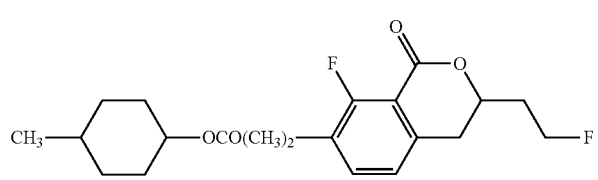 |
| 276 | 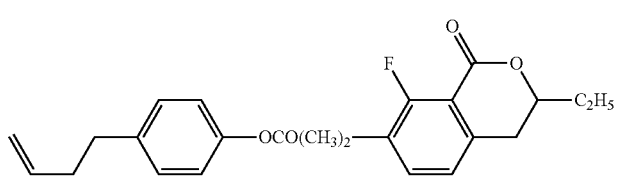 |
| 277 | 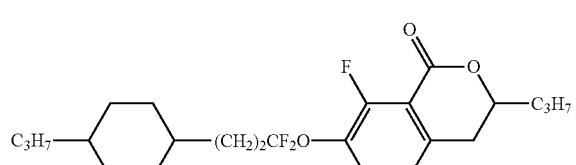 |

| No. | |
|---|---|
| 278 | 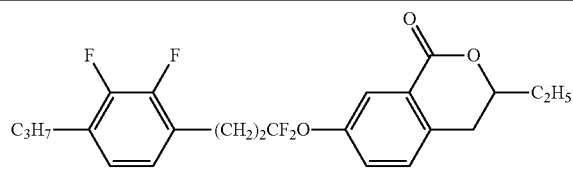 |
| 279 | 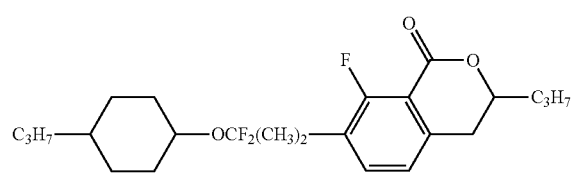 |
| 280 | 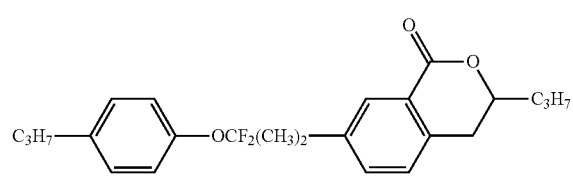 |
| 281 | 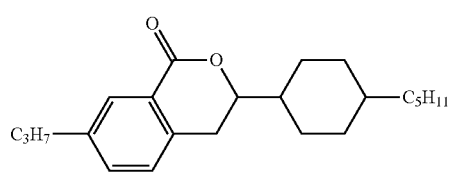 |
| 282 | 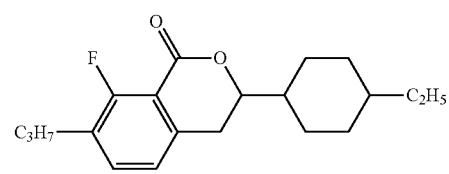 |
| 283 | 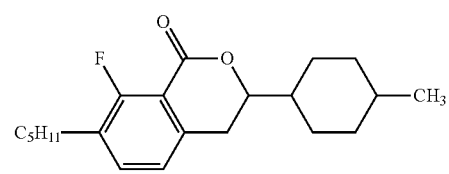 |
| 284 | 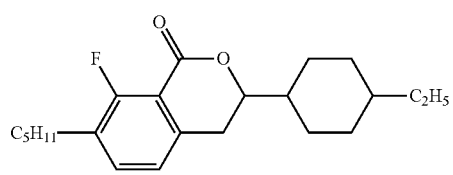 |
| 285 | 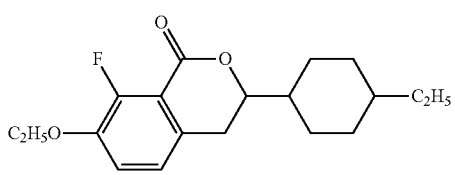 |
| 286 | 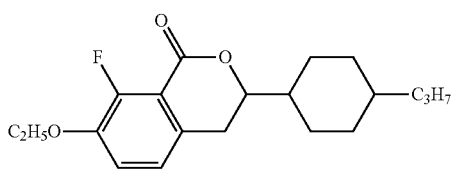 |

-continued
| No. | |
|---|---|
| 287 | 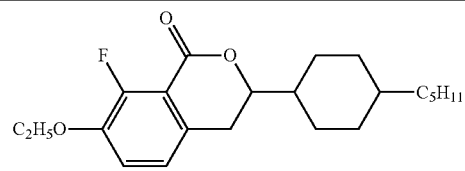 |
| 288 | 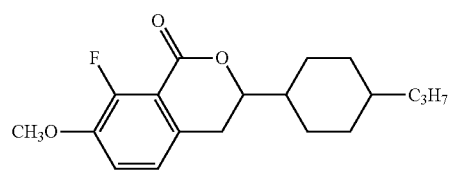 |
| 289 | 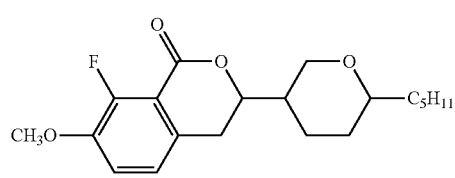 |
| 290 | 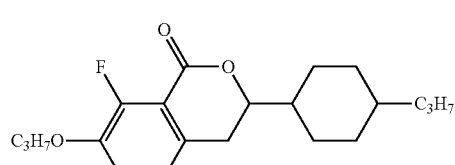 |
| 291 | 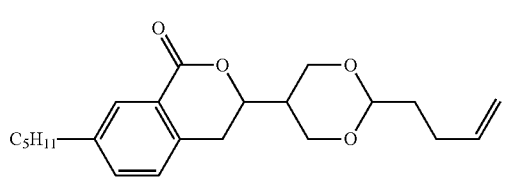 |
| 292 | 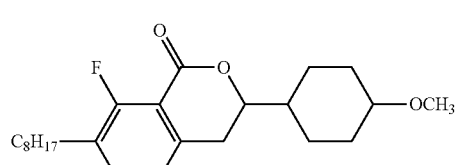 |
| 293 | 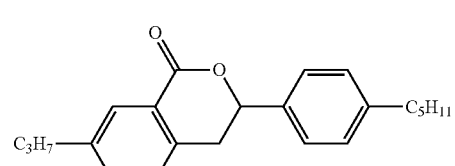 |
| 294 | 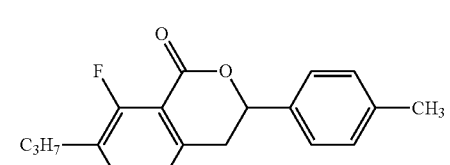 |
| 295 | 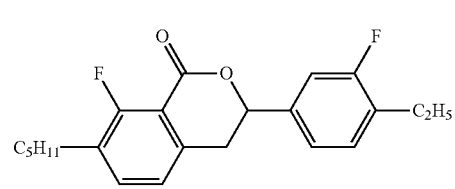 |

-continued
| No. | |
|---|---|
| 296 | 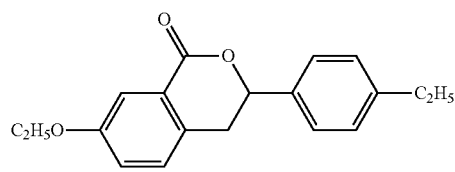 |
| 297 | 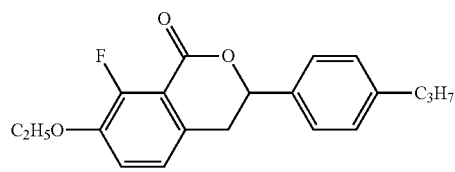 |
| 298 | 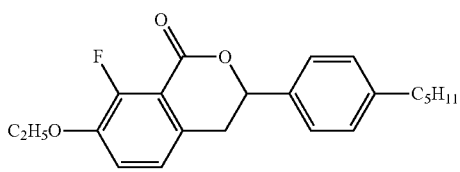  C 78.1 I  Δ ε: -20.61, Δ n: 0.106 |
| 299 | 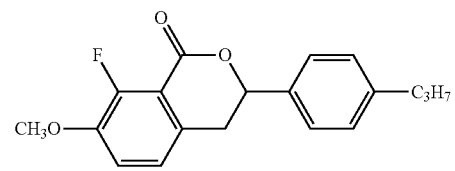 |
| 300 | 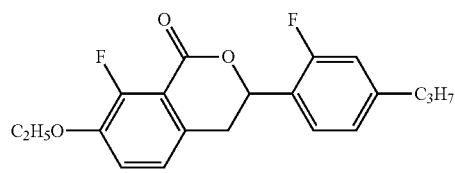 |
| 301 | 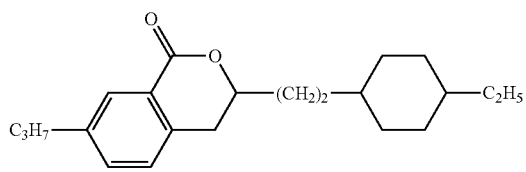 |
| 302 | 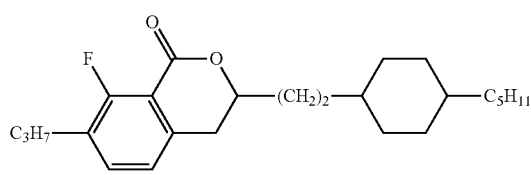 |
| 303 | 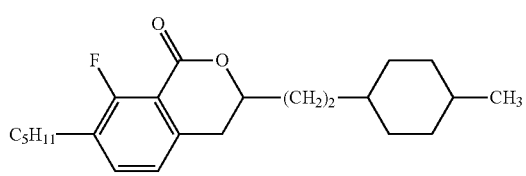 |

-continued
| No. | |
|---|---|
| 304 | 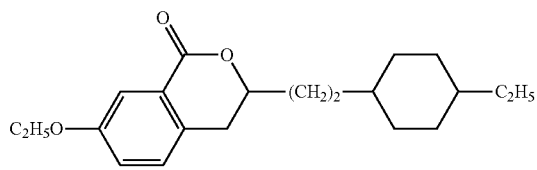 |
| 305 | 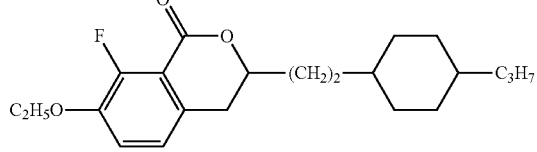 |
| 306 | 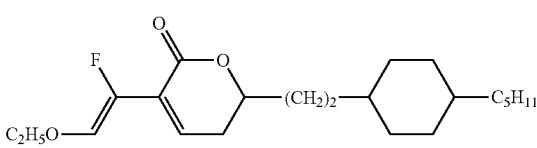 |
| 307 | 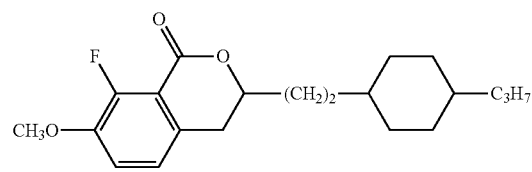 |
| 308 | 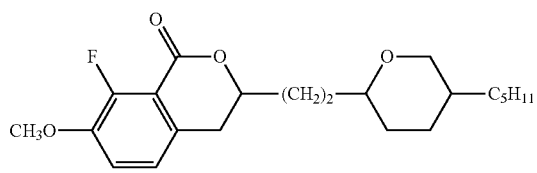 |
| 309 | 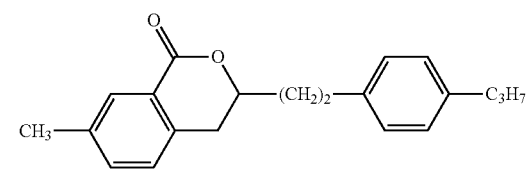 |
| 310 | 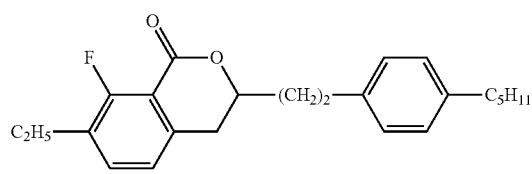 |
| 311 | 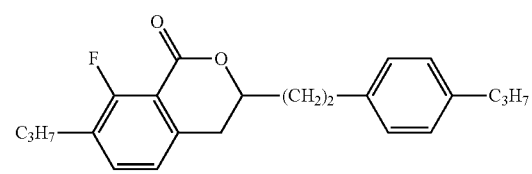 |
| 312 | 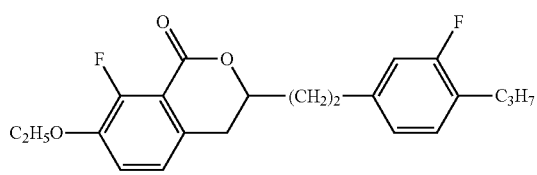 |

-continued
| No. | |
|---|---|
| 313 | 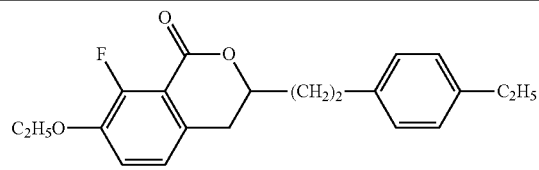 |
| 314 | 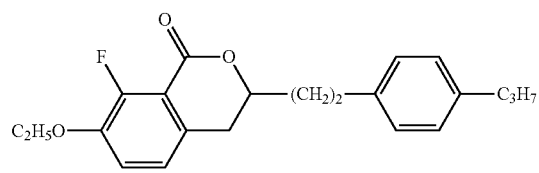 |
| 315 | 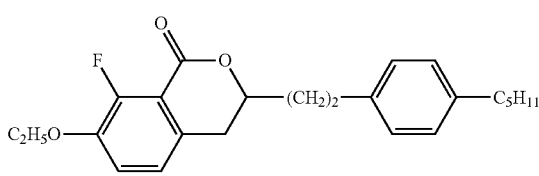 |
| 316 | 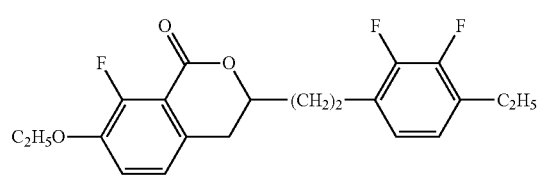 |
| 317 | 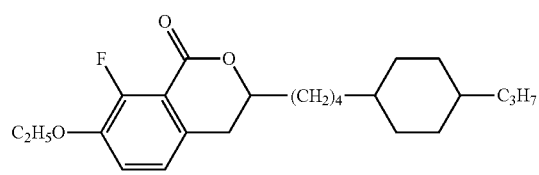 |
| 318 | 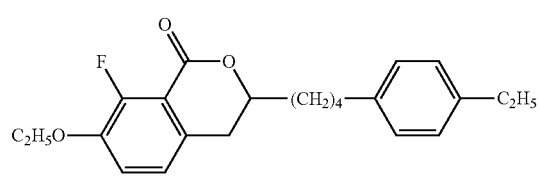 |
| 319 | 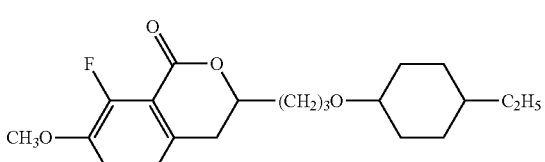 |
| 320 | 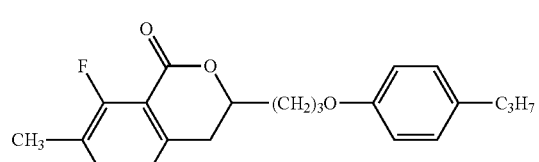 |
| 321 | 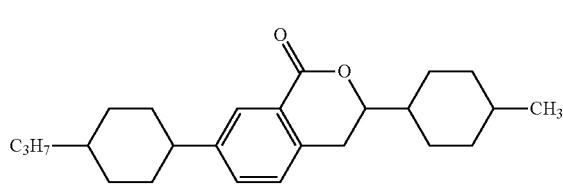 |

| No. | |
|---|---|
| 322 | 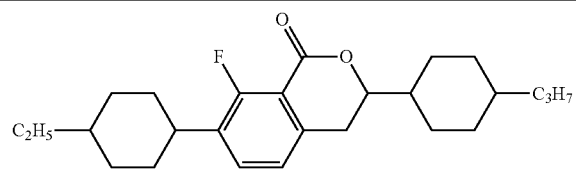 |
| 323 | 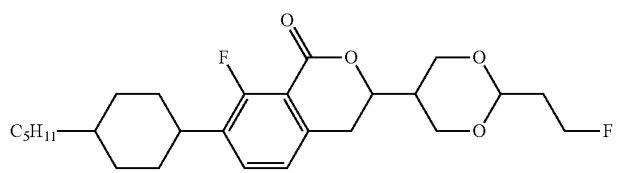 |
| 324 | 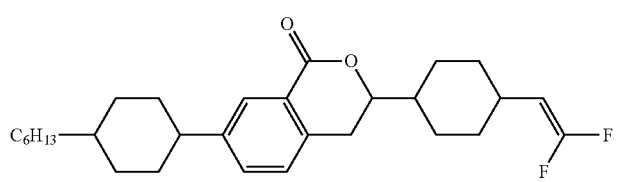 |
| 325 | 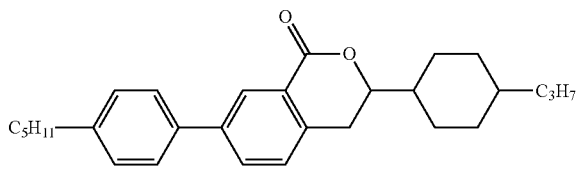 |
| 326 | 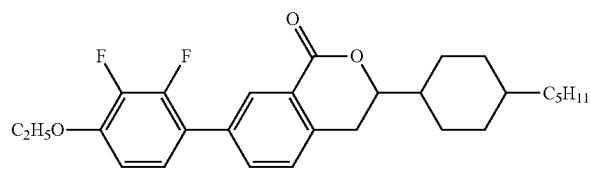 |
| 327 | 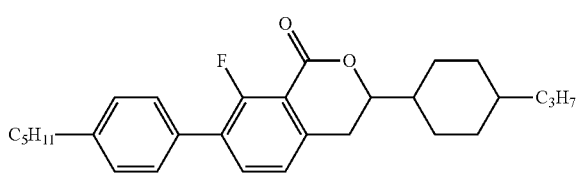 |
| 328 | 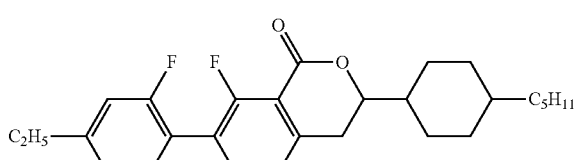 |
| 329 | 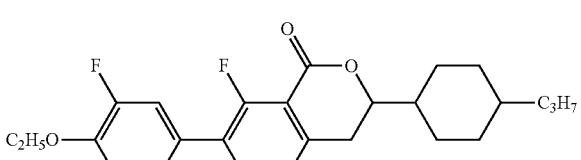 |
| 330 | 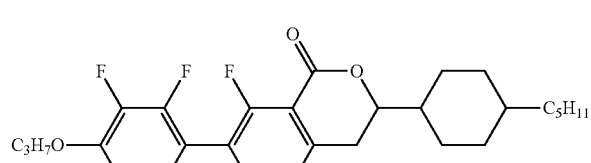 |

-continued
| No. | |
|---|---|
| 331 | 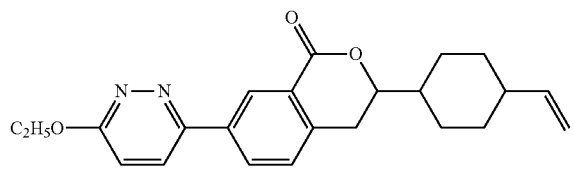 |
| 332 | 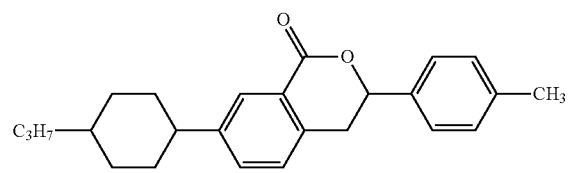 |
| 333 | 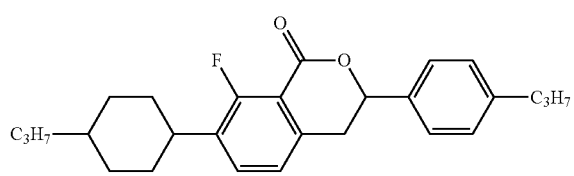 |
| 334 | 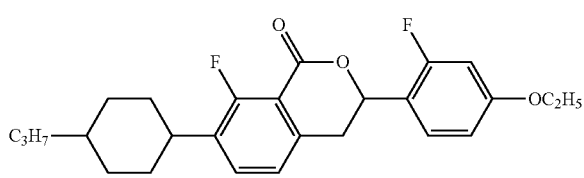 |
| 335 | 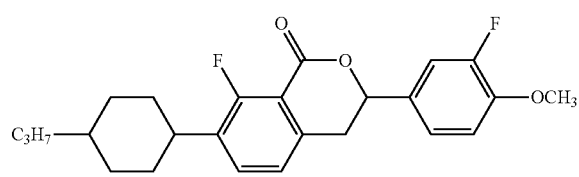 |
| 336 | 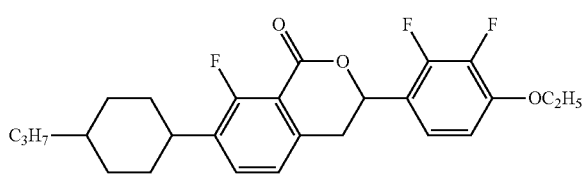 |
| 337 | 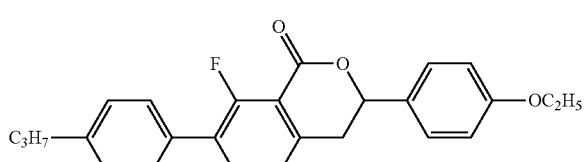 |
| 338 | 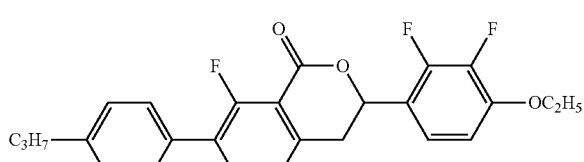 |
| 339 | 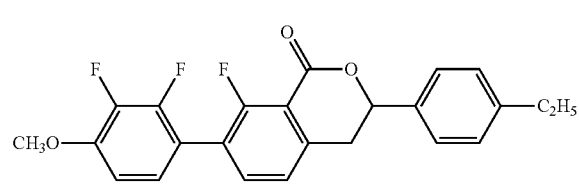 |

-continued
| No. | |
|---|---|
| 340 | 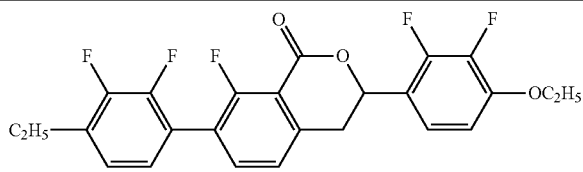 |
| 341 | 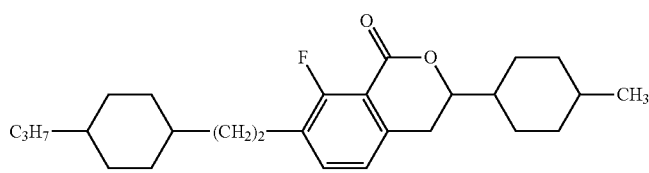 |
| 342 | 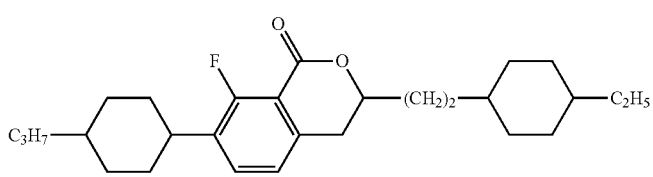 |
| 343 | 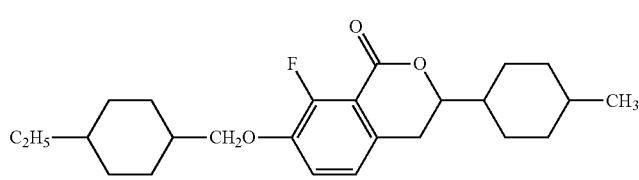 |
| 344 | 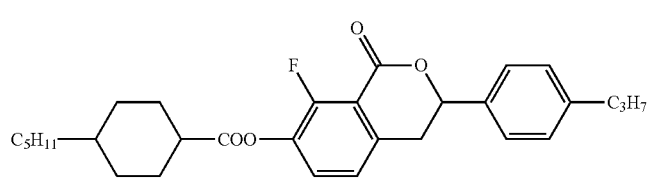 |
| 345 | 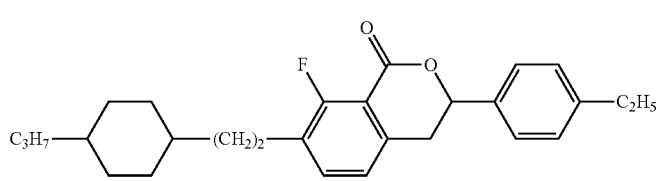 |
| 346 | 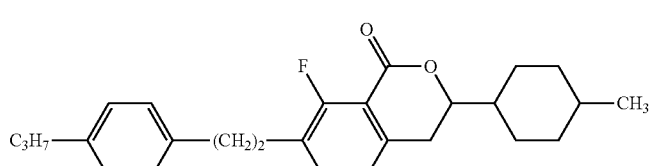 |
| 347 | 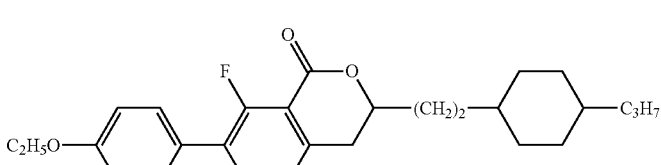 |
| 348 | 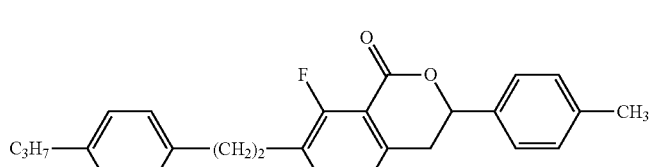 |

-continued
| No. | |
|---|---|
| 349 | 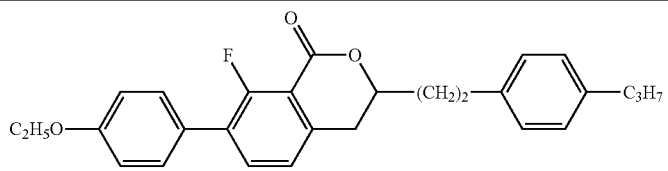 |
| 350 | 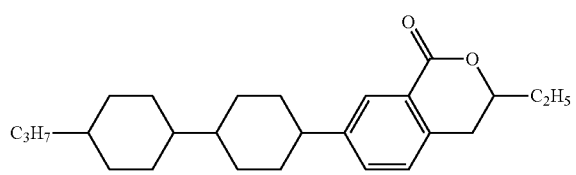 |
| 351 | 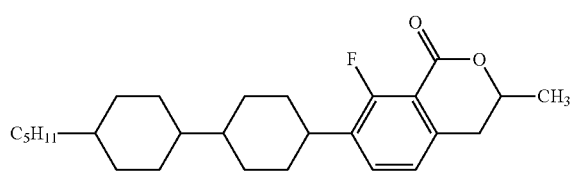 |
| 352 | 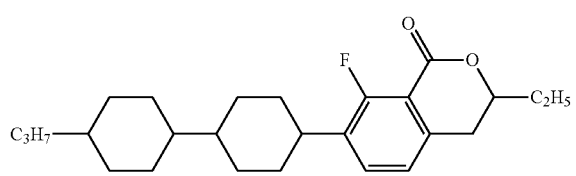 |
| 353 | 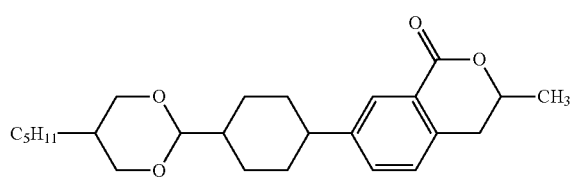 |
| 354 | 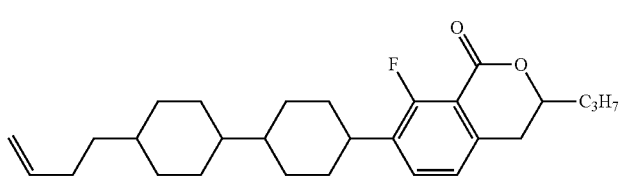 |
| 355 | 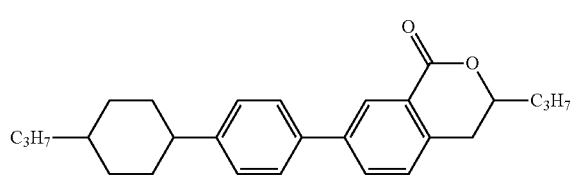 |
| 356 | 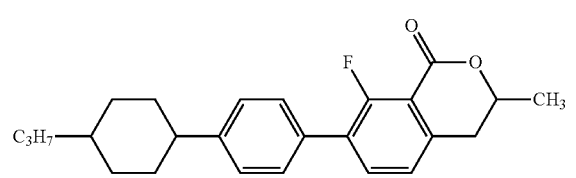 |
| 357 | 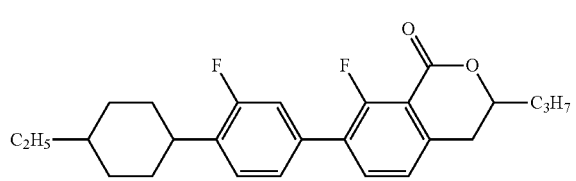 |

-continued
| No. | |
|---|---|
| 358 | 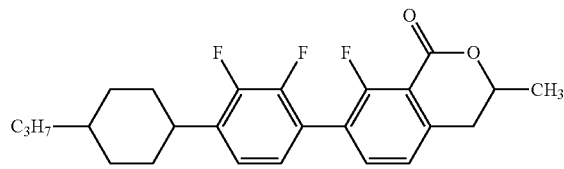 |
| 359 | 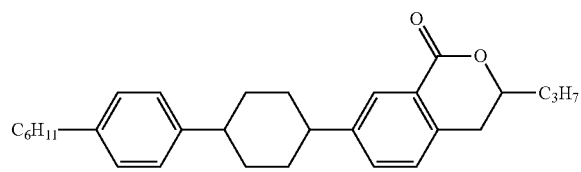 |
| 360 | 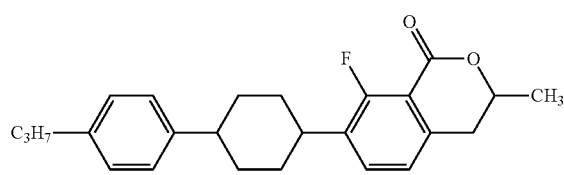 |
| 361 | 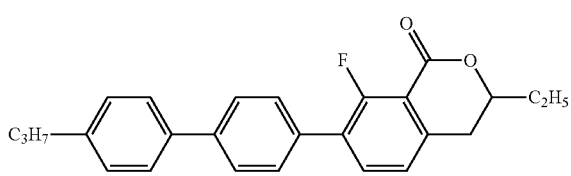 |
| 362 | 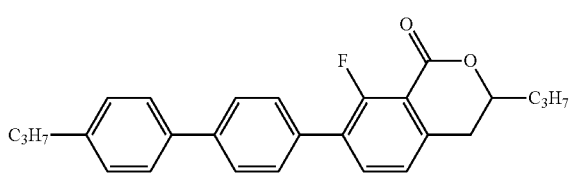 |
| 363 | 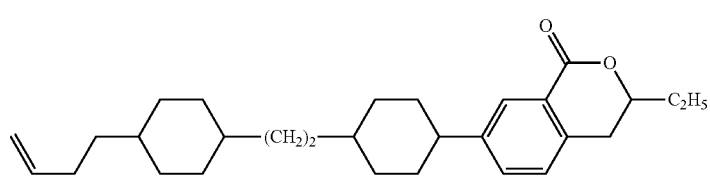 |
| 364 | 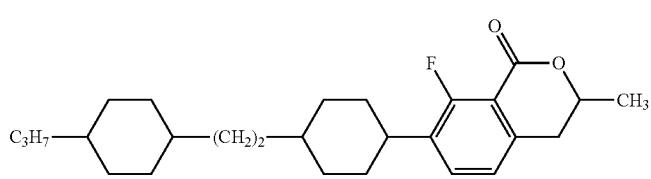 |
| 365 | 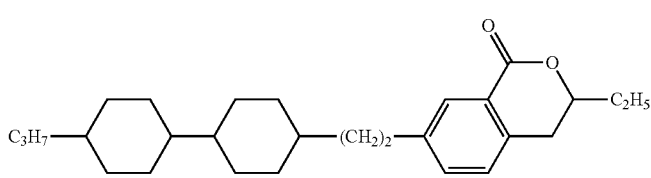 |
| 366 | 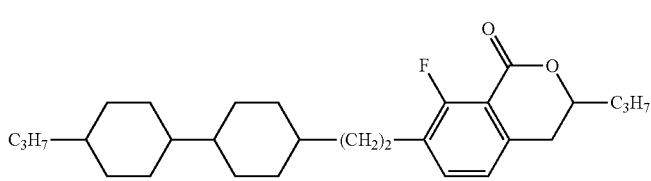 |

-continued
| No. | |
|---|---|
| 367 | 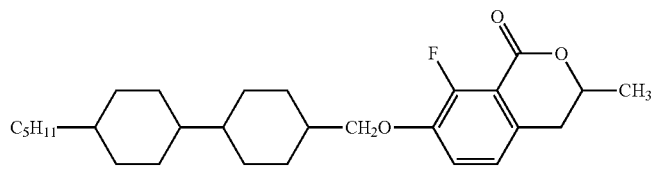 |
| 368 | 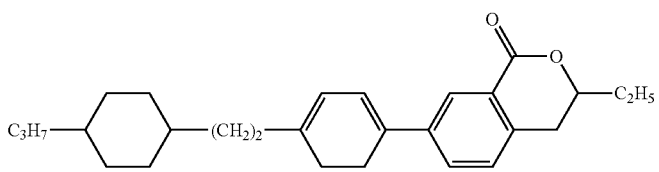 |
| 369 | 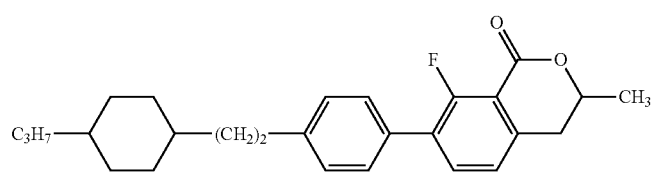 |
| 370 | 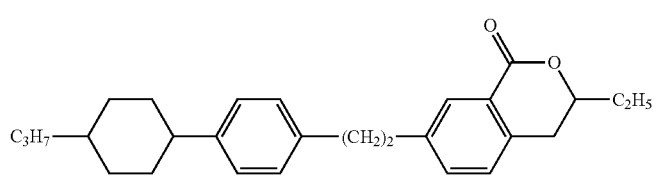 |
| 371 | 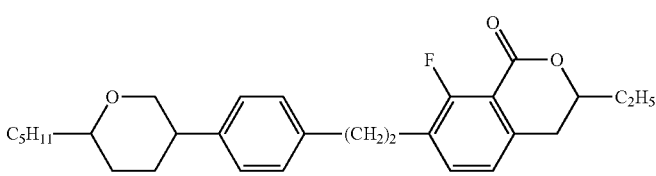 |
| 372 | 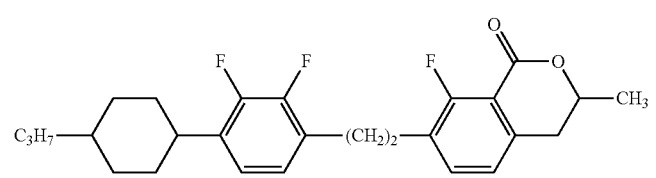 |
| 373 | 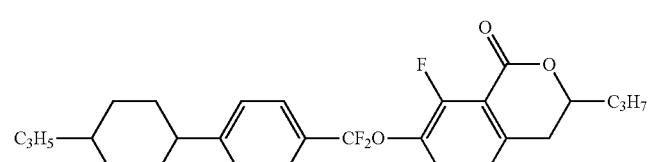 |
| 374 | 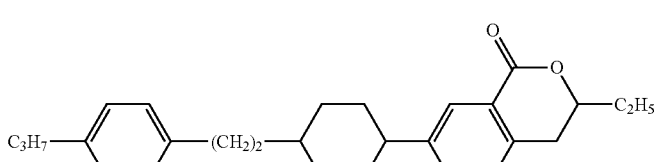 |
| 375 | 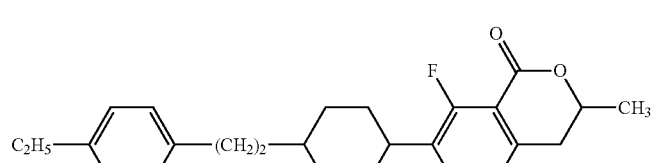 |

-continued
| No. | |
|---|---|
| 376 | 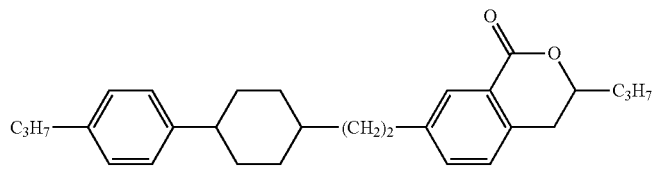 |
| 377 | 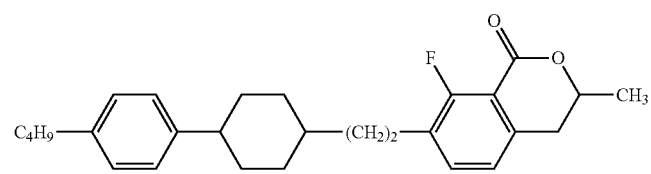 |
| 378 | 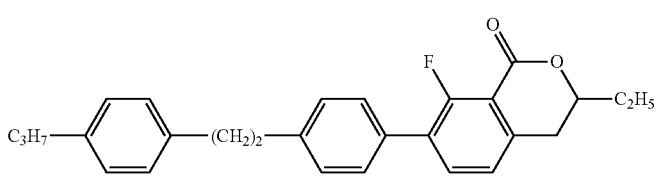 |
| 379 | 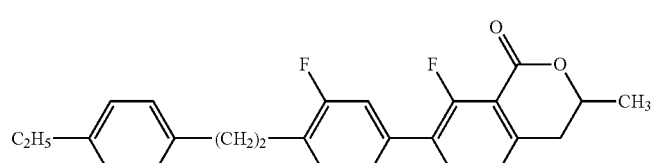 |
| 380 | 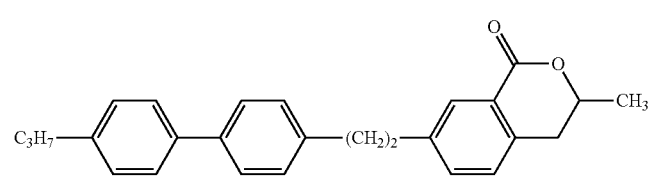 |
| 381 | 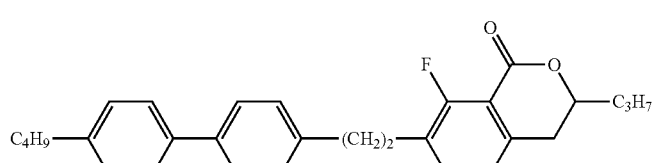 |
| 382 | 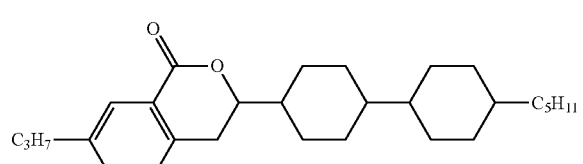 |
| 383 | 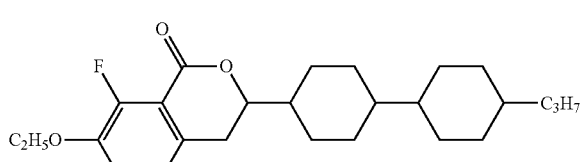 |
| 384 | 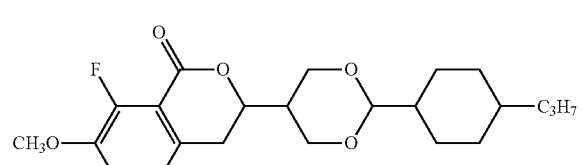 |

-continued
| No. | |
|---|---|
| 385 | 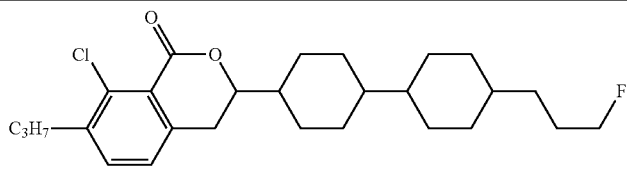 |
| 386 | 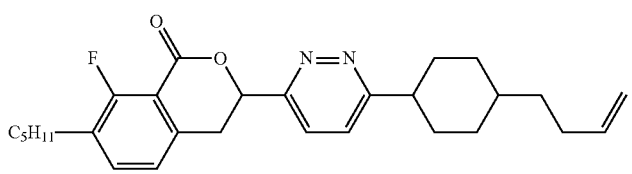 |
| 387 | 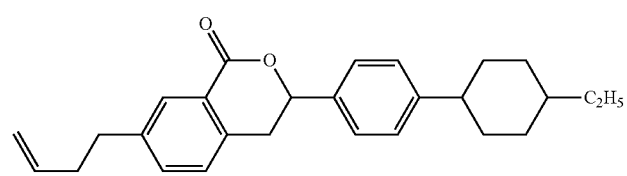 |
| 388 | 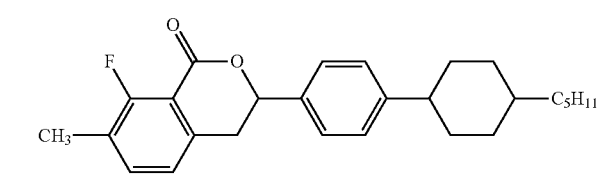 |
| 389 | 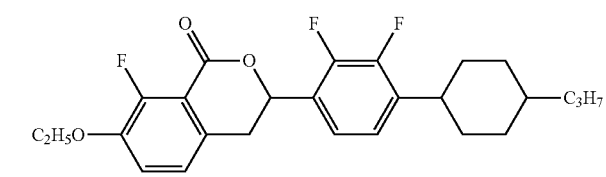 |
| 390 | 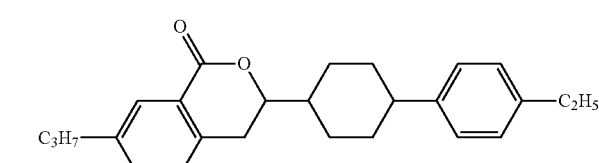 |
| 391 | 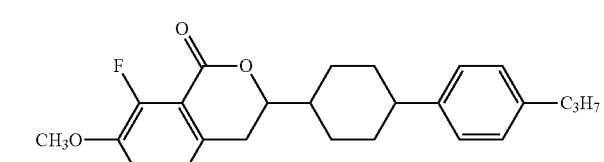 |
| 392 | 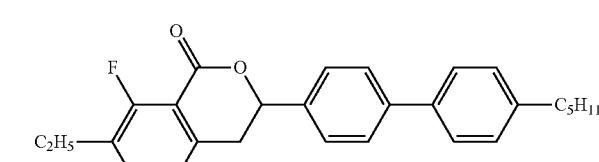 |
| 393 | 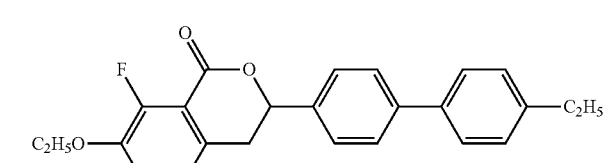 |

| No. | |
|---|---|
| 394 | 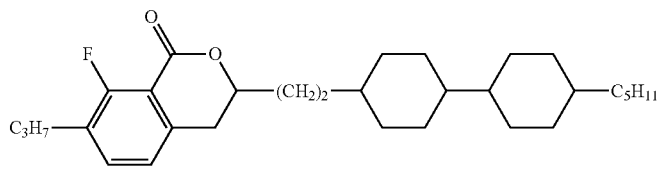 |
| 395 | 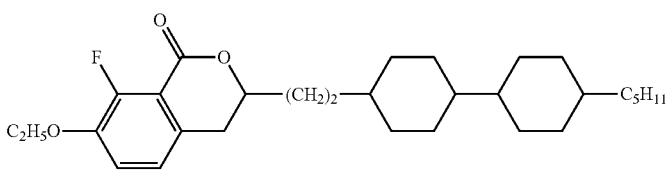 |
| 396 | 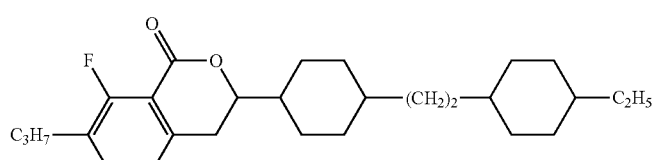 |
| 397 | 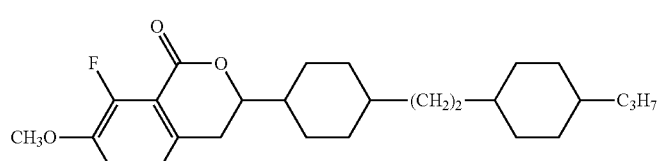 |
| 398 | 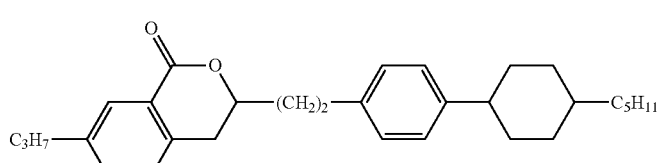 |
| 399 | 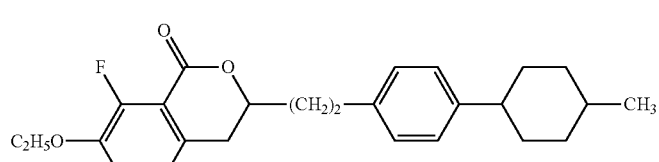 |
| 400 | 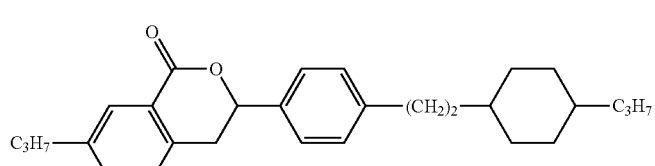 |
| 401 | 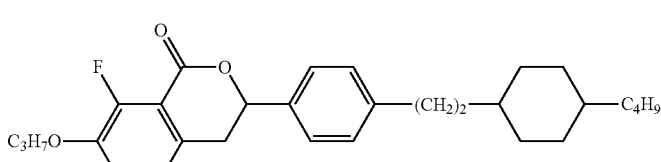 |
| 402 | 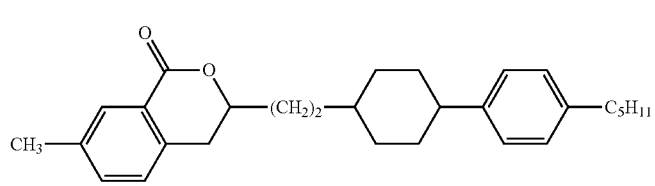 |

-continued
| No. | |
|---|---|
| 403 | 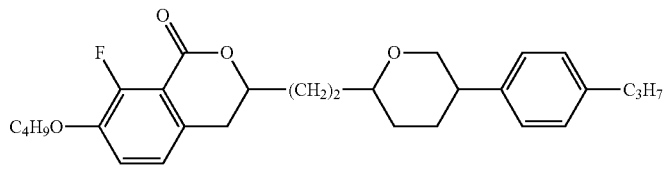 |
| 404 | 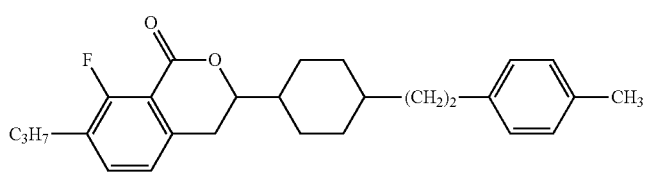 |
| 405 | 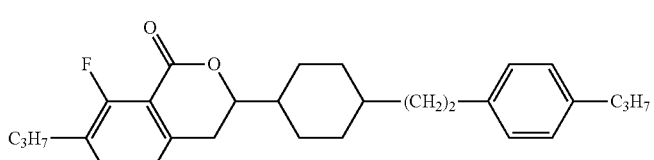 |
| 406 | 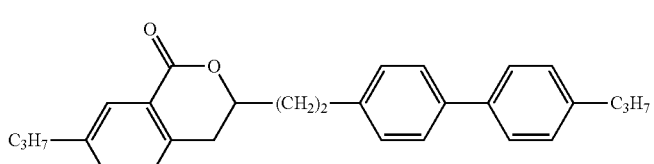 |
| 407 | 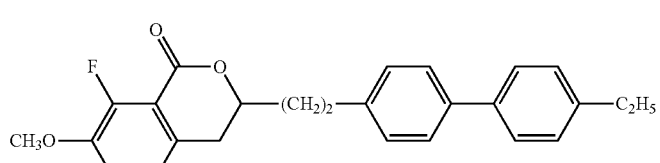 |
| 408 | 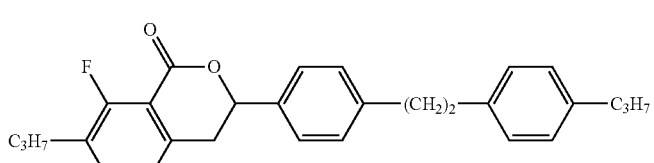 |
| 409 | 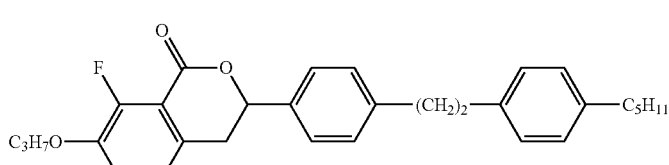 |
| 410 | 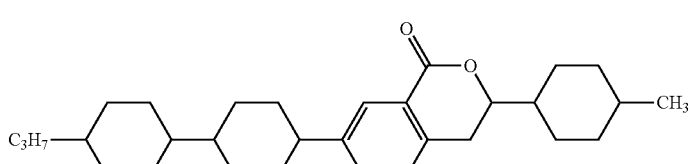 |
| 411 | 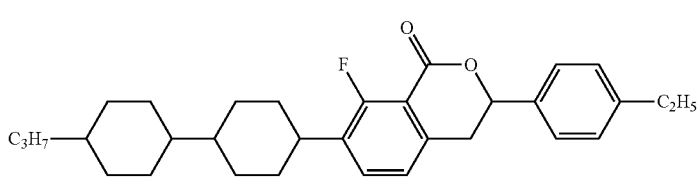 |

-continued
| No. | |
|---|---|
| 412 | 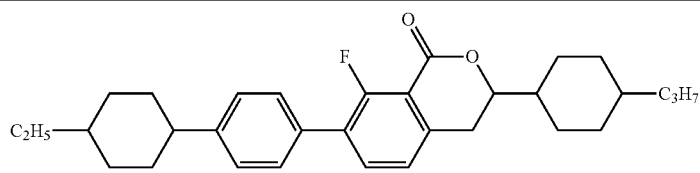 |
| 413 | 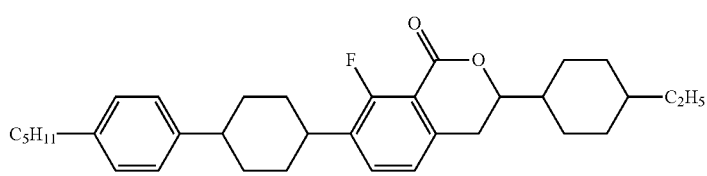 |
| 414 | 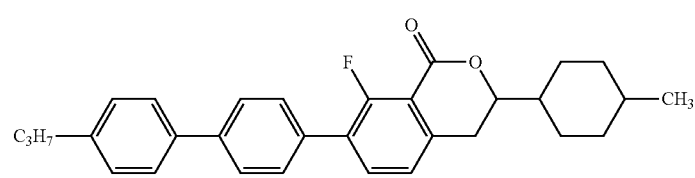 |
| 415 | 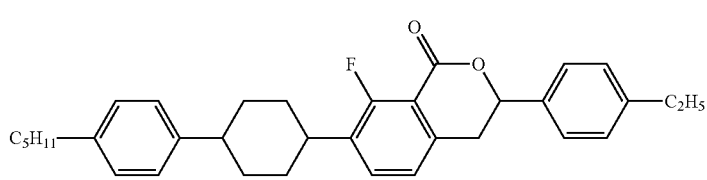 |
| 416 | 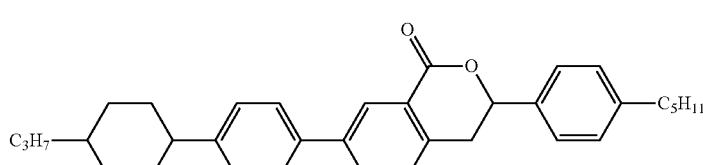 |
| 417 | 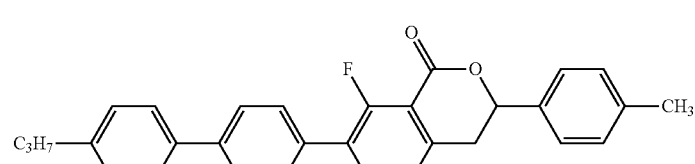 |
| 418 | 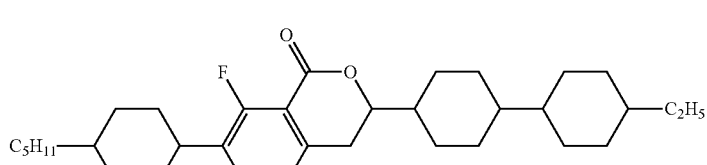 |
| 419 | 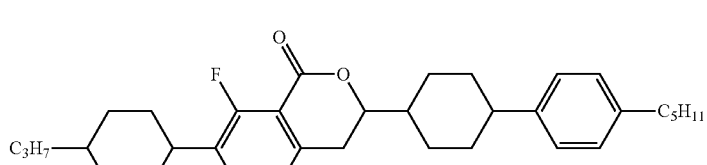 |
| 420 | 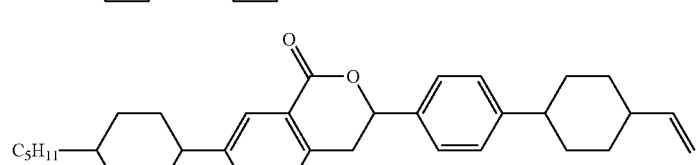 |

-continued
| No. | |
|---|---|
| 421 | 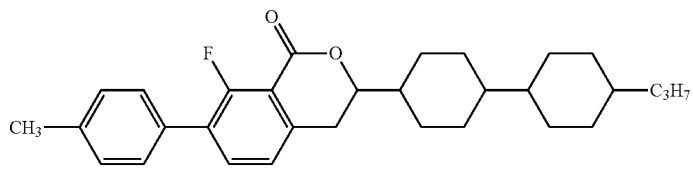 |
| 422 | 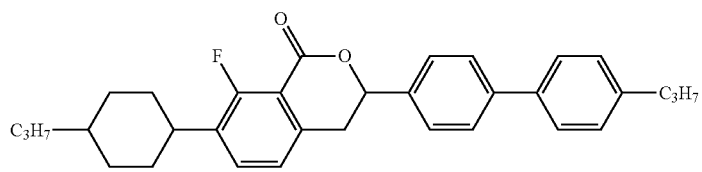 |
| 423 | 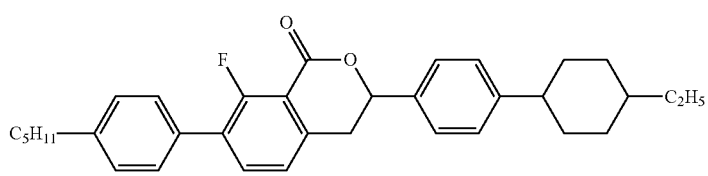 |
| 424 | 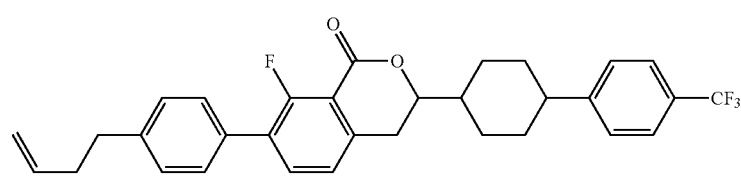 [SMILES: C=CCCc1ccc(-c2ccc3c(c2F)C(=O)OC(C2CCC(c4ccc(C(F)(F)F)cc4)CC2)C3)cc1] |
| 425 | 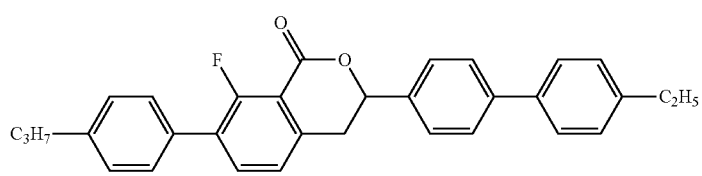 |
| 426 | 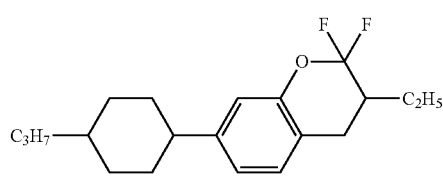 |
| 427 | 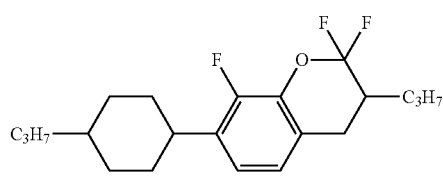 |
| 428 | 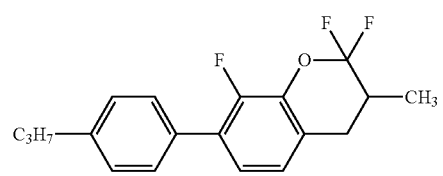 |
| 429 | 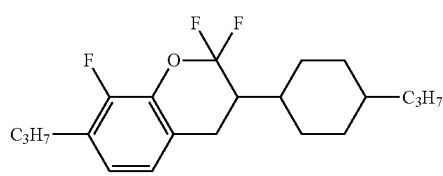 |

-continued
| No. | |
|---|---|
| 430 | 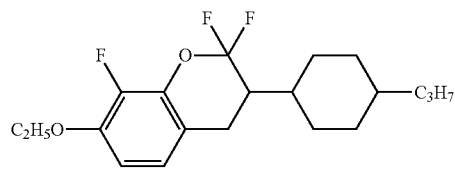 |
| 431 | 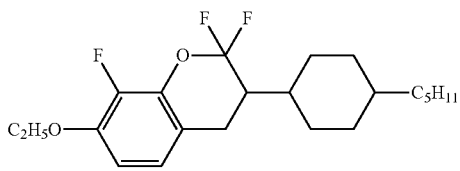 |
| 432 | 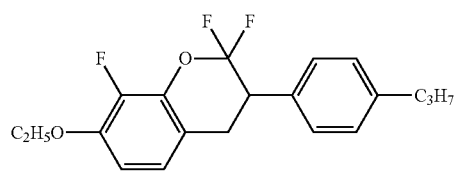 |
| 433 | 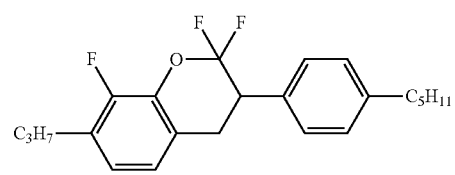 |
| 434 | 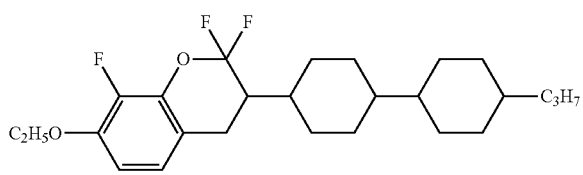 |
| 435 | 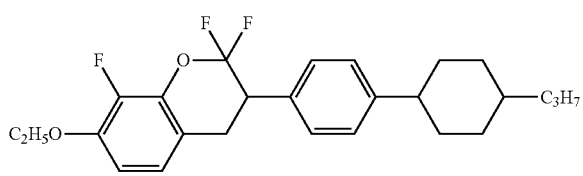 |
| 436 | 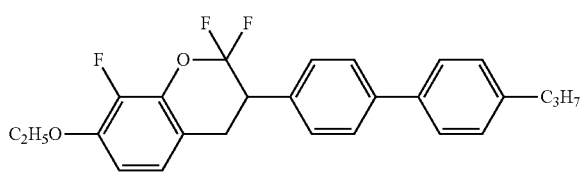 |
| 437 | 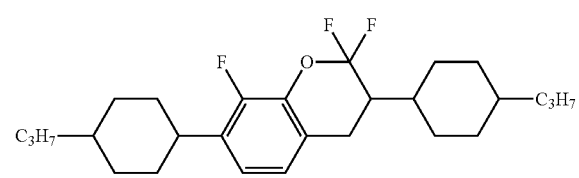 |
Δ ε: -6.10, Δ n: 0.099

| No. |
|---|
| 438 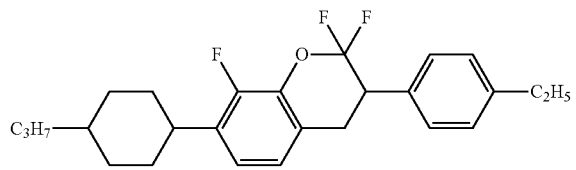 |
| 439 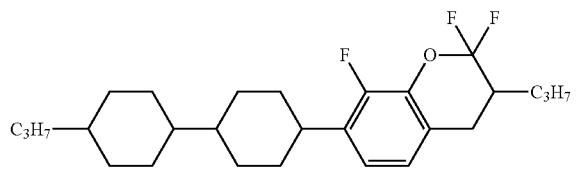<br>Δ ε: -6.45, Δ n: 0.099 |
| 440 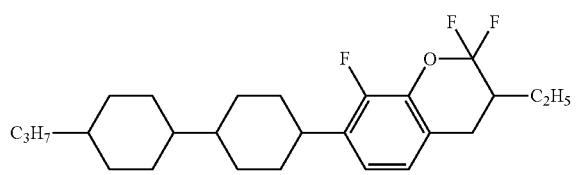 |
| 441 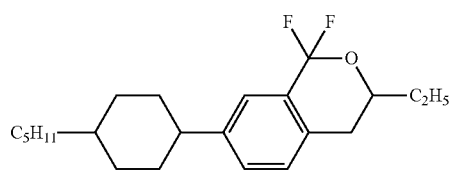 |
| 442 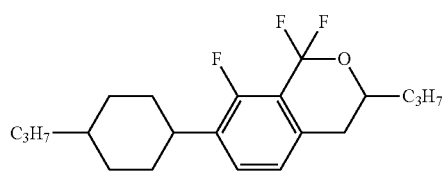 |
| 443 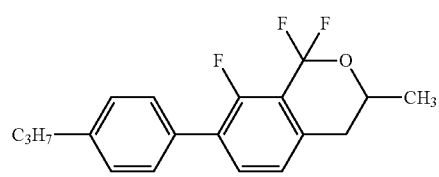 |
| 444 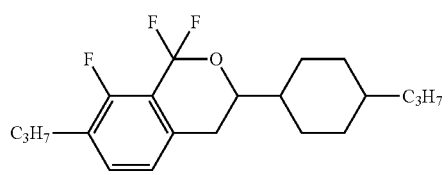 |
| 445 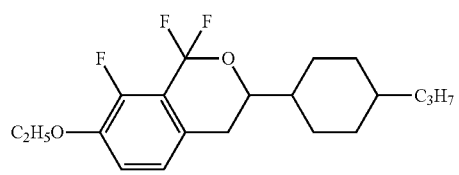 |

-continued
| No. | |
|---|---|
| 446 | 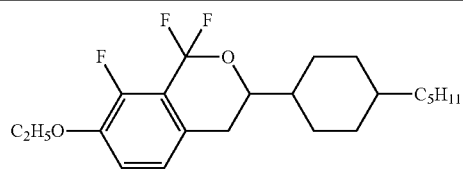 |
| 447 | 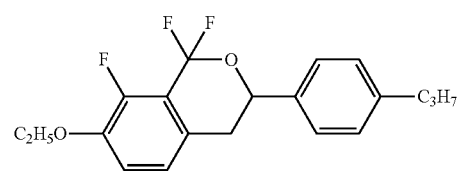 |
| 448 | 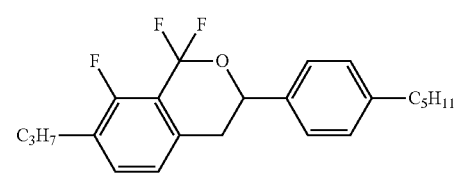 |
| 449 | 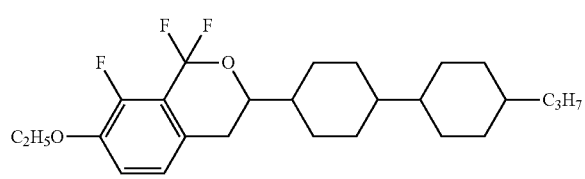 |
| 450 | 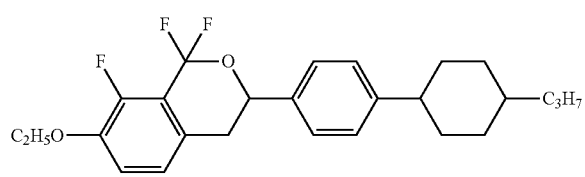 |
| 451 | 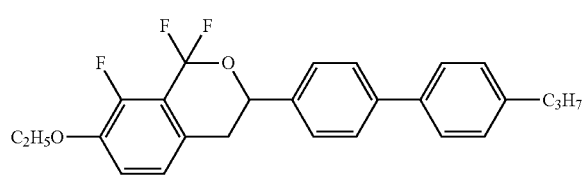 |
| 452 | 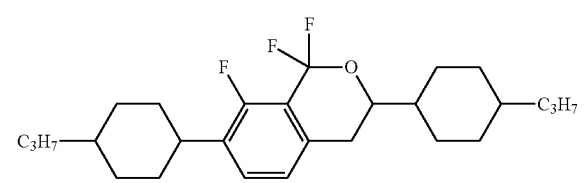 |
| 453 | 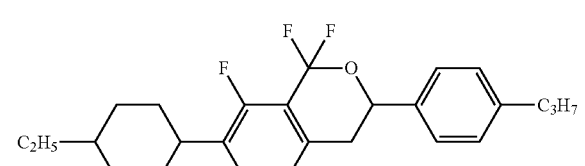 |
| 454 | 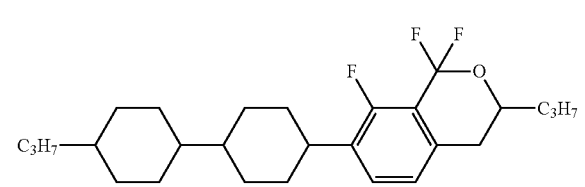 |

| No. | |
|---|---|
| 455 | 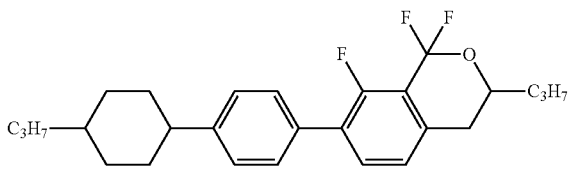 |
| 456 | 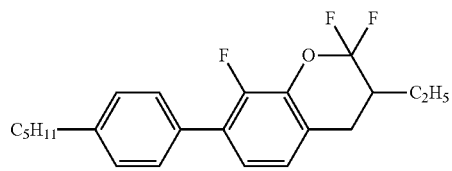 |

The invention claimed is:
1. A compound represented by general formula (a):

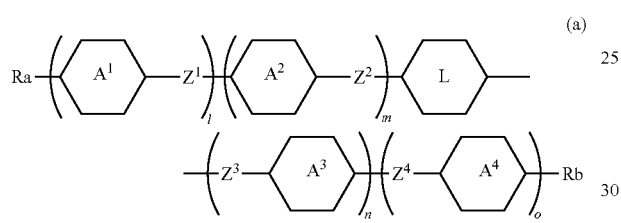

wherein in general formula (a),
Ra and Rb are each independently hydrogen, halogen or alkyl having approximately 1 to approximately 9 carbons, provided that in the alkyl, —CH$_2$— may be replaced by —O—, —CH$_2$CH$_2$— may be replaced by —CH=CH—, and hydrogen may be replaced by halogen;
rings A$^1$, A$^2$, A$^3$ and A$^4$ are each independently trans-1,4-cyclohexylene or 1,4-phenylene, provided that in these rings, hydrogen may be replaced by halogen, and in the case where the ring is trans-1,4-cyclohexylene, —CH$_2$— may be replaced by —O— or —CH=CH—, and in the case where the ring is 1,4-phenylene, —CH= may be replaced by —N=;
Z$^1$, Z$^2$, Z$^3$ and Z$^4$ are each independently a single bond or alkylene having 1 to 4 carbons, provided that in the alkylene, arbitrary —CH$_2$— may be replaced by —O— or —CO—, arbitrary —CH$_2$CH$_2$— may be replaced by —CH=CH— or —C≡C—, and arbitrary hydrogen may be replaced by halogen;
l, m, n and o are each independently 0 or 1; and
ring L is ring L2:

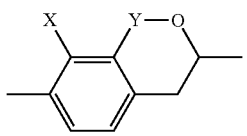

wherein in ring L2, X is hydrogen and Y is —CF$_2$—, or X is halogen and Y is —C(=O)— or —CF$_2$—.
2. A compound represented by any one of general formulas (a-1) to (a-7):

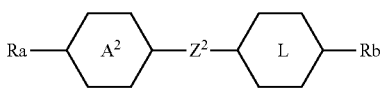 (a-1)

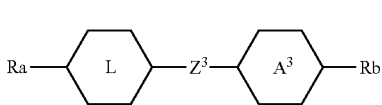 (a-2)

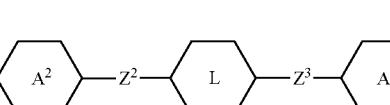 (a-3)

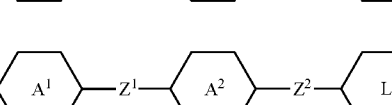 (a-4)

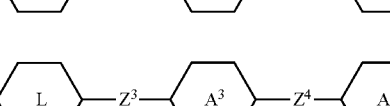 (a-5)

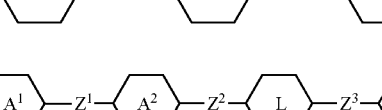 (a-6)

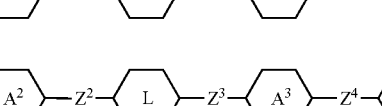 (a-7)

wherein in general formulas (a-1) to (a-7),
Ra and Rb are each independently hydrogen, halogen or alkyl having approximately 1 to approximately 9 carbons, provided that in the alkyl, —CH$_2$— may be replaced by —O—, —CH$_2$CH$_2$— may be replaced by —CH=CH—, and hydrogen may be replaced by halogen;
rings A$^1$, A$^2$, A$^3$ and A$^4$ are each independently trans-1,4-cyclohexylene or 1,4-phenylene, provided that in these rings, hydrogen may be replaced by halogen, and in the case where the ring is trans-1,4-cyclohexylene, —CH$_2$— may be replaced by —O— or —CH=CH—, and in the case where the ring is 1,4-phenylene, —CH= may be replaced by —N=;
Z$^1$, Z$^2$, Z$^3$ and Z$^4$ are each independently a single bond or alkylene having 1 to 4 carbons, provided that in the alkylene, arbitrary —CH$_2$— may be replaced by —O— or —CO—, arbitrary —CH$_2$CH$_2$— may be replaced by —CH=CH— or —C≡C—, and arbitrary hydrogen may be replaced by halogen; and ring L is ring L2:

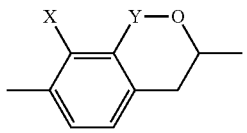

L2 wherein in ring L2, X is hydrogen and Y is —CF$_2$—, or X is halogen and Y is —C(=O)— or —CF$_2$—.

3. The compound by any one of general formulas (a-1) to (a-7) according to claim 2, wherein in ring L2, X is fluorine.

4. The compound by any one of general formulas (a-1) to (a-7) according to claim 2, wherein in ring L2, X is fluorine, and Y is —C(=O)—.

5. The compound by any one of general formulas (a-1) to (a-7) according to claim 2, wherein Ra and Rb are each alkyl having 1 to 9 carbons or alkoxy having 1 to 8 carbons; and in ring L2, X is fluorine, and Y is —C(=O)—.

6. The compound by any one of general formulas (a-1) to (a-7) according to claim 2, wherein in ring L2, X is fluorine, and Y is —CF$_2$—.

7. The compound by any one of general formulas (a-1) to (a-7) according to claim 2, wherein in ring L2, X is hydrogen, and Y is —CF$_2$—.

8. A liquid crystal composition comprising at least one compound selected from the group of the compound according to claim 1.

9. The liquid crystal composition according to claim 8, the composition further comprises at least one compound selected from the group of compounds represented by formulas (1), (2), (3), (4), (5), (6), (7), (8) and (9):

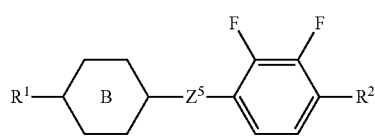 (1)

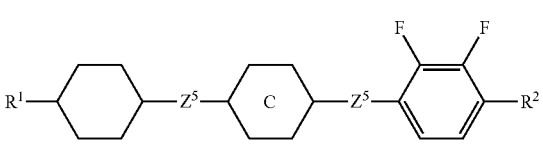 (2)

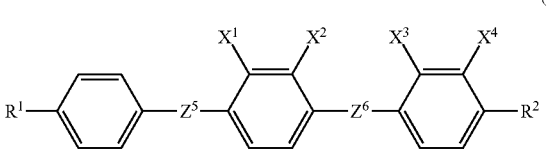 (3)

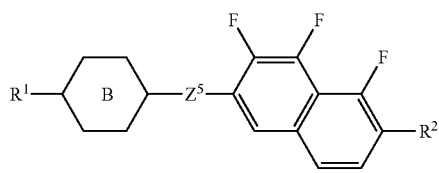 (4)

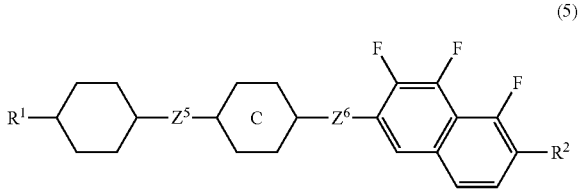 (5)

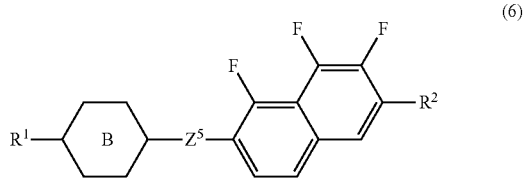 (6)

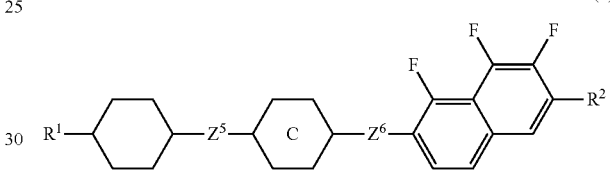 (7)

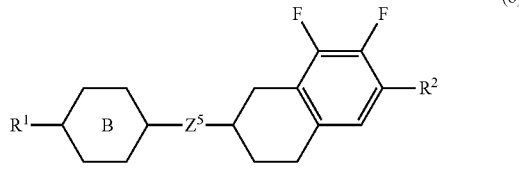 (8)

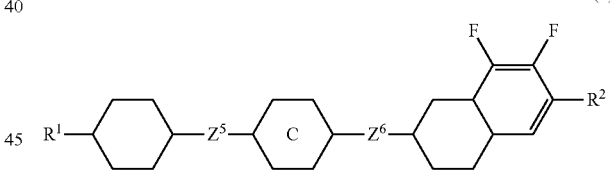 (9)

wherein in formulas (1) to (9),

R$^1$ and R$^2$ are each independently alkyl having 1 to 10 carbons, provided that in the alkyl, —CH$_2$— may be replaced by —O—, —(CH$_2$)$_2$— may be replaced by —CH=CH—, and arbitrary hydrogen may be replaced by fluorine, and R$^1$ may be fluorine;

ring B and ring C are each independently 1,4-cyclohexylene, 1,4-phenylene or decahydro-2,6-naphthylene;

Z$^5$ and Z$^6$ are each independently —(CH$_2$)$_2$—, —COO— or a single bond; and X$^1$, X$^2$, X$^3$ and X$^4$ are each independently hydrogen or fluorine, provided that at least one of X$^1$, X$^2$, X$^3$ and X$^4$ is fluorine.

10. The liquid crystal composition according to claim 8, the composition further comprises at least one compound selected from the group of compounds represented by formulas (10), (11) and (12):

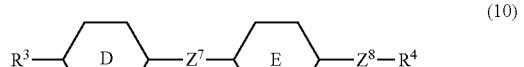 (10)

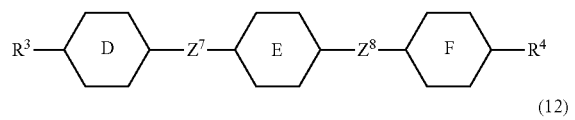 (11)

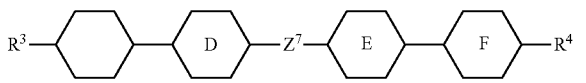 (12)

wherein in formulas (10) to (12), $R^3$ and $R^4$ are each independently alkyl having 1 to 10 carbons, provided that in the alkyl, —CH$_2$— may be replaced by —O—, —(CH$_2$)$_2$— may be replaced by —CH=CH—, and hydrogen may be replaced by fluorine;

ring D, ring E and ring F are each independently 1,4-cyclohexylene, pyrimidine-2,5-diyl, or 1,4-phenylene, arbitrary hydrogen of which may be replaced by fluorine; and $Z^7$ and $Z^8$ are each independently —C≡C—, —COO—, —(CH$_2$)$_2$—, —CH=CH— or a single bond.

11. The liquid crystal composition according to claim 9, the composition further comprises at least one compound selected from the group of compounds represented by formulas (10), (11) and (12) in claim 10.

12. The liquid crystal composition according to claim 8, wherein the composition further comprises at least one optically active compound.

13. A liquid crystal display device comprising the liquid crystal composition according to claim 8.

* * * * *